(12) United States Patent
MacRae

(10) Patent No.: US 7,064,246 B2
(45) Date of Patent: Jun. 20, 2006

(54) USE OF TRANSPOSABLE ELEMENTS FOR ALTERING GENE EXPRESSION

(76) Inventor: Amy F. MacRae, 1405 Mirandy Dr., St. Louis, MO (US) 63146

( * ) Notice: Subject to any disclaimer, the term of this patent is extended or adjusted under 35 U.S.C. 154(b) by 289 days.

(21) Appl. No.: 10/138,221

(22) Filed: May 1, 2002

(65) Prior Publication Data

US 2002/0199216 A1 Dec. 26, 2002

Related U.S. Application Data

(60) Provisional application No. 60/287,882, filed on May 1, 2001.

(51) Int. Cl.
C12N 15/82 (2006.01)
(52) U.S. Cl. .................. 800/291; 435/91.41; 435/468
(58) Field of Classification Search ................ 435/455, 435/468, 471, 91.41; 800/291
See application file for complete search history.

(56) References Cited

U.S. PATENT DOCUMENTS

| 5,034,322 A | 7/1991 | Rogers et al. |
| 5,352,605 A | 10/1994 | Fraley et al. |
| 5,378,619 A | 1/1995 | Rogers |

FOREIGN PATENT DOCUMENTS

EP 0 559 603 A2 9/1993

OTHER PUBLICATIONS

Friedlender et al. Repression of the Ac-transposase gene promoter by Ac transposase. The Plant Journal, 1996, vol. 9, No. 6, pp. 911-917.*
Grant et al. En/Spm encoded tnpA protein requires a specific target sequence for suppression. The EMBO Journal, 1990, vol. No. 7, pp. 2029-2035.*
Puchta et al. Gene replacement by homologous recombination in plants. Plant Molecular Biology, 2002, vol. 48, pp. 173-186.*
Bhattacharyya-Parkrasi et al., Specificity of a promoter from the rice tungro bacilliform virus for expression in phloem tissues. 1993, The Plant Journal, vol. 4, pp. 71-79.*
Scortecci et al., Negative effect of the 5'-untranslated leader sequence on Ac transposon promoter expression. 1999,Plant Molecular Biology, vol. 40, pp. 935-944.*
Weil and Kunze, Transposition of maize Ac/Ds transposable elements in the yeast *Saccharomyces cerevisiae*. 2000, Nature Genetics, vol. 26, pp. 187-190.*
Becker, H.A. and Kunze R. Maize Activator transposase has a bipartite DNA binding domain that recognizes subterminal sequences and the terminal inverted repeats. Mol Gen Genet. Apr. 16, 1997;254(3):219-30.*

Grant S.R. et al. En/Spm encoded tnpA protein requires a specific target sequence for suppression. EMBO J. Jul. 1990;9(7):2029-35.*
Agrawal et al., "Transposition mediated by RAG1 and RAG2 and its implications for the evolution of the immune system", 1998, Nature 394: 744-751.
Alatortsev et al., "P{lac W} Transposon Insertions with Gradual Expression of Reporter Genes", 2000, Russian Journal of Genetics 36: 509-513.
Altpeter et al., "Integration and expression of the high-molecular-weight glutenin subunit 1Ax1 gene into wheat", 1996, Nature Biotechnology 14: 1155-1159.
Amae et al., "Identification of a composite enhancer of the human tyrosinase-related protein 2/DOPAchrome tautomerase gene", 2000, Biochim. Biophys. Acta 1492: 505-508.
Amber, "Genetic Responses to Drought", 2000, The Scientist, Oct. 30th issue: 18-19.
Amrein et al., "The Role of Specific Protein-RNA and Protein-Protein Interactions in Positive and Negative Control of pre-mRNA Splicing by Transformer 2", 1994, Cell 76: 735-746.
Angelov et al., "Differential Remolding of the HIV-1 Nucleosome upon Transcription Activators and SWI/SNF Complex Binding", 2000, Journal of Mol. Biol. 302: 315-326.
Aravind, "The BED finger, a novel DNA-binding domain in chromatin-boundary-element-binding proteins and transposases", 2000, Trends in Biochem. Sci. 25: 421-423.

(Continued)

Primary Examiner—Cynthia Collins
(74) Attorney, Agent, or Firm—Amster, Rothstein & Ebenstein LLP

(57) ABSTRACT

Methods of repressing expression of a recombinant gene in a cell are provided. The methods include the steps of introducing a transposase DNA binding motif into or adjacent to the gene, and introducing into the cell a transposase that is capable of binding to the transposase DNA binding motif. Methods of producing a population of cells of an organism that vary in their expression of a gene are also provided. The methods involve transfecting the cells with a first polynucleotide sequence encoding the target gene operably linked to a promoter such that the target gene is expressed in the cells, wherein the vector has at least one transposase DNA binding motif within or adjacent to the target gene; and transfecting some of the cells with a second polynucleotide encoding the transposable element operably linked to a second promoter such that the transposable element is expressed in the cells. In these methods, the target gene in the cells transfected with the second polynucleotide exhibits reduced expression when compared to the target gene in the cells that are not transfected with the second polynucleotide. Kits having a first polynucleotide with a gene and a DNA transposase binding motif in or adjacent to the gene, and a second polynucleotide comprising a gene encoding a transposase that is capable of binding to the transposase DNA binding motif are also provided.

17 Claims, 5 Drawing Sheets

OTHER PUBLICATIONS

Argaman and Altuvia, "fhlA Repression by OxyS RNA: Kissing Complex Formation at Two Sites Results in a Stable Antisense-Target RNA Complex", 2000, Journal of Mol. Biol. 300; 1101-1112.

Arnold et al., "The insulator protein CTCF represses transcription on binding to the (gt)22(ga)15 microsatellite in intron 2 of the HLA-DRB1 0401 gene", 2000, Gene 253: 209-214.

Arthur et al., "Herpes Simplex Virus Type 1 Promoter Activity during Latency Establishment, Maintenance, and Reactivation in Primary Dorsal Root Neurons In Vitro", 2001, Journal Virol. 75: 3885-3895.

Baker et al., "Sequence and characterization of 6 Lea proteins and their genes from cotton", 1988, Plant Mol. Biol. 11: 277-291.

Balazs et al., "Nucleotide sequence of DNA from an altered-virulence isolate D/H of the cauliflower mosaic virus", 1982, Gene 19: 239-249.

Barcelo et al., "Transgenic cereal (tritordeum) plants obtained at high efficiency by microprojectile bombardment of inflorescence tissue", 1994, Plant Journal 5: 583-592.

Bash and Lohr, "Yeast Chromatin Structure and Regulation of GAL Gene Expression", 2000, Prog. Nucleic Acid Res. Mol. Biol. 65: 197-259.

Baum et al., "Reduction of G-box binding factor DNA binding activity, but not G-box binding factor abundance, causes the downregulation of RBCS2 expression during early tomato fruit development", 1999, FEBS Letters 454: 95-99.

Beato, "Gene Regulation by Steroid Hormones", 1989, Cell 56: 335-344.

Becker and Kunze, Binding sites for maize nuclear proteins in the subterminal regions of the transposable element Activator, 1996, Mol. Gen. Genet. 251: 428-435.

Becker and Kunze, "Maize Activator transposase has a bipartite DNA binding domain that recognizes subterminal sequences and the terminal Inverted repeats", 1997, Mol. Gen. Genet. 254: 219-230.

Becker et al., "The cab-m7 gene: a light-inducible, mesophyll-specific gene of maize", 1992, Plant Mol. Biol. 20: 49-60.

Behrens et al., "Cloning of the Zea mays controlling element Ac from the wx-m7 allele", 1984, Mol. Gen. Genet. 194: 346-347.

Benfey et al., "Tissue-specific expression from CaMV 35S enhancer subdomains in early stages of plant development", 1990a, EMBO Journal 9: 1677-1684.

Benfey et al., "Combinatorial and synergistic properties of CaMV 35S enhancer subdomains", 1990b, EMBO Journal 9: 1685-1696.

Benito and Walbot, "Characterization of the Maize Mutator Transposable Element MURA Transposase as a DNA-Binding Protein", 1997, Mol. Cell Biol. 17: 5165-5175.

Bhattacharyya-Pakrasi et al., "Specificity of a promoter from the rice tungro bacilliform virus for expression in phloem tissues", 1993, Plant Journal 4: 71-79.

Blechl and Anderson, "Expression of a novel high-molecular-weight glutenin subunit gene in transgenic wheat", 1996, Nat. Biotechnol. 14: 875-879.

Borkowska et al., "Transgenic Potato Plants Expressing Soybean beta-1,3-Endoglucanase Gene Exhibit an Increased Resistance to Phytophthora infestans", 1998, Z. Naturforsch [C] 53: 1012-1016.

Brehm et al., "Grapevine Protoplasts as a Transient Expression System for Comparison of Stilbene Synthase Genes Containing cGMP-Responsive Promoter Elements", 1999, Z. Naturforsch [C] 54: 220-229.

Brutnell and Dellaporta, "Somatic Inactivation and Reactivation of Ac Associated With Changes in Cytosine Methylation and Transposase Expression", 1994, Genetics 138: 213-225.

Bult et al., "Complete Genome Sequence of the Methanogenic Archaeon, *Methanococcus jannaschii*", 1996, Science 273: 1058-1073.

Bustos et al., "Positive and negative cis-acting DNA domains are required for spatial and temporal regulation of gene expression by a seed storage protein promoter", 1991, EMBO Journal 10: 1469-1479.

Carroll et al., "Germinal Transpositions of the Maize Element Dissociation From T-DNA Loci in Tomato", 1995, Genetics 139: 407-420.

Catteruccia et al., "Toward Anopheles transformation: Minos element activity in anopheline cells and embryos", 2000, Proc. Natl. Acad. Sci. USA 97: 2157-2162.

Chabouté et al., "Cell Cycle Regulation of the Tobacco Ribonucleotide Reductase Small Subunit Gene is Mediated by E2F-like Elements", 2000, Plant Cell 12: 1987-2000.

Chalfie, "Green Fluorescent Protein", 1995, Photochem. Photobiol. 62: 651-656.

Charng et al., "Construction of an inducible transposon, INAc, to develop a gene tagging system in higher plants", 2000, Mol. Breeding 6: 353-367.

Chaure et al., "Stable transformation of *Erysiphe graminis*, an obligate biotrophic pathogen of barley", 2000, Nat. Biotechnol. 18: 205-207.

Chen et al., "Transposition of Ac From the P Locus of Maize Into Unreplicated Chromosomal Sites", 1987, Genetics 117: 109-116.

Chernukhin et al., "Physical and Functional Interaction between Two Pluripotent Proteins, the Y-box DNA/RNA-binding Factor, YB-1, and the Multivalent Zinc Finger Factor, CTCF", 2000, Journal Biol. Chem. 275: 29915-29921.

Cho et al., "Overexpression of thioredoxin h leads to enhanced activity of starch debranching enzyme (pullulanase) in barley grain", 1999, Proc. Natl. Acad. Sci. USA 96: 14641-14646.

Chomet et al., "Inactivation of the maize transposable element Activator (Ac) is associated with its DNA modification", 1987, EMBO Journal 6: 295-302.

Chowrira et al., "Electroporation-Mediated Gene Transfer into Intact Nodal Meristems In Planta", 1995, Mol. Biotechnol. 3:17-23.

Christianson and Kafatos, "Binding Affinity of the *Drosophila melanogaster* CF1/USP Protein to the Chorion s15 Promoter", 1993, Biochem. Biophys. Res. Commun. 193: 1318-1323.

Chung et al., "Inhibition of Activator Protein 1 Activity and Cell Growth by Purified Green Tea and Black Tea Polyphenols in H-ras-transformed Cells: Structure-Activity Relationship and Mechanisms Involved", 1999, Cancer Res. 59: 4610-4617.

COMFORT, "The Real Point is Control': The Reception of Barbara McClintock's Controlling Elements", 1999, Journal of the History of Biology 32: 133-162.

Cordes et al., "Interaction of a Developmentally Regulated DNA-Binding Factor with Sites Flanking Two Different Fruit-Ripening Genes from Tomato", 1989, Plant Cell 1: 1025-1034.

Cornejo et al., "Activity of a maize ubiquitin promoter in transgenic rice", 1993, Plant Mol. Biol. 23: 567-581.

Dahl et al., "Genetic linkage of the vanB2 gene cluster to Tn5382 in vancomycin-resistant enterococci and characterization of two novel insertion sequences", 2000, Microbiol. 146: 1469-1479.

Davies et al., "Three-Dimensional Structure of the Tn5 Synaptic Complex Transposition Intermediate", 2000, Science 289: 77-85.

Deikman et al., "Separation of cis elements responsive to ethylene, fruit development, and ripening in the 5'-flanking region of the ripening-related E8 gene", 1998, Plant Mol. Biol. 37: 1001-1011.

Delattre et al., "P-element transposition in *Drosophila melanogaster*: influence of size and arrangement in pairs", 2000, Mol. Gen. Genet. 263: 445-454.

Deng and Brodie, "Roles of BrCA1 and its interacting proteins", 2000, Bioessays 22: 728-737.

Denisenko et al., "Zik1, a Transcriptional Repressor That Interacts with the Heterogeneous Nuclear Ribonucleoprotein Particle K Protein", 1996, Journal Biol. Chem. 271: 27701-27706.

Devit and Johnston, "The nuclear exportin Msn5 is required for nuclear export of the Mig1 glucose repressor of *Saccaromyces cerevisiae*", 1999, Curr. Biol. 9: 1231-1241.

Dure et al., "Common amino acid sequence domains among the LEA proteins of higher plants", 1989, Plant Mol. Biol. 12: 475-486.

Duval et al., "The Human T-Cell Transcription Factor-4 Gene: Structure, Extensive Characterization of Alternative Splicings, and Mutational Analysis in Colorectal Cancer Cell Lines", Cancer Res. 60: 3872-3879.

Ealing et al., "Expression of the pea albumin 1 gene in transgenic white clover and tobacco", 1994, Transgenic Res. 3: 344-354.

Elomaa et al., "Transgene inactivation in Petunia hybrida is influenced by the properties of the foreign gene", 1995, Mol. Gen. Genet. 248: 649-656.

Eriksson et al., "Deletion Mutagenesis of the 5' psbA2 Region in Synechocystis 6803: Identification of a Putative cis Element Involved in Photoregulation", 2000, Mol. Cell Biol. Res. Commun. 3: 292-298.

Essers et al., "A Highly Conserved Domain of the Maize Activator Transposase Is Involved in Dimerization", 2000, Plant Cell 12: 211-224.

Fafournoux et al., "Amino acid regulation of gene expression", 2000, Biochem. Journal 351: 1-12.

Falco et al., "Transgenic Canola and Soybean Seeds with Increased Lysine", 1995, Biotechnology 13: 577-582.

Fedoroff, "The Suppressor-mutator element and the evolutionary riddle of transposons", 1999, Genes Cells 4: 11-19.

Fedoroff et al., "Isolation of the Transposable Maize Controlling Elements Ac and Ds", 1983, Cell 35: 235-242.

Fedoroff et al., "Cloning of the bronze locus in maize by a simple and generalizable procedure using the transposable controlling element Activator (Ac)", 1984, Proc. Natl. Acad. Sci. USA 81: 3825-3829.

Feschotte and Mouches, 2000, Mol. Biol. Evol. 17: 730-737.

Finer and Finer, "Use of Agrobacterium expressing green fluorescent protein to evaluate colonization of sonication-assisted Agrobacterium-mediated transformation-treated soybean cotyledons", 2000, Lett. Appl. Microbiol. 30: 406-410.

Fitzmaurice et al., "Transposon Tagging of the Sulfur Gene of Tobacco Using Engineered Maize Ac/Ds Elements", 1999, Genetics 153: 1919-1928.

Fleischmann et al., "Whole-Genome Random Sequencing and Assembly of Haemophilus influenzae Rd", 1995, Science 269: 496-512.

Fouts et al., "Functional recognition of fragmented operator sites by R17/MS2 coat protein, a translational repressor", 1997, Nucleic Acids Res. 25: 4464-4473.

Fraser et al., "The Minimal Gene Complement of *Mycoplasma genitalium*", 1995, Science 270: 397-403.

Fridlender et al., "Repression of the Ac-transposase gene promoter by Ac transposase", 1996, The Plant Journal 9:911-917.

Fridlender et al., "Analysis of the Ac promoter: structure and regulation", 1998, Mol. Gen. Genet. 258: 306-314.

Fromm et al., "Stable transformation of maize after gene transfer by electroporation", 1986, Nature 319: 791-793.

Furusawa et al., "Identification of CIBP1 as Corepressors of Zinc Finger-Homeodomain Factor delta-EF1", 1999, Mol. Cell Biol. 19: 8581-8590.

Gallia et al., "Pur-alpha: a multifunctional single-stranded DNA- and RNA-binding protein 2000, Nucleic Acids Res. 28: 3197-3205.

Garrick et al., "Repeat-induced gene silencing in mammals", 1998, Nat. Genet. 18: 56-59.

Geffers et al., "Anaerobiosis-specific interaction of tobacco nuclear factors with cis-regulatory sequences in the maize GapC4 promoter", 2000, Plant Mol. Biol. 43: 11-21.

Good et al., "Reduced ethylene synthesis by transgenic tomatoes expressing S-adenosylmethionine hydrolase", 1994, Plant Mol. Biol. 26: 781-790.

Goto et al., "Iron fortification of rice seed by the soybean ferritin gene", 1999, Nat. Biotechnol. 17: 282-286.

Govantes et al., "Oxygen regulation of the *Escherichia coli* cytochrome d oxidase (cydAB) operon: roles of multiple promoters and the Fnr-1 and Fnr-2 binding sites" 2000, Mol. Microbiol. 37: 1456-1469.

Gowri et al., "Stress responses in alfalfa (*Medicago sativa* L.) 12. Sequence analysis of phenylalanine ammonia-lyase (PAL) cDNA clones and appearance of PAL transcripts in elicitor treated cell cultures and developing plants" 1991, Plant Mol. Biol. 17: 415-429.

Grichko et al., "Increased ability of transgenic plants expressing the bacterial enzyme ACC deaminase to accumulate Cd, Co, Cu, Ni, Pb, and Zn", 2000, Journal Biotechnol. 81: 45-53.

Guilley et al., "Transcription of Cauliflower Mosaic Virus DNA: Detection of Promoter Sequences, and Characterization of Transcripts", 1982, Cell 30: 763-773.

Hagenbeek et al., "Trivalent Ions Activate Abscisic Acid-Inducible Promoters through an ABI 1-Dependent Pathway in Rice Protoplasts", 2000, Plant Physiol. 123: 1553-1560.

Haider et al., "Specificity of *Bacillus thuringiensis* var. colmeri insecticidal delta-endotoxin is determined by differential proteolytic processing of the protoxin by larval gut proteases", 1986, Eur. Journal Biochem. 156: 531-540.

Han et al., "New transposable elements identified as insertions in rice transposon Tnr1", 2000, Genes Genet. Syst. 75: 69-77.

Handler and Harrell, "Germline transformation of *Drosophila melanogaster* with the piggyBac transposon vector", 1999, Insect Mol. Biol. 8: 449-457.

Harada et al., "Unusual sequence of an abscisic acid-inducible mRNA which accumulates late in *Brassica napus* seed development", 1989, Plant Mol. Biol. 12: 395-401.

Hedley et al., "Differential expression of invertase genes in internal and external phloem tissues of potato (*Solanum tuberosum* L.)", 2000, Journal Exp. Bot. 51: 817-821.

Heifetz, "Genetic engineering to the chloroplast", 2000, Biochimie 82: 655-666.

Heinlein et al., "Changing Patterns of Localization of the Tobacco Mosaic Virus Movement Protein and Replicase to the Endoplasmic Reticulum and Microtubules during Infection", 1996, Plant Cell 10: 1107-1120.

Henrich et al., "A steroid/thyroid hormone receptor superfamily member in *Drosophila melanogaster* that shares extensive sequence similarity with a mammalian homologue", 1990, Nucleic Acids Res. 18: 4143-4148.

Hofmann et al., "Specificity of *Bacillus thuringiensis* delta-endotoxins is correlated with the presence of high-affinity binding sites in the brush border membrane of target insect midguts", 1988, Proc. Natl. Acad. Sci. USA 85: 7844-7848.

Hong et al., "Cloning and characterization of a cDNA encoding a mRNA rapidly-induced by ABA in barley aleurone layers", 1988, Plant Mol. Biol. 11: 495-506.

Hua et al., "A 69 bp fragment in the pyrroline-5-carboxylate reductase promoter of Arabidopsis thaliana activates minimal CaMV 35S promoter in a tissue-specific manner", 1999, FEBS Letters 458: 193-196.

Hughes and Galau, "Developmental and Environmental Induction of Lea and LeaA mRNAs and the Postabscission Program during Embryo Culture", 1991, Plant Cell 3: 605-618.

International Human Genome Sequencing Consortium, "Initial sequencing and analysis of the human genome", Feb. 2001, Nature 409: 860-921.

Izawa et al., "Transposon tagging rice", 1997, Plant Mol. Biol. 35: 219-229.

Jasinskiene et la., "Structure of Hermes integrations in the germline of the yellow fever mosquito, *Aedes aegypti*", 2000, Insect Mol. Biol. 9: 11-18.

Jefferson, "Assaying Chimeric Genes in Plants: The GUS Gene Fusion System", 1987, Plant Mol. Biol. Reporter 5: 387-405.

Jefferson et al., "GUS fusions: beta-glucuronidase as a sensitive and versatile gene fusion marker in higher plants", 1987, EMBO Journal 6: 3901-3907.

Jimenez et al., "A Conserved Motif in Goosecoid Mediates Groucho-Dependent Repression in *Drosophila embryos*", 1999, Mol. Cell Biol. 19: 2080-2087.

Johns et al., "A low copy number, copia-like transposon in maize", 1985, EMBO Journal 4: 1093-1102.

Juszczuk et al., "Effect of genomic and subgenomic leader sequences of potato leafroll virus on gene expression", 2000, FEBS Letters 484: 33-36.

Kastaniotis et al., "Roles of Transcription Factor Mot3 and Chromatin in Repression of the Hypoxic Gene ANB1 in Yeast", 2000, Mol. Cell Biol. 20: 7088-7098.

Keller et al., "dCtBP-Dependent and -Independent Repression Activities of the *Drosophila knirps* Protein", 2000, Mol. Cell Biol. 20: 7247-7258.

Keller et al., "RNA Replication from the Simian Virus 5 Antigenomic Promoter Requires Three Sequence-Dependent Elements Separated by Sequence-Independent Spacer Regions", 2001, Journal Virol. 75: 3993-3998.

Kempken and Kück, "Tagging of a nitrogen pathway-specific regulator gene in Tolypocladium inflatum by the transposon Restless", 2000, Mol. Gen. Genet. 263: 302-308.

Keown et al., "Methods for Introducing DNA into Mammalian Cells", 1990, Methods Enzymol. 185: 527-536.

Kipling and Warburton, "Centromeres, CENP-B and Tigger too", 1997, Trends Genet. 13: 141-145.

Kishi et al., "Lineage-specific regulation of the murine RAG-2 promoter: GATA-3 in T cells and Pax-5 in B cells", 2000, Blood 95: 3845-3852.

Klinakis et al., "Mobility assays confirm the broad host-range activity of the Minos transposable element and validate new transformation tools", 2000a, Insect Mol. Biol. 9: 269-275.

Klinakis et al., "Genome-wide insertional mutagenesis in human cells by the *Drosophila mobile* element Minos", 2000b, EMBO Reports 1: 416-421.

Koelle et al., "The Drosophila EcR Gene Encodes an Ecdysone Receptor, a New Member of the Steoid Receptor Superfamily", 1991, Cell 67: 59-77.

Koloteva et al., The Position Dependence of Translational Regulation via RNA-RNA and RNA-Protein Interactions in the 5'-Untranslated Region of Eukaryotic mRNA Is a Function of the Thermodynamic Competence of 40 S Ribosomes in Translational.

Kunze et al., "Transcription of transposable element Activator (Ac) of Zea mays L.", 1987, EMBO Journal 6: 1555-1563.

Kunze et al., "Plant Transposable Elements", 1997, In: Callow (ed) Advances in Botanical Research, vol. 27: 331-470, Academic Press, New York, NY.

Laurin et al., "The hormone-sensitive lipase gene is transcribed from at least five alternative first exons in mouse adipose tissue", 2000, Mamm. Genome 11: 972-978.

Lawley et al., "Short Communication/Analysis of the Complete Nucleotide Sequence of the Tetracycline-Resistance Transposon Tn10", 2000, Plasmid 43: 235-239.

Le et al., "Transposon diversity in *Arabidopsis thaliana*", 2000, Proc. Natl. Acad. Sci. USA 97: 7376-7381.

Lechner et al., "PTIP, a novel BRCT domain-containing protein interacts with Pax2 and is associated with active chromatin", 2000a, Nucleic Acids Res. 28: 2741-2751.

Lechner et al., "Molecular Determinants for Targeting Heterochromatin Protein 1-Mediated Gene Silencing: direct Chromoshadow Domain-KAP-1 Corepressor Interaction Is Essential", 2000b, Mol. Cell Biol. 20: 6449-6465.

Leisner and Gelvin, "Structure of the octopine synthase upstream activator sequence", 1988, Proc. Natl. Acad. Sci. USA 85: 2553-2557.

Lepetit et al., "Glider and Vision: two new families of miniature inverted-repeat transposable elements in Xenopus laevis genome", 2000, Genetica 108: 163-169.

Li et al., "Secretion of Active Recombinant Phytase from Soybean Cell-Suspension Culutres", 1997, Plant Physiol. 114: 1103-1111.

Li et al., "Inversion and Transposition of Tc1 Transposon of C. elegans in Mammalian Cells", 1998, Somat. Cell Mol. Genet. 24: 363-369.

Lim et al., "Altering the RNA Binding Specificity of a Translational Repressor", 1994, Journal Biol. Chem. 269: 9006-9010.

Lloyd et al., "Epidermnal Cell Fate Determination in *Arabidopsis*: Patterns Defined by a Steroid-Inducible Regulator", 1994, Science 266: 436-439.

Long et al., "Analysis of the frequency of inheritance of transposed Ds elements in *Arabidopsis* after activation by a CaMV 35S promoter fusion to the Ac transposase gene", 1993, Mol. Gen. Genet. 241: 627-636.

Ludewig and Sonnewald, "High CO2-mediated down -regulation of photosynthetic gene transcripts is caused by accelerated senescence rather than sugar accumulation", 2000, FEBS Letters 479: 19-24.

Luo and Farrand, "Signal-dependent DNA binding and functional domains of the quorum-sensing activator TraR as identified by repressor activity", 1999, Proc. Natl. Acad. Sci. USA 96: 9009-9014..

Luo et al., "Expression and parent-of-origin effects for FIS2, MEA, and FIE in the endosperm and embryo of developing *Arabidopsis* seeds", 2000, Proc. Natl. Acad. Sci. USA 97: 10637-10642.

Lyznik et al., "Stable co-transformation of maize protoplasts with gusA and neo genes", 1989, Plant Mol. Biol. 13: 151-161.

MacLean et al., "Differential effects of sodium butyrate on the transcription of the human TIS11 family of early-response genes in colorectal cancer cells", 1998, Br. Journal Biomed. Sci. 55: 184-191.

MacRae et al., "Analysis of hexamer and pentamer motifs within a maize database: the presence of motif 'signatures' in functional gene categories", 1999, Genetica 105: 19-29.

MacRae, "Flexible tools for regulating plant gene expression: utilization of the maize Activator transposable element system" 1999, NSF Submitted Grant Proposal No. 9986293, DUNS #044193006).

Manevski et al., "In synergy with various cis-acting elements, plant insterstitial [interstitial] telomere motifs regulate gene expression in *Arabidopsis* root meristems", 2000, FEBS Letters 483: 43-46.

Martusewitsch et al., "High Spontaneous Mutation Rate in the Hyperthermophillic Archaeon Sulfolobus solfataricus Is Mediated by Transposable Elements", 2000, Journal Bacteriol. 192: 2574-2581.

Marx, "Interfering With Gene Expression", 2000, Science 288: 1370-1372.

Matzke et al., "Transgene silencing by the host genome defense: implications for the evolution of epigenetic control mechanisms in plannts and vertebrates", 2000, Plant Mol. Biol. 43: 401-415.

Messeguer et al., "Characterization of the level, target sites and inheritance of cylosine methylation in tomato nuclear DNA", 1991, Plant Mol. Biol. 16: 753-770.

Miller, Jr., "Association of Replicative T4 Deoxyribonucleic Acid and Bacterial Membranes", 1972, Journal Virol. 10: 920-924.

Morrison et al., "FBI-1, a factor that binds to the HIV-1 inducer of short transcripts (IST), is a POZ domain protein", 1999, Nucleic Acids Res. 27: 1251-1262.

Mukhopadhyaya et al., "A soxA Gene, Encoding a Diheme Cytochrome c, and a sox Locus, Essential for Sulfur Oxidation in a New Sulfur Lithotrophic Bacterium", 2000, Journal Bacteriol. 182: 4278-4287.

Müller-Neumann et al., "The DNA sequence of the transposable element Ac of Zea mays L.", 1984, Mol. Gen. Genet. 198: 19-24.

Mundy et al., "Nuclear proteins bind conserved elements in the abscisic acid-responsive promoter of a rice rab gene", 1990, Proc. Natl. Acad. Sci. USA 87: 1406-1410.

Muskens et al., "Role of inverted DNA repeats in transcriptional and post-transcriptional gene silencing", 2000, Plant Mol. Biol. 43: 243-260.

Nagai et al., "A New IS4 Family Insertion Sequence, IS4Bsu1, Responsible for Genetic Instability of Poly-gamma-Glutamic Acid", 2000, Journal Bacteriol. 182: 2387-2392.

Nakamura et al., "VNTR (variable number of tandem repeat) sequences as transcriptional, translational, or functional regulators", 1998, Journal Hum. Genet. 43: 149-152.

Nakazato et al., "Thyroglobulin Repression of Thyroid Transcription Factor 1 (TTF-1) Gene Expression Is Mediated by Decreased DNA Binding of Nuclear Factor P I Proteins Which Control Constitutive TTF-1 Expression", 2000, Mol. Cell Biol. 20: 8499-8512.

Neely and Hoffman, "Protein Kinase A and Mitogen-Activated Protein Kinase Pathways Antagonistically Regulate Fission Yeast fbp1 Transcription by Employing Different Modes of Action at Two Upstream Activation Sites", 2000, Mol. Cell Biol. 20:

Noury et al., "A transgenic rice cell lineage expressing the oat arginine decarboxylase (adc) cDNA constitutively accumulates putrescine in callus and seeds but not in vegetative tissues", 2000, Plant Mol. Biol. 43: 537-544.

Odell et al., "Identification of DNA sequences required for activity of the cauliflower mosaic virus 35S promoter", 1985, Nature 313: 810-812.

Odell et al., "Plant Gene Systems and Their Biology", 1987, Journal Cell Biochem. (Suppl. 11B): 60.

Odell et al., "Properties of an isolated transcription stimulating sequence derived from the cauliflower mosaic virus 35S promoter", 1988, Plant Mol. Biol. 10: 263-272.

Oliver et al., "Preferential Binding of fd Gene 5 Protein to Tetraplex Nucleic Acid Structures", 2000, Journal Mol. Biol. 301: 575-584.

Osbourn et al., "Evidence that Nucleocapsid Disassembly and a Later Step in Virus Replication Are Inhibited in Transgenic Tobacco Protoplasts Expressing TMV Coat Protein", 1989, Virol. 172: 370-373.

Ostareck-Lederer et al., "Translation of 15-lipoxygenase mRNA is inhibited by a protein that binds to a repeated sequence in the 3' untranslated region", 1994, EMBO Journal 13: 1476-1481.

Parker, "Structure and function of nucelar hormone receptors", 1990, Semin. Cancer Biol. 1: 81-87.

Pastorcic and Das, "Regulation of Transcription of the Human Presenilin-1 Gene by Ets Transcription Factors and the p53 Protooncogene", 2000, Journal Biol. Chem. 275: 34938-34945.

Pedersen et al., "Interaction of the *Chlamydia trachomatis* histone H1-like protein (Hc1) with DNA and RNA causes repression of transcription and translation in vitro", 1994, Mol. Microbiol. 11: 1085-1098.

Perlak et al., "Insect Resistant Cotton Plants", 1990, Biotechnol. (NY) 8: 939-943.

Peronnet et al., "Three-partner conversion induced by the P-element transposase in *Drosophila melanogaster*", 2000, Mol. Gen. Genet. 262: 1123-1131.

Phogat et al., "A four-element based transposon system for allele specific tagging in plants—Theoretical considerations", 2000, Journal Biosci. 25: 57-63.

Picton et al., "Sequence of a Cloned Tomato Ubiquitin Conjugating Enzyme", 1993, Plant Physiol. 103: 1471-1472.

Pinkerton et al., "The Queensland fruit fly, *Bactrocera tryoni*, contains multiple members of the hAT family of transposable elements", 1999, Insect Mol. Biol. 8: 423-434.

Pohlman et al., "The Nucleotide Sequence of the Maize Controlling Element Activator", 1984, Cell 37: 635-643.

Potikha et al., "The Involvement of Hydrogen Peroxide in the Differentiation of Secondary Walls in Cotton Fibers", 1999, Plant Physiol. 119: 849-858.

Pugh, "Control of gene expression through regulation of the TATA-binding protein", 2000, Gene 255: 1-14.

Quaedvlieg et al., "Fusions between green fluorescent protein and beta-glucuronidase as sensitive and vital bifunctional reproters in plants", 1998, Plant Mol. Biol. 37: 715-727.

Raizada and Walbot, "The Late Developmental Pattern of Mu Transposon Excision Is Conferred by a Cauliflower Mosaic Virus 35S-Driven MURA cDNA in Transgenic Maize", 2000, Plant Cell 12: 5-21.

Rao et al., "Recognition of triple-helical DNA structures by transposon Tn7", 2000, Proc. Natl. Acad. Sci. USA 97: 3936-3941.

Raynal et al., "Characterization of a Radish Nuclear Gene Expressed during Late Seed Maturation", 1989, Plant Physiol. 91: 829-836.

Reichel and Beachy, "Degradation of Tobacco Mosaic Virus Movement Protein by the 26S Proteasome", 2000, Journal Virol. 74: 3330-3337.

Reznikoff et al., "Tn5: A Molecular Window on Transposition", 1999, Biochem. Biophys. Res. Commun. 266: 729-734.

Rommens et al., "Differential Repair of Excision Gaps Generated by Transposable Elements of the 'Ac Family'", 1993, Bioessays 15: 507-512.

Sasaki et al., "Erythropoietin: Multiple Physiological Functions and Regulation of Biosynthesis", 2000, Biosci. Biotechnol. Biochem. 64: 1775-1793.

Sautter et al., "Micro-Targeting: High Efficiency Gene Transfer Using a Novel Approach for the Acceleration of Micro-Projectiles", 1991, Biotechnol. 9: 1080-1085.

Schena et al., "A steroid-inducible gene expression system for plant cells", 1991, Proc. Natl. Acad. Sci. USA 88: 10421-10425.

Schläppi et al., "Epigenetic Regulation of the Maize Sprm Transposable Element: Novel Activation of a Methylated Promoter by TnpA", 1994, Cell 77: 427-437.

Schläppi et al., "A highly sensitive plant hybrid protein assay ststem based on the Sprm promoter and TnpA protein for detection and anaylsis of transcription activation domains", 1996, Plant Mol. Biol 32: 717-725.

Schoenbeck et al., "Decreased NADH gultamate synthase activity in nodules and flowers of alfalfa (*Medicago sativa* L.) transformed with an antisense glutamate synthase transgene", 2000, Journal Exp. Bot. 51: 29-39.

Scortecci et al., "Negative effect of the 5'-untranslated leader sequence on Ac transposon promoter expression", 1999, Plant Mol. Biol. 40: 935-944.

Selvakumaran et al., "Ovarian Epithelial Cell Lineage-specific Gene Expression Using the Promoter of a Retrovirus-like Element", 2001, Cancer Res. 61: 1291-1295.

Shiina et al., "Chloroplast Tubules Visualized in Transplastomic Plants Expressing Green Fluoresecent Protein", 2000, Plant Cell Physiol. 41: 367-371.

Shimamoto et al., "Trans-activation and stable integration of the maize transposable element Ds cotransfected with the Ac transposase gene in transgenic rice plants", 1993, Mol. Gen. Genet. 239: 354-360.

Shimizu et al., "CpG distribution patterns inmethylated and non-methylated species", 1997, Gene 205: 103-107.

Shimizu et al., "Extrachromosomal transposition of the transposable element Minos occurs in embryos of the silkworm *Bombyx mori*", 2000, Insect Mol. Biol. 9: 277-281.

Sisk et al., "MHC Class II Transactivator Inhibits IL-4 Gene Transcription by Competing with NF-AT to Bind the Coactivator CREB Binding Protein (CBP)/p300", 2000, Journal Immunol. 165: 2511-2517.

Smania et al., "A sequence similar to bacterial transposable IS elements present in the 5' untranslated region of the bovine butanediol dehydrogenase cDNA", 1999, Genetica 105: 233-238.

Solis et al., "Ac-mediated trans-activation of the Ds element in rice (*Oryza sativa* L.) cells as revealed by GUS assay", 1999, Hereditas 131; 23-31.

Soutoglou et al., "Acetylation Regulates Transcription Factor Activity at Multiple Levels", 2000, Mol. Cell 5: 745-751.

Spellerberg et al., "Identification of a novel insertion sequence element in *Streptococcus agalactiae*", 2000, Gene 241: 51-56.

Stewart, Jr. et al., "Genetic Transformation, Recovery, and Characterization Fertile Soybean Transgenic for a Synthetic *Bacillus thuringiensis* crylAc Gene", 1996, Plant Physiol. 112: 121-129.

Strömvik et al., "A novel promoter from soybean that is active in a complex developmental pattern with and without its proximal 650 base pairs", 1999, Plant Mol. Biol. 41: 217-231.

Suzuki et al., "A novel transposon tagging element for obtaining gain-of-function mutants based on a self-stabilizing Ac derivative", 2001, Plant Mol. Biol. 45: 123-131.

Takumi et al., "Variations in the maize Ac transposase transcript level and the Ds excision frequency in transgenic wheat callus line", 1999, Genome 42: 1234-1241.

Tamura (Toshiki) et al., "Germline transformation of the silkworm *Bombyx mori* L. using a piggyBac transposon-derived vector", 2000, Nat. Biotechnol. 18: 81-84.

Tansey and Shechter, "Squalene Synthase: Structure and Regulation", 2000, Prog. Nucleic Acid Res. Mol. Biol. 65: 157-195.

Tatematsu et al., "MBD2-MBD3 complex binds to hemimethylated DNA and forms a complex containing DNMT1 at the replication foci in late S phase", 2000, Genes Cells 5: 677-688.

Tercé-Laforgue et al., "A strong constitutive positive element is essential for the ammonium-regulated expression of a soybean gene encoding cytosolic gultamine synthetase", 1999, Plant Mol. Biol. 39: 551-564.

Terzaghi and Cashmore, "Plant Cell Transfection by Electroporation", 1997, Methods Mol. Biol. 62: 453-462.

Thain et al., "Functional independence of circadian clocks that regulate plant gene expression", 2000, Curr. Biol. 10: 951-956.

Thomas et al., "Herterodimerization of the *Drosophila* ecdysone receptor with retinoid X receptor and ultraspiracle", 1993, Nature 362: 471-475.

Tommerup et al., "Barley Hydroiases and Ribosome-Inactivating Proteins Inhibit Fungal Growth", 1990, Eur. Congr. Biotechnol. 5: 916-918.

Tosi and Beverley, "cis and trans factors affecting Mos1 mariner evolution and transposition in vitro, and its potenital for functional genomics", 2000, Nucleic Acids Res. 28: 784-790.

Trieu et al., "Transformation of *Medicago truncatula* vial infiltration of seedings or flowering plants with *Agrobacterium*", 2000, Plant Journal 22: 531-541.

Tu, "Molecular and Evolutionary Analysis of Two Divergent Subfamilies of Novel Miniature Inverted Repeat Transposable Element in the Yellow Fever Mosquito, *Aedes aegypti*", 2000, Mol. Biol. Evol. 17: 1313-1325.

Turlan and Chandler, "Playing second fiddle: second-strand processing and liberation of transposable elements from donor DNA", 2000, Trends Microbiol. 8: 268-274.

Urnov et al., "Targeting of N-CoR and histone deacetylase 3 by the oncoprotein v-ErbA yields a chromatin infrastructure-dependent transcriptiona repression pathway", 2000, EMBO Journal 19: 4074-4090.

Van Houdt et al., "Both sense and antisense RNAs are targets for the sense transgene-induced posttranscriptional silencing mechanims", 2000, Mol. Gen. Genet. 263L 995-1002.

Van West et al., "Green fluorescent protein (GFP) as a reporter gene for the plant pathogenic oomycete *Phytophthora palminvora*", 1999, FEMS Microbiol Lett. 178: 71-80.

Verdaguer et al., "Isolation and expression in transgenic tobacco and rice plants, of the cassava vein mosaic virus (CVMV) promoter", 1996, Plant Molecular Biology 31: 1129-1139.

Vicient et al., "Differential expression of the *Arabidopsis* genes coding for Em-like proteins", 2000, Journal Exp. Bot. 51: 1211-1220.

Vilardell et al., "Gene sequence, developmental expression, and protein phosphorylation of RAB-17 in maize", 1990, Plant Mol. Biol. 14: 423-432.

Vilardell et al., "Multiple Functions of an Evolutionarily Conserved RNA Binding Domain", 2000, Mol. Cell 5: 761-766.

Vincent et al., "Overexpression of a soybean gene encoding cytosolic glutamine synthelase in shoots of transgenic *Lotus corinculatus* L. plants triggers changes in ammonium assimillation and plant development", 1997, Planta 201: 424-433.

Volff and Altenbuchner, "The 1-kb-repeat-encoded DNA-binding protein as repressor of an alpha-glucosidase operon flanking the amplifiable sequence AUD1 of *Streptomyces lividans*", 2000, Microbiology 146 (Pt 4): 923-933.

Wandelt et al., "Vicilin with carboxy-terminal KDEL is retained in the endoplasmic reticulum and accumulates to high levels in the leaves of transgenic plants", 1992, Plant Journal 2: 181-192.

Wang et al., "Regulation of Histone Deacetylase 4 by Binding of 14-3-3 Proteins", 2000a, Mol. Cell biol. 20: 6904-6912.

Wang et al., "Mariner (Mos1) transposase and genomic integration of foreign gene sequences in *Bombyx mori* cells", 2000b, Insect Mol. Biol. 9: 145-155.

Wang et al., "Identification of a Novel Plant Virus Promoter using a Polyvirus Infectious Clone", 2000c, Virus Genes 20: 11-17.

Warbrick et al., "PCNA binding proteins in *Drosophila melanogaster*: the analysis of a conserved PCNA binding domain", 1998, Nucleic Acids Res. 26: 3925-3932.

Weil and Kunze, "Transposition of maize Ac/Ds transposable elements in the yeast *Saccharomyces cerevisiae*", 2000, Nature Genet 26: 187-190.

Whitbred and Schuler, "Molecular Characterization of CYP73A9 and CYP82A1 P450 Genes Involved in Plant Defense in Pea", 2000, Plant Physiol. 124: 47-58.

Wielgosz et al., "Sequence Requirements for Sindbus Virus Subgenomic mRNA Promoter Function in Cultured Cells", 2001, Journal Virol. 75: 3509-3519.

Williams and Baker, "Transposase Team Puts a Headlock on DNA", 2000, Science 289: 73-74.

Xiao and Peterson, "Intrachromosomal homologous recombination in *Arabidopsis* induced by a maize transposon", 2000, Mol. Gen. Genet. 263: 22-29.

Yamada and Bohnert, "Expression of the PIP Aquaporin Promoter-MipA from the Common Ice Plant in Tobacco", 2000, Plant Cell Physiol. 41: 719-725.

Yamamoto et al., "Promoter analysis of seed storage protein genes from *Canavalia gladiata* D.C.", 1995, Plant Mol. Biol. 27: 729-741.

Yamasaki et al., "A Complex Insertion Sequence Cluster at a Point of Interaction between the Linear Plasmid SCP1 and the Linear Chromosome of *Streptomyces coelicolor* A3(2)", 2000, Journal Bacteriol. 182: 3104-3110.

Yant et al., "Somatic integration and long-term transgene expression in normal and haemophilic mice using a DNA transposon system", 2000, Nat. Genet. 25: 35-41.

Zhang (Hailan) and Levine, "Groucho and dCtBP mediate separate pathways of transcriptional repression in the *Drosophila* embryo", 1999, Proc. Natl. Acad. Sci. USA 96: 535-540.

Zhang (Pu) et al., "PU.1 inhibits GATA-1 functiona nd erythroid differentiation by blocking GATA-1DNA binding", 2000a, Blood 96: 2641-2648.

Zhang (J.K.) et al., "In vivo transposon mutagenesis of the *Methanogenic archaeon Methanosarcina acetivorans* C2A using a modified version of the insect mariner-family transposable element Himar1", 2000b, Proc. Natl. Acad. Sci. USA 97: 9665-9670.

\* cited by examiner

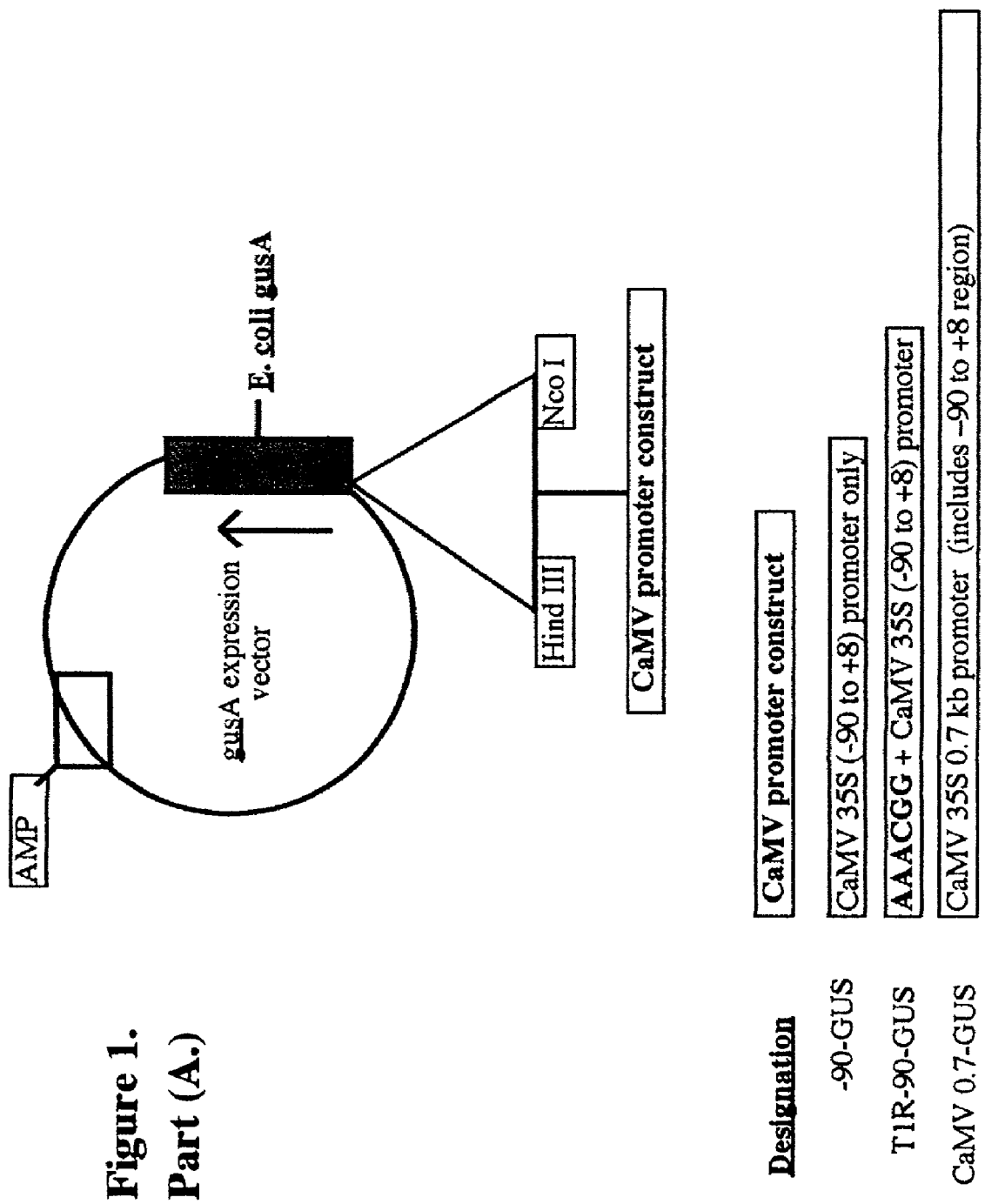

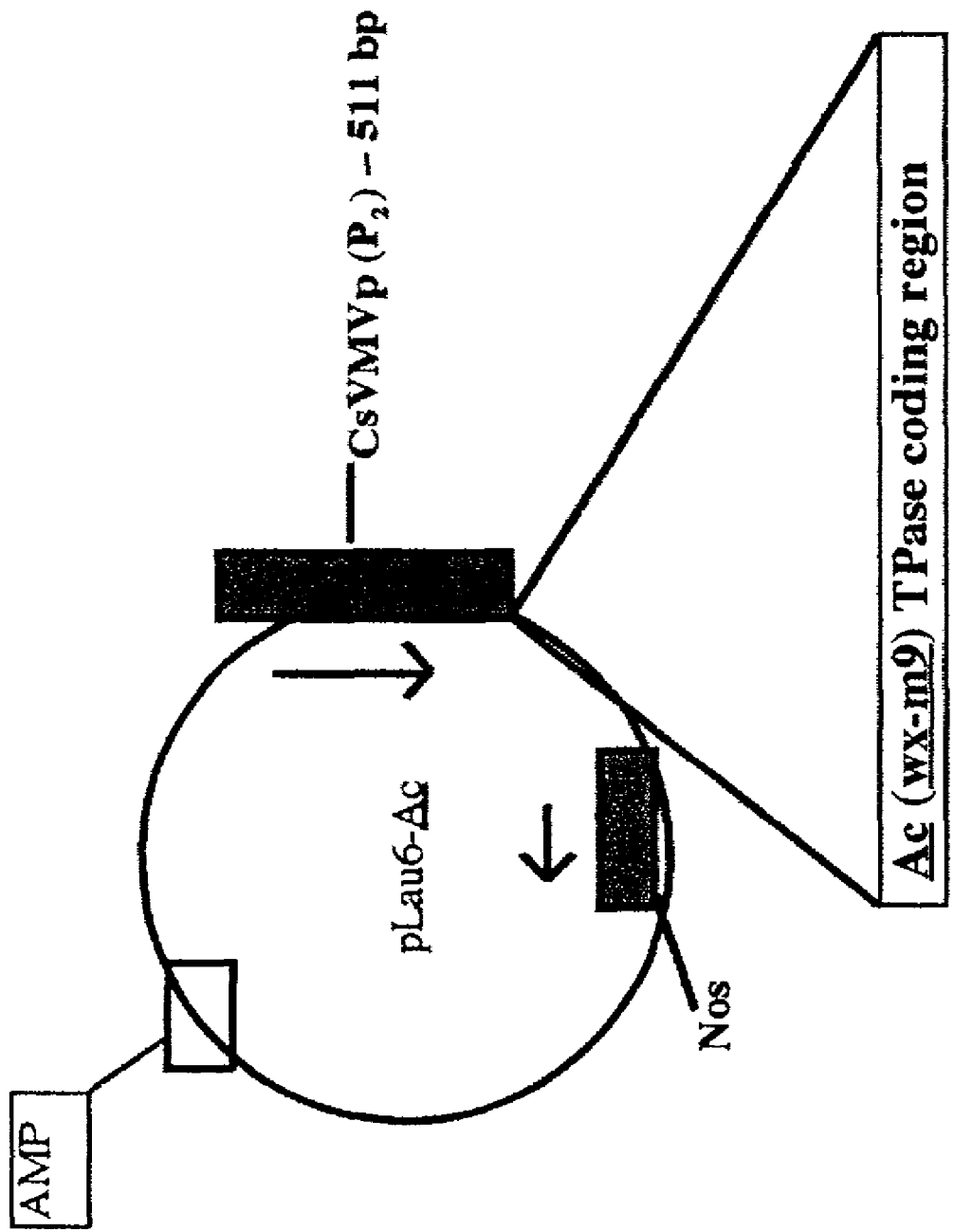
Figure 1 Part (B.)

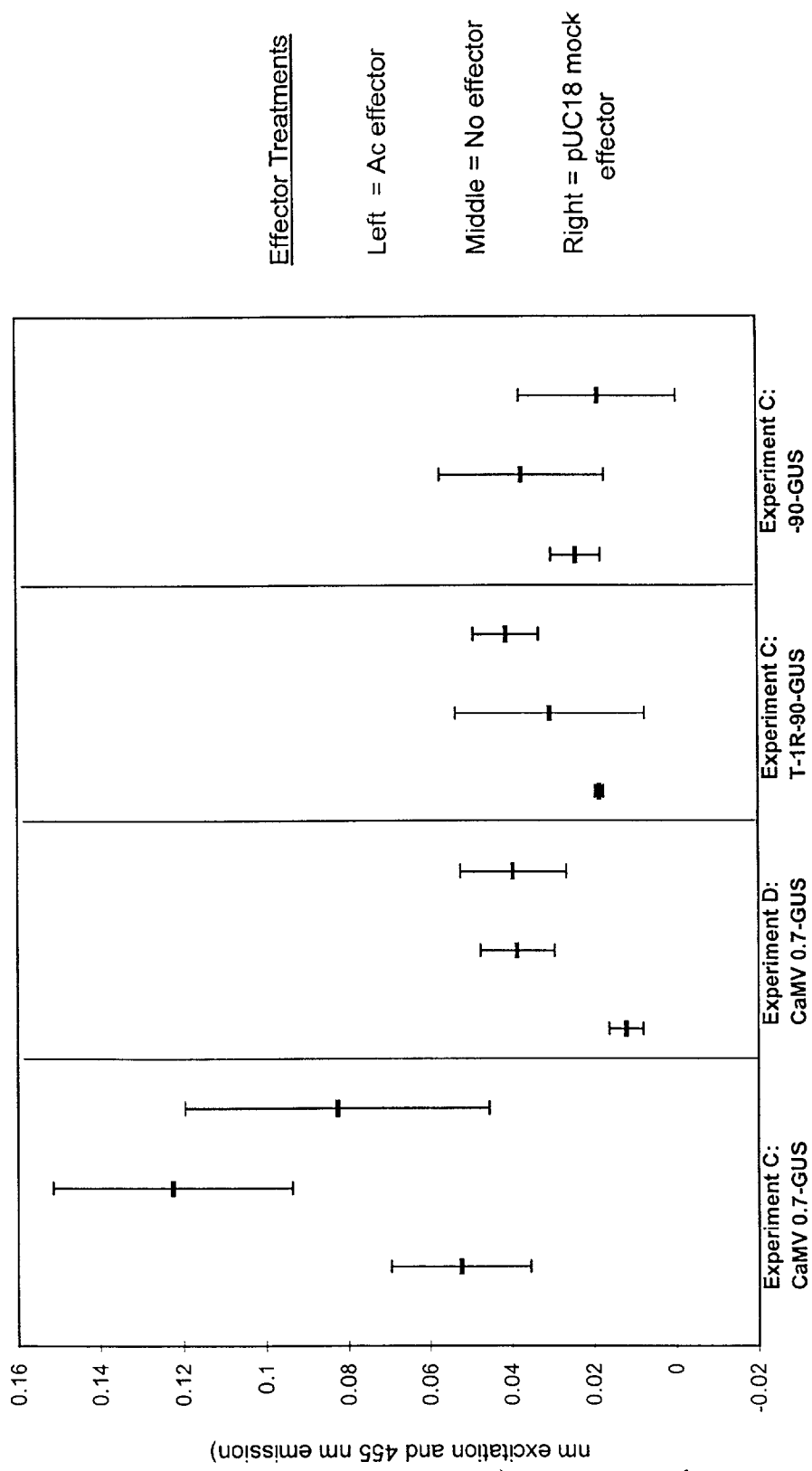

Figure 3.

CAGTCAAAAGATTCAGGACTAACTGCATCAAGAACACAGAGAAAG

ATATATTTCTCAAGATCAGAAGTACTATTCCAGTATGGACGATTCA

AGGCTTGCTTCATAAACCAAGGCAAGTAATAGAGATTGGAGTCTC

TAAGAAAGTAGTTCCTACTGAATCAAAGGCCATGGAGTCAAAAAT

TCAGATCGAGGATCTAACAGAACTCGCCGTGAAGACTGGCGAAC

AGTTCATACAGAGTCTTTTACGACTCAATGACAAGAAGAAAATCTT

CGTCAACATGGTGGAGCACGACACTCTCGTCTACTCCAAGAATAT

CAAAGATACAGTCTCAGAAGACCAAAGGGCTATTGAGACTTTTCA

ACAAAGGGTAATATCGGGAAACCTCCTCGGATTCCATTGCCCAGC

TATCTGTCACTTCATCAAAAGGACAGTAGAAAAGGAAGGTGGCAC

CTACAAATGCCATCATTGCGATAAAGGAAAGGCTATCGTTCAAGA

TGCCTCTGCCGACAGTGGTCCCAAAGATGGACCCCCACCCACGA

GGAGCATCGTGGAAAAGAAGACGTTCCAACCACGTCTTCAAAGC

AAGTGGATTGATGTGATATCTCCACTGACGTAAGGGATGACGCAC
-90 Δ
AATCCCACTATCCTTCGCAAGACCCTTCCTCTATATAAGGAAGTTC

ATTTCATTTGGAGAGGACACGCTG +8

Figure 4. Outline of ELISA protocol.

Nickel metal coating on Elisa plate
⬇
A 6X Histidine-tagged recombinant protein, induced by galactose addition, is added to the plate (e.g., Ac TPase from maize, induced in yeast cells)
⬇ (washes)
A primary antibody (made in mice or rabbits) is added to the plate (e.g., a 1° antibody against the 6X HIS tag, against the Ac TPase N-terminal region, or, against the Ac TPase C-terminal region)
⬇ (washes)
A secondary antibody is added to the plate (i.e., an anti-rabbit or anti-mouse 2° antibody, conjugated to alkaline phosphatase, is added, appropriately)
⬇ (washes)
A PNPP substrate (see below for definition) is added to the plate; this is cleaved by alkaline phosphatase to yield a yellow product. The product is both visible to the eye and quantifiable at 405 nm, in a spectrophotometer.

SEQUENCE LISTING

<160> NUMBER OF SEQ ID NOS: 9

<210> SEQ ID NO 1
<211> LENGTH: 40
<212> TYPE: DNA
<213> ORGANISM: artificial sequence
<220> FEATURE:
<223> OTHER INFORMATION: primer

<400> SEQUENCE: 1
gataggaagc ttaaacggat ctccactgac gtaagggatg       40

<210> SEQ ID NO 2
<211> LENGTH: 23
<212> TYPE: DNA
<213> ORGANISM: artificial sequence
<220> FEATURE:
<223> OTHER INFORMATION: primer

<400> SEQUENCE: 2
gatttcacgg gttggggttt cta       23

<210> SEQ ID NO 3
<211> LENGTH: 34
<212> TYPE: DNA
<213> ORGANISM: artificial sequence
<220> FEATURE:
<223> OTHER INFORMATION: primer

<400> SEQUENCE: 3
gataggaagc ttatctccac tgacgtaagg gatg       34

<210> SEQ ID NO 4
<211> LENGTH: 30
<212> TYPE: DNA
<213> ORGANISM: artificial sequence
<220> FEATURE:
<223> OTHER INFORMATION: primer

<400> SEQUENCE: 4
ggaacccgga tcccacttcg gctagccggc       30

<210> SEQ ID NO 5
<211> LENGTH: 30
<212> TYPE: DNA
<213> ORGANISM: artificial sequence
<220> FEATURE:
<223> OTHER INFORMATION: primer

<400> SEQUENCE: 5

```
ggaacccgga tccaccaagg ctcatctgtc                                      30
```

<210> SEQ ID NO 6
<211> LENGTH: 4810
<212> TYPE: DNA
<213> ORGANISM: Zea mays

<400> SEQUENCE: 6

```
ctgcaggcgg aggtcgggct cccggtggac cggaacatcc cgctggtggc gttcatcggc     60
aggctggaag agcagaaggg ccccgacgtc atggcggccg ccatcccgca gctcatggag    120
atagggatga aacggtcgg taacggtcgg taaaatacct ctaccgtttt cattttcata    180
tttaacttgc gggacggaaa cgaaaacggg atataccggt aacgaaaacg aacgggataa    240
atacggtaat cgaaaaccga tacgatccgg tcgggttaaa gtcgaaatcg gacgggaacc    300 ggtattttg ttcggtaaaa tcacacatga aaacatatat tcaaaactta aaacaaata     360 taaaaattg taaacacaag tcttaattaa acatagataa aatccatata aatctggagc    420
acacatagtt taatgtagca cataagtgat aagtcttggg ctcttggcta acataagaag    480
ccatataagt ctactagcac acatgacaca atataaagtt taaaacacat attcataatc    540
acttgctcac atctggatca cttagcatgc ataaactatt acaaccaagg ctcatctgtc    600
aacaaacata agacacattg ctcatggaga ggagccactt gctacatctt cattattctt    660
agaaaattct attgcgtctt catcctgtta atacacaaaa ataagtcagt tttggataaa    720
taaatacata tagaagaaca tgaattgata tgcagggagt ataaataaat acatataggga    780 gaacatgaat ctgtgaacta acacggctgg gagctaggca gctagcagct agcgcctaac    840
agctgggagc ctaacagcta gcagctagca gccaatcaaa acaaggcgac aaggcgcatg    900
cagtgagatc aaaaatctgt taatgccagc catgcaggga gtataacacg gctgggcagc    960
aaggcgcatg catcaaaaca aggcgacaga caacagccca tgcatcaaaa cagtagtgaa   1020
taatagcaaa ttaatagccc atgcacgaag taaataataa tctttaaata cctcatccat   1080
atgattctca tgatttgttg cagcagcaat aacagagtct agcacctcga gatcaccaat   1140
cattgttgga aaatatgtag caccttgaat gacacaaata tgcatcaata taagtaaaat   1200
aattgttgaa taactataaa ttggaacttc attataacat atatgcattc acctttttcta   1260 gatgctgcta cccaatcttt tgtgcatatc aaagcttcaa caatctccga accaagacga   1320
ttgcggtaag gatcaacaac acgaccacca gcactgaacg cagactcaga agcaacagtt   1380
gacacttgta ttgctagcac atcccttgca atttgggtga aataggata ttctgcaacc    1440 cttcccctcc accatgataa aatatcaaac tgaccactat gcttcaaaag gggttcagac   1500
atatatttat ccaattcatt tgactctact tgatcaataa ccttcaactc atgcaaatag   1560
ttttgaaatt catcatcttc attttccatc aaggtatcat ccatactatc attagtagtt   1620
gtctttgtct ttggagctga aggactacaa ctagaataga attgatacaa ttttctaatg   1680
accctaacaa agtcatctac atgaactttg tatgaatcac catgaaattt tttcatatag   1740
```

-continued

```
aactcaatca atattttctt gtacctaggg tcaaggaagc atgctacagc tagtgcaata    1800
ttagacactt tccaatattt ctcaaacttt tcactcattg caacggccat tctcctaatg    1860 acaaatttt  catgaacaca ccattggtca atcaaatcct ttatctcaca gaaacctttg    1920
taaaataaat ttgcagtgga atattgagta ccagatagga gttcagtgag atcaaaaaac    1980
ttcttcaaac acttaaaaag agttaatgcc atcttccact cctcggcttt aggacaaatt    2040
gcatcgtacc tacaataatt gacatttgat taattgagaa tttataatga tgacatgtac    2100
aacaattgag acaaacatac ctgcgaggat cacttgtttt aagccttatt agtgcaggct    2160
tataatataa ggcatccctc aacatcaaat aggttgaatt ccatctagtt gagacatcat    2220
atgagatccc tttagattta tccaagtcac attcactagc acacttcatt agttcttccc    2280
actgcaaagg agaagatttt acagcaagaa caatcgcttt gattttctca attgttcctg    2340
caattacagc caagccatcc tttgcaacca agttcagtat gtgacaagca cacctcacat    2400
gaaagaaagc accatcacaa actagatttg aatcagtgtc ctgcaaatcc tcaattatat    2460
cgtgcacagc tacttcattt gcactagcat tatccaaaga caaggcaaac aattttttct    2520
caatgttcca cttaaccatg attgcagtga aggtttgtga taacctttgg ccagtgtggc    2580
gcccttcaac atgaaaaaag ccaacaattc ttttttggag acaccaatca tcatcaatcc    2640
aatggatggt gacacacatg tatgacttat tttgacaaga tgtccacata tccatagttg    2700
tactgaagcg agactgaaca tcttttagtt ttccatacaa cttttctttt tcttccaaat    2760
acaaatccat gatatatttt ctagcagtga cacgggactt tattggaaag tgagggcgca    2820
gagacttaac aaactcaaca aagtactcat gttctacaat attgaaagga tattcatgca    2880
tgattattgc caaatgaagc ttctttaggc taaccacttc atcgtactta taaggctcaa    2940
tgagatttat gtcttttgcca tgatcctttt cacttttttag acacaactga cctttaacta    3000
aactatgtga tgttctcaag tgatttcgaa atccgcttgt tccatgatga ccctcagccc    3060
tatacttagc cttgcaatta ggaaagttgc aatgtcccca tacctgaacg tatttctttc    3120
catcgacctc cacttcaatt tccttcttgg tgaaatgctg ccatacatcc gatgtgcact    3180
tctttgccct cttctgtggt gcttcttctt cgggttcagg ttgtggctgt ggttgtggtt    3240
ctggttgtgg ttgtggttgt ggttgtggtt catgaacaat agccatatca tcttgactcg    3300
gatctgtagc tgtaccatt  gcattactac tgcttacact ctgaataaaa tgcctctcgg    3360
cctcagctgt tgatgatgat ggtgatgtgc ggccacatcc atgcccacgc gcacgtgcac    3420
gtacattctg aatccgacta gaaggctcta gcttttcttt tcaaccctgt tataaacaga    3480 ttttcgtat  tattctacag tcaatatgat gcttcccaat ctacaaccaa ttagtaatgc    3540
taatgctatt gctactgttt ttctaatata taccttgagc atatgcagag aatacggaat    3600
ttgttttgcg agtagaaggc gctcttgtgg tagacatcaa cttggccaat cttatggctg    3660
agcctgaggg aggattattt ccaaccggag gcgtcatctg aggaatggag tcgtagccgg    3720
ctagccgaag tggagagcag agccctggac agcaggtgtt cagcaatcag cttggtgctg    3780
tactgctgtg acttgtgagc acctggacgg ctggacagca atcagcaggt gttgcagagc    3840
ccctggacag cacacaaatg acacaacagc ttggtgcaat ggtgctgacg tgctgtactg    3900
ctaagtgctg tgagcctgtg agcagccgtg agacaggga ccgcgcggat ggccggatgg    3960
gcgagcgccg agcagtggag gtctggagga ccgctgaccg cagatggcgg atggcggatg    4020
ggcggaccgc ggatgggcga gcagtggagt ggaggtctgg gcggatgggc ggaccgcggc    4080
gcggatgggc gagtcgcgag cagtggagtg gagggcggac cgtggatggc ggcgtctgcg    4140
```

-continued

```
tccggcgtgc cgcgtcacgg ccgtcaccgc gtgtggtgcc tggtgcagcc cagcggccgg   4200
ccggctggga gacagggaga gtcggagaga gcaggcgaga gcgagacgcg cgtcggcgtc   4260
ggcgtgcggc tggcggcgtc cggactccgg cgtgggcgcg tggcggcgtg tgaatgtgtg   4320
atgctgttac tcgtgtggtg cctgccgcct gggagagagg cagagcagcg ttcgctaggt   4380
atttcttaca tgggctgggc ctcagtggtt atggatggga gttggagctg gccatattgc   4440
agtcatcccg aattagaaaa tacggtaacg aaacgggatc atcccgatta aaacgggat   4500 cccggtgaaa cggtcgggaa actagctcta ccgtttccgt ttccgtttac cgttttgtat   4560
atcccgtttc cgttccgttt cgttttttta cctcgggttc gaaatcgatc gggataaaac   4620
taacaaaatc ggttatacga taacggtcgg tacgggattt tcccatccta ctttcatccc   4680
tgcatggaga tggtggagga cgtgcagatc gttctgctgg tacgtgtgcg ccgcccgcca   4740
cccggctact acatgcgtgt atcgttctac tggaacatac gtgtgagcaa cgcgatggat   4800
aatgctgcag                                                          4810
```

<210> SEQ ID NO 7
<211> LENGTH: 807
<212> TYPE: PRT
<213> ORGANISM: Zea mays

<400> SEQUENCE: 7

```
Met Thr Pro Pro Val Gly Asn Asn Pro Pro Gly Ser Ala Ile Arg
1               5                  10                  15

Leu Ala Lys Leu Met Ser Thr Thr Arg Ala Pro Ser Thr Arg Lys Thr
                20                  25                  30

Asn Ser Val Phe Ser Ala Tyr Ala Gln Gly Leu Lys Arg Lys Ala Glu
            35                  40                  45

Ala Ser Ser Ser Arg Ile Gln Asn Val Arg Ala Arg Ala Arg Gly His
        50                  55                  60

Gly Cys Gly Arg Thr Ser Pro Ser Ser Thr Ala Glu Ala Glu Arg
65                  70                  75                  80

His Phe Ile Gln Ser Val Ser Ser Ser Asn Ala Asn Gly Thr Ala Thr
                85                  90                  95

Asp Pro Ser Gln Asp Asp Met Ala Ile Val His Glu Pro Gln Pro Gln
            100                 105                 110

Pro Gln Pro Gln Pro Glu Pro Gln Pro Gln Pro Gln Pro Glu Pro Glu
        115                 120                 125

Glu Glu Ala Pro Gln Lys Arg Ala Lys Lys Cys Thr Ser Asp Val Trp
    130                 135                 140

Gln His Phe Thr Lys Lys Glu Ile Glu Val Glu Val Asp Gly Lys Lys
145                 150                 155                 160

Tyr Val Gln Val Trp Gly His Cys Asn Phe Pro Asn Cys Lys Ala Lys
                165                 170                 175

Tyr Arg Ala Glu Gly His His Gly Thr Ser Gly Phe Arg Asn His Leu
            180                 185                 190

Arg Thr Ser His Ser Leu Val Lys Gly Gln Leu Cys Leu Lys Ser Glu
        195                 200                 205

Lys Asp His Gly Lys Asp Ile Asn Leu Ile Glu Pro Tyr Lys Tyr Asp
    210                 215                 220

Glu Val Val Ser Leu Lys Lys Leu His Leu Ala Ile Ile Met His Glu
225                 230                 235                 240
```

```
Tyr Pro Phe Asn Ile Val Glu His Glu Tyr Phe Val Glu Phe Val Lys
                245                 250                 255
Ser Leu Arg Pro His Phe Pro Ile Lys Ser Arg Val Thr Ala Arg Lys
                260                 265                 270
Tyr Ile Met Asp Leu Tyr Leu Glu Glu Lys Glu Lys Leu Tyr Gly Lys
                275                 280                 285
Leu Lys Asp Val Gln Ser Arg Phe Ser Thr Thr Met Asp Met Trp Thr
        290                 295                 300
Ser Cys Gln Asn Lys Ser Tyr Met Cys Val Thr Ile His Trp Ile Asp
305                 310                 315                 320
Asp Asp Trp Cys Leu Gln Lys Arg Ile Val Gly Phe Phe His Val Glu
                325                 330                 335
Gly Arg His Thr Gly Gln Arg Leu Ser Gln Thr Phe Thr Ala Ile Met
                340                 345                 350
Val Lys Trp Asn Ile Glu Lys Lys Leu Phe Ala Leu Ser Leu Asp Asn
                355                 360                 365
Ala Ser Ala Asn Glu Val Ala Val His Asp Ile Ile Glu Asp Leu Gln
        370                 375                 380
Asp Thr Asp Ser Asn Leu Val Cys Asp Gly Ala Phe Phe His Val Arg
385                 390                 395                 400
Cys Ala Cys His Ile Leu Asn Leu Val Ala Lys Asp Gly Leu Ala Val
                405                 410                 415
Ile Ala Gly Thr Ile Glu Lys Ile Lys Ala Ile Val Leu Ala Val Lys
                420                 425                 430
Ser Ser Pro Leu Gln Trp Glu Glu Leu Met Lys Cys Ala Ser Glu Cys
        435                 440                 445
Asp Leu Asp Lys Ser Lys Gly Ile Ser Tyr Asp Val Ser Thr Arg Trp
        450                 455                 460
Asn Ser Thr Tyr Leu Met Leu Arg Asp Ala Leu Tyr Tyr Lys Pro Ala
465                 470                 475                 480
Leu Ile Arg Leu Lys Thr Ser Asp Pro Arg Arg Tyr Asp Ala Ile Cys
                485                 490                 495
Pro Lys Ala Glu Glu Trp Lys Met Ala Leu Thr Leu Phe Lys Cys Leu
                500                 505                 510
Lys Lys Phe Phe Asp Leu Thr Glu Leu Leu Ser Gly Thr Gln Tyr Ser
        515                 520                 525
Thr Ala Asn Leu Phe Tyr Lys Gly Phe Cys Glu Ile Lys Asp Leu Ile
        530                 535                 540
Asp Gln Trp Cys Val His Glu Lys Phe Val Ile Arg Arg Met Ala Val
545                 550                 555                 560
Ala Met Ser Glu Lys Phe Glu Lys Tyr Trp Lys Val Ser Asn Ile Ala
                565                 570                 575
Leu Ala Val Ala Cys Phe Leu Asp Pro Arg Tyr Lys Lys Ile Leu Ile
                580                 585                 590
Glu Phe Tyr Met Lys Lys Phe His Gly Asp Ser Tyr Lys Val His Val
        595                 600                 605
Asp Asp Phe Val Arg Val Ile Arg Lys Leu Tyr Gln Phe Tyr Ser Ser
        610                 615                 620
Cys Ser Pro Ser Ala Pro Lys Thr Lys Thr Thr Thr Asn Asp Ser Met
625                 630                 635                 640
Asp Asp Thr Leu Met Glu Asn Glu Asp Asp Glu Phe Gln Asn Tyr Leu
                645                 650                 655
```

-continued

| | | | | | | | | | | | | |
|---|---|---|---|---|---|---|---|---|---|---|---|---|
|His|Glu|Leu|Lys|Asp|Tyr|Asp|Gln|Val|Glu|Ser|Asn|Glu|Leu|Asp|Lys|
| | | |660| | | |665| | | |670| | | |
|Tyr|Met|Ser|Glu|Pro|Leu|Leu|Lys|His|Ser|Gly|Gln|Phe|Asp|Ile|Leu|
| | | |675| | | |680| | | |685| | | |
|Ser|Trp|Trp|Arg|Gly|Arg|Val|Ala|Glu|Tyr|Pro|Ile|Leu|Thr|Gln|Ile|
| | | |690| | | |695| | | |700| | | |
|Ala|Arg|Asp|Val|Leu|Ala|Ile|Gln|Val|Ser|Thr|Val|Ala|Ser|Glu|Ser|
|705| | | |710| | | |715| | | |720| | | |
|Ala|Phe|Ser|Ala|Gly|Gly|Arg|Val|Val|Asp|Pro|Tyr|Arg|Asn|Arg|Leu|
| | | |725| | | |730| | | |735| | | |
|Gly|Ser|Glu|Ile|Val|Glu|Ala|Leu|Ile|Cys|Thr|Lys|Asp|Trp|Val|Ala|
| | | |740| | | |745| | | |750| | | |
|Ala|Ser|Arg|Lys|Gly|Ala|Thr|Tyr|Phe|Pro|Thr|Met|Ile|Gly|Asp|Leu|
| | | |755| | | |760| | | |765| | | |
|Glu|Val|Leu|Asp|Ser|Val|Ile|Ala|Ala|Ala|Thr|Asn|His|Glu|Asn|His|
| | | |770| | | |775| | | |780| | | | |
|Met|Asp|Glu|Asp|Glu|Asp|Ala|Ile|Glu|Phe|Ser|Lys|Asn|Asn|Glu|Asp|
|785| | | |790| | | |795| | | |800| | | |
|Val|Ala|Ser|Gly|Ser|Ser|Pro|
| | | |805| | | |

<210> SEQ ID NO 8
<211> LENGTH: 4565
<212> TYPE: DNA
<213> ORGANISM: Zea mays

<400> SEQUENCE: 8

```
cagggatgaa agtaggatgg gaaaatcccg taccgaccgt tatcgtataa ccgattttgt      60
tagttttatc ccgatcgatt tcgaacccga ggtaaaaaac gaaaacggaa cggaaacggg     120
atatacaaaa cggtaaacgg aaacggaaac ggtagagcta gtttcccgac cgtttcaccg     180
ggatcccgtt tttaatcggg atgatcccgt ttcgttaccg tattttctaa ttcgggatga     240
ctgcaatatg gccagctcca actcccatcc ataaccactg aggcccagcc catgtaagaa     300
ataccctagcg aacgctgctc tgcctctctc ccaggcggcc aggcaccaca cgagtaacag     360
catcacacat tcacacgccg ccacgcgccc acgccggagt ccggacgccg ccagccgcac     420
gccgacgccg gcgacgcgtc tcgctctcgc ctgctctctc cgactctccc tgtctcccag     480
ccggccggcc gctgggctgc accaggcacc acacgcggtg acggccgtga cgcggcacgc     540
cggacgcaga cgccgccatc cacggtccgc cctccactcc actgctcgcg actcgcccat     600
ccgcgccgcg gtccgcccat ccgcccgac ctccactcca ctgctcgccc atccgcggtc     660
cgcccatccg ccatccgcca tctgcggtca gcggtcctcc agacctccac tgctcggcgc     720
tcgcccatcc ggccatccgc ggtctccctg tctccacggc tgctcacagg ctcacagcac     780
ttagcagtac agcacgtcag caccattgca ccaagctgtt gtgtcatttg tgtgctgtcc     840
agggctctg caacacctgc tgattgctgt ccagccgtcc aggtgctcac aagtcacagc     900
agtacagcac caagctgatt gctgaacacc tgctgtccag ggctctgctc tccacttcgg     960
ctagccggct acgactccat tcctcagatg acgcctccgg ttggaaataa tcctccctca    1020
ggctcagcca taagattggc caagttgatg tctaccacaa gagcgccttc tactcgcaaa    1080
acaaattccg tattctctgc atatgctcaa ggtatatatt agaaaaacag tagcaatagc    1140
attagcatta ctaattggtt gtagattggg aagcatcata ttgactgtag aataatacga    1200
aaaatctgtt tataacaggg ttgaaaagaa aagctgaagc ctcttctagt cggattcaga    1260
```

-continued

```
atgtacgtgc acgtgcgcgt gggcatggat gtggccgcac atcaccatca tcatcaacag    1320
ctgaggccga gaggcatttt attcagagtg taagcagtag taatgcaaat ggtacagcta    1380
cagatccgag tcaagatgat atggctattg ttcatgaacc acaaccacaa ccacaaccac    1440
aaccagaacc acaaccacag ccacaacctg aacccgaaga agaagcacca cagaagaggg    1500
caaagaagtg cacatcggat gtatggcagc atttcaccaa gaaggaaatt gaagtggagg    1560
tcgatggaaa gaaatacgtt caggtatggg acattgcaa cttttcctaat tgcaaggcta    1620 agtatagggc tgagggtcat catggaacaa gcggatttcg aaatcacttg agaacatcac    1680
atagtttagt taaaggtcag ttgtgtctaa aaagtgaaaa ggatcatggc aaagacataa    1740
atctcattga gccttataag tacgatgaag tggttagcct aaagaagctt catttggcaa    1800
taatcatgca tgaatatcct ttcaatattg tagaacatga gtactttgtt gagtttgtta    1860
agtctctgcg ccctcacttt ccaataaagt cccgtgtcac tgctagaaaa tatatcatgg    1920
atttgtattt ggaagaaaaa gaaaagttgt atggaaaact aaaagatgtt cagtctcgct    1980
tcagtacaac tatggatatg tggacatctt gtcaaaataa gtcatacatg tgtgtcacca    2040
tccattggat tgatgatgat tggtgtctcc aaaaaagaat tgttggcttt tttcatgttg    2100
aagggcgcca cactggccaa aggttatcac aaaccttcac tgcaatcatg gttaagtgga    2160
acattgagaa aaaattgttt gccttgtctt tggataatgc tagtgcaaat gaagtagctg    2220
tgcacgatat aattgaggat ttgcaggaca ctgattcaaa tctagtttgt gatggtgctt    2280
tctttcatgt gaggtgtgct tgtcacatac tgaacttggt tgcaaaggat ggcttggctg    2340
taattgcagg aacaattgag aaaatcaaag cgattgttct tgctgtaaaa tcttctcctt    2400
tgcagtggga agaactaatg aagtgtgcta gtgaatgtga cttggataaa tctaaaggga    2460
tctcatatga tgtctcaact agatggaatt caacctattt gatgttgagg gatgccttat    2520
attataagcc tgcactaata aggcttaaaa caagtgatcc tcgcaggtat gtttgtctca    2580
attgttgtac atgtcatcat tataaattct caattaatca aatgtcaatt attgtaggta    2640
cgatgcaatt tgtcctaaag ccgaggagtg gaagatggca ttaactcttt ttaagtgttt    2700
gaagaagttt tttgatctca ctgaactcct atctggtact caatattcca ctgcaaattt    2760
attttacaaa ggtttctgtg agataaagga tttgattgac caatggtgtg ttcatgaaaa    2820
atttgtcatt aggagaatgg ccgttgcaat gagtgaaaag tttgagaaat attggaaagt    2880
gtctaatatt gcactagctg tagcatgctt ccttgaccct aggtacaaga aaatattgat    2940
tgagttctat atgaaaaaat ttcatggtga ttcatacaaa gttcatgtag atgactttgt    3000
tagggtcatt agaaaattgt atcaattcta ttctagttgt agtccttcag ctccaaagac    3060
aaagacaact actaatgata gtatggatga taccttgatg gaaaatgaag atgatgaatt    3120
tcaaaactat ttgcatgagt tgaaggatta tgatcaagta gagtcaaatg aattggataa    3180
atatatgtct gaaccccttt tgaagcatag tggtcagttt gatatttat catggtggag    3240 gggaagggtt gcagaatatc ctattctcac ccaaattgca agggatgtgc tagcaataca    3300
agtgtcaact gttgcttctg agtctgcgtt cagtgctggt ggtcgtgttg ttgatcctta    3360
ccgcaatcgt cttggttcgg agattgttga agctttgata tgcacaaaag attgggtagc    3420
agcatctaga aaaggtgaat gcatatatgt tataatgaag ttccaatttta tagttattca    3480 acaattattt tacttatatt gatgcatatt tgtgtcattc aaggtgctac atattttcca    3540
acaatgattg gtgatctcga ggtgctagac tctgttattg ctgctgcaac aaatcatgag    3600
```

-continued

```
aatcatatgg atgaggtatt taaagattat tatttacttc gtgcatgggc tattaatttg    3660
ctattattca ctactgtttt gatgcatggg ctgtttgctg tcgccttgtt ttgatgcatg    3720
cgccttgctg cccagccgtg ttatactccc tgcatggctg gcattaacag atttttgatc    3780
tcactgcatg cgccttgtcg ccttgttttg attggctgct agctgctagc tgttaggctc    3840
ccagctgtta ggcgctagct gctagctgcc tagctcccag ccgtgttagt tcacagattc    3900
atgttctcct atatgtattt atttatactc cctgcatatc aattcatgtt cttctatatg    3960
tatttattta tccaaaactg acttattttt gtgtattaac aggatgaaga cgcaatagaa    4020
ttttctaaga ataatgaaga tgtagcaagt ggctcctctc catgagcaat gtgtcttatg    4080
tttgttgaca gatgagcctt ggttgtaata gtttatgcat gctaagtgat ccagatgtga    4140
gcaagtgatt atgaatatgt gttttaaact ttatattgtg tcatgtgtgc tagtagactt    4200
atatggcttc ttatgttagc caagagccca agacttatca cttatgtgct acattaaact    4260
atgtgtgctc cagatttata tggatttat ctatgtttaa ttaagacttg tgtttacaat    4320
tttttatatt tgttttaag ttttgaatat atgttttcat gtgtgatttt accgaacaaa    4380
aataccggtt cccgtccgat ttcgacttta acccgaccgg atcgtatcgg ttttcgatta    4440
ccgtatttat cccgttcgtt ttcgttaccg gtatatcccg ttttcgtttc cgtcccgcaa    4500
gttaaatatg aaaatgaaaa cggtagaggt attttaccga ccgttaccga ccgttttcat    4560
cccta                                                                4565
```

<210> SEQ ID NO 9
<211> LENGTH: 700
<212> TYPE: DNA
<213> ORGANISM: Cauliflower mosaic virus

<400> SEQUENCE: 9

```
cagtcaaaag attcaggact aactgcatca agaacacaga gaaagatata tttctcaaga     60
tcagaagtac tattccagta tggacgattc aaggcttgct tcataaacca aggcaagtaa    120
tagagattgg agtctctaag aaagtagttc ctactgaatc aaaggccatg gagtcaaaaa    180
ttcagatcga ggatctaaca gaactcgccg tgaagactgg cgaacagttc atacagagtc    240
ttttacgact caatgacaag aagaaaatct tcgtcaacat ggtggagcac gacactctcg    300
tctactccaa gaatatcaaa gatacagtct cagaagacca aagggctatt gagactttc    360 aacaaagggt aatatcggga aacctcctcg gattccattg cccagctatc tgtcacttca    420
tcaaaaggac agtagaaaag gaaggtggca cctacaaatg ccatcattgc gataaaggaa    480
aggctatcgt tcaagatgcc tctgccgaca gtggtcccaa agatggaccc ccacccacga    540
ggagcatcgt ggaaaaagaa gacgttccaa ccacgtcttc aaagcaagtg gattgatgtg    600
atatctccac tgacgtaagg gatgacgcac aatcccacta tccttcgcaa gacccttcct    660
ctatataagg aagttcattt catttggaga ggacacgctg                          700
```

USE OF TRANSPOSABLE ELEMENTS FOR ALTERING GENE EXPRESSION

CROSS-REFERENCE TO RELATED APPLICATION

This application claims the benefit of U.S. Provisional Application No. 60/287,882, filed May 1, 2001.

BACKGROUND OF THE INVENTION (1) Field of the Invention

The present invention generally relates to methods of altering gene expression. More specifically, the invention relates to methods of altering gene expression using transposons.

(2) Description of the Related Art

REFERENCES CITED

Agrawal et al., 1998, Nature 394: 744–751.
Alatortsev et al., 2000, Russian Journal of Genetics 36: 509–513.
Altpeter et al., 1996, Nature Biotechnology 14: 1155–1159.
Amae et al., 2000, Biochim. Biophys. Acta 1492: 505–508.
Amber, 2000, The Scientist, Oct. 30th issue: 18.
Amrein et al., 1994, Cell 76: 735–746.
Angelov et al., 2000, Journal of Mol. Biol. 302: 315–326.
Aravind, 2000, Trends in Biochem. Sci. 25: 421–423.
Argaman and Altuvia, 2000, Journal of Mol. Biol. 300: 1101–1112.
Arnold et al., 2000, Gene 253: 209–214.
Arthur et al., 2001, Journal Virol. 75: 3885–3895.
Baker et al., 1988, Plant Mol. Biol. 11: 277–291.
Balazs et al., 1982, Gene 19: 239–249.
Barcelo et al., 1994, Plant Journal 5: 583–592.
Bash and Lohr, 2000, Prog. Nucleic Acid Res. Mol. Biol. 65: 197–259.
Baum et al., 1999, FEBS Letters 454: 95–99.
Beato, 1989, Cell 56: 335–344.
Becker and Kunze, 1996, Mol. Gen. Genet. 251: 428–435.
Becker and Kunze, 1997, Mol. Gen. Genet. 254: 219–230.
Becker et al., 1992, Plant Mol. Biol. 20: 49–60.
Behrens et al., 1984, Mol. Gen. Genet. 194: 346–347.
Benfey et al., 1990a, EMBO Journal 9: 1677–1684.
Benfey et al., 1990b, EMBO Journal 9: 1685–1696.
Benito and Walbot, 1997, Mol. Cell Biol. 17: 5165–5175.
Bhattacharyya-Pakrasi et al., 1993, Plant Journal 4: 71–79.
Blechl and Anderson, 1996, Nat. Biotechnol. 14: 875–879.
Borkowska et al., 1998, Z. Naturforsch [C] 53: 1012–1016.
Brehm et al., 1999, Z. Naturforsch [C] 54: 220–229.
Brunke and Wilson, European Patent Publication #0 559 603 A2, published Sep. 8, 1993.
Brutnell and Dellaporta, 1994, Genetics 138: 213–225.
Bult et al., 1996, Science 273: 1058–1073.
Bustos et al., 1991, EMBO Journal 10: 1469–1479.
Carroll et al., 1995, Genetics 139: 407–420.
Catteruccia et al., 2000, Proc. Natl. Acad. Sci. USA 97: 2157–2162.
Chaboute et al., 2000, Plant Cell 12: 1987–2000.
Chalfie, 1995, Photochem. Photobiol. 62: 651–656.
Charng et al., 2000, Mol. Breeding 6: 353–367.
Chaure et al., 2000, Nat. Biotechnol. 18: 205–207.
Chen et al., 1987, Genetics 117: 109–116.
Chernukhin et al., 2000, Journal Biol. Chem. 275: 29915–29921.
Cho et al., 1999, Proc. Natl. Acad. Sci. USA 96: 14641–14646.
Chomet et al., 1987, EMBO Journal 6: 295–302.
Chowrira et al., 1995, Mol. Biotechnol. 3: 17–23.
Christianson and Kafatos, 1993, Biochem. Biophys. Res. Commun. 193: 1318–1323.
Chung et al., 1999, Cancer Res. 59: 4610–4617.
Comfort, 1999, Journal of the History of Biology 32: 133–162.
Cordes et al., 1989, Plant Cell 1: 1025–1034.
Cornejo et al., 1993, Plant Mol. Biol. 23: 567–581.
Dahl et al., 2000, Microbiol. 146: 1469–1479.
Davies et al., 2000, Science 289: 77–85.
DeBosscher et al., 2000, Neuroimmunol. 109: 16–22.
Deikman et al., 1998, Plant Mol. Biol. 37: 1001–1011.
Delattre et al., 2000, Mol. Gen. Genet. 263: 445–454.
Deng and Brodie, 2000, Bioessays 22: 728–737.
Denisenko et al., 1996, Journal Biol. Chem. 271: 27701–27706.
DeVit and Johnston, 1999, Curr. Biol. 9: 1231–1241.
Dure et al., 1989, Plant Mol. Biol. 12: 475–486.
Duval et al., 2000, Cancer Res. 60: 3872–3879.
Ealing et al., 1994, Transgenic Res. 3: 344–354.
Elomaa et al., 1995, Mol. Gen. Genet. 248: 649–656.
Eriksson et al., 2000, Mol. Cell Biol. Res. Commun. 3: 292–298.
Essers et al., 2000, Plant Cell 12: 211–224.
Fafournoux et al., 2000, Biochem. Journal 351: 1–12.
Falco et al., 1995, Biotechnology 13: 577–582.
Fedoroff, 1999, Genes Cells 4: 11–19.
Fedoroff et al., 1983, Cell 35: 235–242.
Fedoroff et al., 1984, Proc. Natl. Acad. Sci. USA 81: 3825–3829.
Feschotte and Mouches, 2000, Mol. Biol. Evol. 17: 730–737.
Finer and Finer, 2000, Lett. Appl. Microbiol. 30: 406–410.
Fitzmaurice et al., 1999, Genetics 153: 1919–1928.
Fleischmann et al., 1995, Science 269: 496–512.
Fouts et al., 1997, Nucleic Acids Res. 25: 4464–4473.
Fraley et al., U.S. Pat. No. 5,352,605, issued on Oct. 4, 1994.
Fraser et al., 1995, Science 270: 397–403.
Fridlender M. et al., 1996, The Plant Journal 9:911–917.
Fridlender et al., 1998, Mol. Gen. Genet. 258: 306–314.
Fromm et al., 1986, Nature 319: 791–793.
Furusawa et al., 1999, Mol. Cell Biol. 19: 8581–8590.
Gallia et al., 2000, Nucleic Acids Res. 28: 3197–3205.
Garrick et al., 1998, Nat. Genet. 18: 56–59.
Geffers et al., 2000, Plant Mol. Biol. 43: 11–21.
Good et al., 1994, Plant Mol. Biol. 26: 781–790.
Goto et al., 1999, Nat. Biotechnol. 17: 282–286.
Govantes et al., 2000, Mol. Microbiol. 37: 1456–1469.
Gowri et al., 1991, Plant Mol. Biol. 17: 415–429.
Grichko et al., 2000, Journal Biotechnol. 81: 45–53.
Guilley et al., 1982, Cell 30: 763–773.
Hagenbeek et al., 2000, Plant Physiol. 123: 1553–1560.
Haider et al., 1986, Eur. Journal Biochem. 156: 531–540.
Han et al., 2000, Genes Genet. Syst. 75: 69–77.
Handler and Harrell, 1999, Insect Mol. Biol. 8: 449–457.
Harada et al., 1989, Plant Mol. Biol. 12: 395–401.
Hedley et al., 2000, Journal Exp. Bot. 51: 817–821.
Heifetz, 2000, Biochimie 82: 655–666.
Heinlein et al., 1998, Plant Cell 10: 1107–1120.
Henrich et al., 1990, Nucleic Acids Res. 18: 4143–4148.
Hofmann et al., 1988, Proc. Natl. Acad. Sci. USA 85: 7844–7848.
Hong et al., 1988, Plant Mol. Biol. 11: 495–506.
Hua et al., 1999, FEBS Letters 458: 193–196.

Hughes and Galau, 1991, Plant Cell 3: 605–618.
International Human Genome Sequencing Consortium, 2001, Nature 409: 860–921.
Izawa et al., 1997, Plant Mol. Biol. 35: 219–229.
Jasinskiene et al., 2000, Insect Mol. Biol. 9: 11–18.
Jefferson, 1987, Plant. Mol. Biol. Reporter 5: 387–405.
Jefferson et al., 1987, EMBO Journal 6: 3901–3907.
Jimenez et al., 1999, Mol. Cell Biol. 19: 2080–2087.
Johns et al., 1985, EMBO Journal 4: 1093–1102.
Juszczuk et al., 2000, FEBS Letters 484: 33–36.
Kastaniotis et al., 2000, Mol. Cell Biol. 20: 7088–7098.
Keller et al., 2000, Mol. Cell Biol. 20: 7247–7258.
Keller et al., 2001, Journal Virol. 75: 3993–3998.
Kempken and Kuck, 2000, Mol. Gen. Genet. 263: 302–308.
Keown et al., 1990, Methods Enzymol. 185: 527–536.
Kholodii et al., 2000, Genetika 36: 459–469.
Kipling and Warburton, 1997, Trends Genet. 13: 141–145.
Kishi et al., 2000, Blood 95: 3845–3852.
Kleinbaum et al. (eds.), 1988, Applied Regression Analysis and Other Multivariable Methods, 2nd ed., p. 32, Duxbury Press, Belmont, Calif.
Klinakis et al., 2000a, Insect Mol. Biol. 9: 269–275.
Klinakis et al., 2000b, EMBO Reports 1: 416–421.
Koelle et al., 1991, Cell 67: 59–77.
Koloteva et al., 1997, Journal Biol. Chem. 272: 16531–16539.
Kunze et al., 1987, EMBO Journal 6: 1555–1563.
Kunze et al., 1997, In: Callow (ed) Advances in Botanical Research, vol. 27: 331–470, Academic Press, New York, N.Y.
Lachmann and Efstathiou, 1999, Curr. Opin. Mol. Ther. 1: 622–632.
Laurin et al., 2000, Mamm. Genome 11: 972–978.
Lawley et al., 2000, Plasmid 43: 235–239.
Le et al., 2000, Proc. Natl. Acad. Sci. USA 97: 7376–7381.
Lebedev and Dolgov, 2000, Genetika 36: 792–798.
Lechner et al., 2000a, Nucleic Acids Res. 28: 2741–2751.
Lechner et al., 2000b, Mol. Cell Biol. 20: 6449–6465.
Leisner and Gelvin, 1988, Proc. Natl. Acad. Sci. USA 85: 2553–2557.
Lepetit et al., 2000, Genetica 108: 163–169.
Li et al., 1997, Plant Physiol. 114: 1103–1111.
Li et al., 1998, Somat. Cell Mol. Genet. 24: 363–369.
Lim et al., 1994, Journal Biol. Chem. 269: 9006–9010.
Lloyd et al., 1994, Science 266: 436–439.
Long et al., 1993, Mol. Gen. Genet. 241: 627–636.
Ludewig and Sonnewald, 2000, FEBS Letters 479: 19–24.
Luo and Farrand, 1999, Proc. Natl. Acad. Sci. USA 96: 9009–9014.
Luo et al., 2000, Proc. Natl. Acad. Sci. USA 97: 10637–10642.
Lyznik et al., 1989, Plant Mol. Biol. 13: 151–161.
Maclean et al., 1998, Br. Journal Biomed. Sci. 55: 184–191.
MacRae et al., 1999, Genetica 105: 19–29.
MacRae, 1999, NSF Submitted Grant Proposal Number 9986293, entitled "Flexible tools for regulating plant gene expression: utilization of the maize Activator transposable element system" (DUNS #044193006).
Manevski et al., 2000, FEBS Letters 483: 43–46.
Martusewitsch et al., 2000, Journal Bacteriol. 182: 2574–2581.
Marx, 2000, Science 288: 1370–1372.
Mathews and VanHolde, 1996, Biochemistry, 2nd ed., Benjamin/Cummings, Menlo Park, Calif.
Matzke et al., 2000, Plant Mol. Biol. 43: 401–415.
Medina and Joshi, 1999, Curr. Opin. Mol. Ther. 1: 580–594.
Mercie et al., 1998, Rev. Med. Interne. 19: 945–947.
Messeguer et al., 1991, Plant Mol. Biol. 16: 753–770.
Miller, 1972, Journal Virol. 10: 920–924.
Morrison et al., 1999, Nucleic Acids Res. 27: 1251–1262.
Mukhopadhyaya et al., 2000, Journal Bacteriol. 182: 4278–4287.
Muller-Neumann et al., 1984, Mol. Gen. Genet. 198: 19–24.
Mundy et al., 1990, Proc. Natl. Acad. Sci. USA 87: 1406–1410.
Muskens et al., 2000, Plant Mol. Biol. 43: 243–260.
Nagai et al., 2000, Journal Bacteriol. 182: 2387–2392.
Nakamura et al., 1998, Journal Hum. Genet. 43: 149–152.
Nakazato et al., 2000, Mol. Cell Biol. 20: 8499–8512.
Neely and Hoffman, 2000, Mol. Cell Biol. 20: 6426–6434.
Noury et al., 2000, Plant Mol. Biol. 43: 537–544.
Odell et al., 1985, Nature 313: 810–812.
Odell et al., 1987, Journal Cell Biochem. (Suppl. 11B): 60.
Odell et al., 1988, Plant Mol. Biol. 10: 263–272.
Okamuro et al., 1989, Biochemistry of Plants, vol. 15, pp. 1–82.
Oliver et al., 2000, Journal Mol. Biol. 301: 575–584.
Osbourn et al., 1989, Virol. 172: 370–373.
Ostareck-Lederer et al., 1994, EMBO Journal 13: 1476–1481.
Parker, 1990, Semin. Cancer Biol. 1: 81–87.
Pastorcic and Das, 2000, Journal Biol. Chem. 275: 34938–34945.
Pedersen et al., 1994, Mol. Microbiol. 11: 1085–1098.
Perlak et al., 1990, Biotechnol. (NY) 8: 939–943.
Peronnet et al., 2000, Mol. Gen. Genet. 262: 1123–1131.
Phogat et al., 2000, Journal Biosci. 25: 57–63.
Picton et al., 1993, Plant Physiol. 103: 1471–1472.
Pinkerton et al., 1999, Insect Mol. Biol. 8: 423–434.
Pohlman et al., 1984, Cell 37: 635–643.
Potikha et al., 1999, Plant Physiol. 119: 849–858.
Pugh, 2000, Gene 255: 1–14.
Quaedvlieg et al., 1998, Plant Mol. Biol. 37: 715–727.
Raizada and Walbot, 2000, Plant Cell 12: 5–21.
Rao et al., 2000, Proc. Natl. Acad. Sci. USA 97: 3936–3941.
Raynal et al., 1989, Plant Physiol. 91: 829–836.
Reichel and Beachy, 2000, Journal Virol. 74: 3330–3337.
Reznikoff et al., 1999, Biochem. Biophys. Res. Commun. 266: 729–734.
Rogers, S., U.S. Pat. No. 5,034,322, issued on Jul. 23, 1991.
Rogers, S., U.S. Pat. No. 5,378,619, issued on Jan. 3, 1995.
Rommens et al., 1993, Bioessays 15: 507–512.
Sambrook et al., 1989, Molecular Cloning: A Laboratory Manual, Cold Spring Harbor Laboratory Press, Cold Spring Harbor, N.Y.
Sasaki et al., 2000, Biosci. Biotechnol. Biochem. 64: 1775–1793.
Sautter et al., 1991, Biotechnol. (N Y) 9: 1080–1085.
Schena et al., 1991, Proc. Natl. Acad. Sci. USA 88: 10421–10425.
Schlappi et al., 1994, Cell 77: 427–437.
Schlappi et al., 1996, Plant Mol. Biol. 32: 717–725.
Schoenbeck et al., 2000, Journal Exp. Bot. 51: 29–39.
Scortecci et al., 1999, Plant Mol. Biol. 40: 935–944.
Selvakumaran et al., 2001, Cancer Res. 61: 1291–1295.
Shiina et al., 2000, Plant Cell Physiol. 41: 367–371.
Shimamoto et al., 1993, Mol. Gen. Genet. 239: 354–360.
Shimizu et al., 1997, Gene 205: 103–107.
Shimizu et al., 2000, Insect Mol. Biol. 9: 277–281.
Sisk et al., 2000, Journal Immunol. 165: 2511–2517.
Smania et al., 1999, Genetica 105: 233–238.
Solis et al., 1999, Hereditas 131: 23–31.
Soutoglou et al., 2000, Mol. Cell 5: 745–751.
Spellerberg et al., 2000, Gene 241: 51–56.

Stewart et al., 1996, Plant Physiol. 112: 121–129.
Stromvik et al., 1999, Plant Mol. Biol. 41: 217–231.
Suzuki et al., 2001, Plant Mol. Biol. 45: 123–131.
Takumi et al., 1999, Genome 42: 1234–1241.
Tamura et al., 2000, Nat. Biotechnol. 18: 81–84.
Tansey and Shechter, 2000, Prog. Nucleic Acid Res. Mol. Biol. 65: 157–195.
Tatematsu et al., 2000, Genes Cells 5: 677–688.
Terce-Laforgue et al., 1999, Plant Mol. Biol. 39: 551–564.
Terzaghi and Cashmore, 1997, Methods Mol. Biol. 62: 453–462.
Thain et al., 2000, Curr. Biol. 10: 951–956.
Thomas et al., 1993, Nature 362: 471–475.
Tommerup et al., 1990, Eur. Congr. Biotechnol. 5: 916–918.
Tosi and Beverley, 2000, Nucleic Acids Res. 28: 784–790.
Trieu et al., 2000, Plant Journal 22: 531–541.
Tu, 2000, Mol. Biol. Evol. 17: 1313–1325.
Turlan and Chandler, 2000, Trends Microbiol. 8: 268–274.
Umov et al., 2000, EMBO Journal 19: 4074–4090.
VanHoudt et al., 2000, Mol. Gen. Genet. 263: 995–1002.
VanWest et al., 1999, FEMS Microbiol. Lett. 178: 71–80.
Venter et al., 2001, Science 291: 1304–1351.
Verdaguer et al., 1996, Plant Molecular Biology 31: 1129–1139.
Vicient et al., 2000, Journal Exp. Bot. 51: 1211–1220.
Vilardell et al., 1990, Plant Mol. Biol. 14: 423–432.
Vilardell et al., 2000, Mol. Cell 5: 761–766.
Vincent et al., 1997, Planta 201: 424–433.
Volff and Altenbuchner, 2000, Microbiology 146 (Pt 4): 923–933.
Wandelt et al., 1992, Plant Journal 2: 181–192.
Wang et al., 2000a, Mol. Cell Biol. 20: 6904–6912.
Wang et al., 2000b, Insect Mol. Biol. 9: 145–155.
Wang et al., 2000c, Virus Genes 20: 11–17.
Warbrick et al., 1998, Nucleic Acids Res. 26: 3925–3932.
Weil and Kunze, 2000, Nature Genet. 26: 187–190.
Whitbred and Schuler, 2000, Plant Physiol. 124: 47–58.
Wielgosz et al., 2001, Journal Virol. 75: 3509–3519.
Williams and Baker, 2000, Science 289: 73–74.
Xiao and Peterson, 2000, Mol. Gen. Genet. 263: 22–29.
Yamada and Bohnert, 2000, Plant Cell Physiol. 41: 719–725.
Yamamoto et al., 1995, Plant Mol. Biol. 27: 729–741.
Yamasaki et al., 2000, Journal Bacteriol. 182: 3104–3110.
Yant et al., 2000, Nat. Genet. 25: 35–41.
Yin et al., 1998, I. Chuan. Hsueh. Pao. 25: 517–524.
Zhang and Levine, 1999, Proc. Natl. Acad. Sci. USA 96: 535–540.
Zhang et al., 2000a, Blood 96: 2641–2648.
Zhang et al., 2000b, Proc. Natl. Acad. Sci. USA 97: 9665–9670.

All references cited in this specification are hereby incorporated in their entirety by reference. The discussion of the references herein is intended merely to summarize the assertions made by their authors and no admission is made that any reference constitutes prior art. Applicant reserves the right to challenge the accuracy and pertinence of the cited references.

The invention relates in general to molecular biology and specifically to transposable elements (i.e., so-called "jumping genes" or mobile DNA). Transposable elements have now been found in almost all organisms which have been examined; they were first discovered in maize (corn), however, by Barbara McClintock in the 1940's.

The first family of transposable elements discovered by McClintock was the Activator/Dissociation (Ac/Ds) family. The maize Activator (Ac) transposable element (TE) and its encoded transposase protein (TPase) are well-studied with regard to functions involved in element transposition (e.g., Becker and Kunze, 1997; Brutnell and Dellaporta, 1994). The Ac element and TPase are not well-studied, however, with regard to other potential functions and useful applications. For example, to my knowledge Ac transposase has not previously been shown to act on non-transposon promoters, nor has it been implicated in having a second function aside from one in element-regulated transposition, namely, a novel function as a transcription factor or transcriptional modifier of non-TE genes. This is in spite of the fact that Barbara McClintock originally called TEs "controlling elements". McClintock used this term to suggest that mobile elements were part of a genome-wide system of genetic control involved in regulating development and differentiation (Comfort, 1999).

The maize Ac transposable element DNA sequence is 4.6 kb in length, has 11-bp imperfect terminal inverted repeats (TIRs), and generates an 8-bp duplication of target site genomic DNA upon insertion (Behrens et al., 1984; Chen et al., 1987; Fedoroff et al., 1983; Fedoroff et al., 1984; Kunze et al., 1987; Muller-Neumann et al., 1984; Pohlman et al., 1984). The central portion of the Ac element has five exons and four introns and encodes a single 3.5 kb mRNA. The mRNA encodes a protein of 807 amino acids, the transposase (Kunze et al., 1987).

The transposase (TPase) is necessary and sufficient for element transposition. The Ac TPase binds to element DNA, presumably in a cooperative manner, i.e., as multiple protein units that interact with one another. The TPase binds to several subterminal DNA sequences at either end of the Ac element (within ~250 nucleotides of each end) and to the TIRs. Specifically, it binds cooperatively to repetitive 5' ACG 3' and 5' TCG 3' sequences, 25 copies of which are found in the 5' and 20 copies in the 3' subterminal element regions. The binding affinity of TPase for target sequences is highest when the sites are flanked on the 3' end by an additional G residue (5' ACGG 3' or 5' TCGG 3'), a phenomenon which is found at 75% of transposable element binding sites (Becker and Kunze, 1997). The TPase also binds strongly to 5' AAACGG 3' hexamer motifs within subterminal element regions and with much lower affinity to the 11-bp TIR sequences. Finally, the TPase appears to be flexible in its ability to bind to DNA, in that two direct or inverted binding sites bind equally well, and binding sites spaced five to twelve nucleotides apart are good targets for the TPase (Becker and Kunze, 1997). Cooperative binding of the TPase to the short DNA motifs is critical for transposition. DNA methylation and hemi-methylation of the Ac hexamer motifs affects TPase binding (Kunze et al., 1997) and it is suggested that methylation is involved in controlling the mobility of transposable elements. Ac transcription is constitutive at low levels, and the Ac TPase is a very rare protein in maize cells (R. Kunze, personal communication, August 1999); moreover, indirect evidence has indicated that the "Activator (TPase) is active as an oligomer and forms inactive macromolecular complexes expressed in large amounts" (Essers et al., 2000). The Ac promoter is not regulated with the cell cycle but it is expressed at higher levels in dividing cells (Fridlender et al., 1998).

When a portion of the Ac wx-m9 element was used to probe Southern blots of maize genomic DNA, 4 to 10 Ac-hybridizing sequences were detected. These have varying lengths and are present as cryptic elements in the Ac wx-m9 genome (Fedoroff et al., 1983). Approximately 9 Ac-homologous bands were also detected in plants homozygous for an active Ac element at loci for waxy, bronze, R, C2 and P (Chomet et al., 1987). The authors concluded that 9 copies approximates the Ac sequence number in the maize genome. However, not all maize lines contain active Ac elements capable of transposition.

Certain attributes of the Ac element and its TPase, described above, might be used as anecdotal evidence against its having a "second function" such as a function in gene regulation (e.g., low Ac copy numbers; element methylation; low amounts of TPase produced; lack of active Ac in all maize lines). Moreover, there is no specific indication in the literature that the Ac TPase can serve to regulate gene transcription of non-TE genes.

In an analogous system, the transposition protein encoded by the maize Suppressor-mutator (Spm) transposable element, TnpA, can function as a transcriptional repressor of the unmethylated Spm transposable element promoter. However, such within-element repression was not determined for non-transposable element promoters, and such an effect on non-transposable element (i.e., plant gene or animal gene) promoters would not be expected from those data. Evidence that TEs and/or their encoded transposases, sometimes in conjunction with other transgenic or native proteins, can act both to repress and to enhance TE gene expression also comes from Schlappi et al. (1996). They showed that TnpA (the Suppressor-mutator (Spm) element's transposase) can repress the unmethylated Spm promoter; and, in a separate experiment, they found that 33–45-fold activation of the Spm promoter occurred when the VP16 activation domain was fused to that Spm promoter, the activation further requiring TnpA-DNA binding sites. Moreover, Schlappi et al. (1996) found that two regions of the Spm transposase yielded the highest level of transcriptional activation when fused to VP16, namely the DNA-binding domain and the protein dimerization domain, in deletion derivative studies. These studies, although demonstrating the versatility of the Spm element system, do not suggest that all transposases would have such versatile alternate functions, nor do the above results suggest that TnpA or other transposases could function to regulate the expression of non-transposable element (e.g., host) genes in vivo or in vitro.

Fridlender et al. (1996) showed that Ac TPase can repress Ac element promoter activity in transgenic tobacco plants and in protoplasts. In their experiments, they used a plasmid called "35S: GUS", as both a positive control for GUS expression and as a control for the Ac TPase effect on expression of a non-Ac related (i.e., a CaMV 35S) promoter. They found that activity of the CaMV promoter within the "35S: GUS" construct was not significantly affected by the Ac TPase (although expression was slightly lower with, than without, the TPase present).

Additional references suggest that some inverted DNA repeat sequences can have a role in transcriptional and post-transcriptional gene silencing, i.e., they can serve as transcriptional repressors (Muskens et al., 2000), while other references suggest that transposons inserted into the promoters of host genes can affect those genes' expression (Matzke et al., 2000). Neither reference establishes that transposons or their protein products explicitly cause gene transcriptional repression, however. Still another reference, concerning the "BED finger" DNA-binding domain which is found in selected transposases and also in DREF, a transcription factor (Aravind, 2000) lends support to the hypothesis that some transposases resemble transcription factors in certain of their protein domains. Another reference by Scortecci et al. concerning studies of Ac transposon promoter expression, found an inhibitory effect of the maize Ac 5' G-C rich UTL (untranslated leader region), on Ac promoter-driven and 35S promoter-driven reporter gene expression; they suggest the Ac-related inhibitory effect is exerted at the post-transcriptional level, probably due to a stable secondary structure formed in the mRNA. These articles, taken together, suggest that inverted repeat-containing transposable elements (e.g., such as the Ac element, which possesses inverted repeats at its terminii) and their products might possibly serve as transcription factors, but would not lead the skilled artisan to believe that any such factors would likely cause transcriptional repression of host genes.

There are two existing patents which each deal with transposable elements and which especially relate to the present invention: (1) U.S. Pat. No. 4,732,856 (issued Mar. 22, 1988), Assignee: Carnegie Institution of Washington (Washington, D.C.), entitled: "Transposable elements and process for using same", in which transposable elements isolated from maize are described, including Ac, and a process for using the same to identify and isolate genes and to insert desired gene sequences into plants in a heritable manner is described; and (2) U.S. Pat. No. 5,955,361 (issued Sep. 21, 1999), Assignee: Pioneer Hi-Bred International, Inc. (Des Moines, Iowa), entitled: "P gene promoter constructs for floral-tissue preferred gene expression", in which the invention provides a transcriptional regulatory region of a gene which is utilized to direct tissue-specific gene expression in plants such that a selective advantage is conferred upon said plants, and in which some of the constructs involve inserting an Ac transposable element into the P gene locus, an invention which also relates to the isolation, characterization and utilization of a transcriptional regulatory region of a plant gene which is expressed in a floral tissue-specific manner. However, neither patent describes a general method for altering targeted gene expression.

A third patent (U.S. Pat. No. 5,217,889; Roninson et al., Jun. 8, 1993; "Methods and applications for efficient genetic suppressor elements") deals with methods for isolating and identifying genetic elements (DNA) capable of inhibiting gene function. However, that patent does not specifically discuss transposable elements or their encoded transposases in this context or as examples, nor does it discuss anything about the ability to suppress gene transcription by the insertion of genetic elements in non-coding or within promoter regions of genes.

There is a continuing need for genetic elements that regulate gene expression in plants and in other eukaryotic systems. The controlled repression of key plant genes of interest would be especially useful, as no strong and faithful repressors are currently available in plant systems. The use of a genetic element for gene repression, or, for the controlled alteration of gene expression in eukaryotes would be of great potential regulatory value. It would also lead to the discovery of new gene functions within these and other model organismal systems. Further references about the need for molecular tools to alter gene expression are given in MacRae, 1999 (PI on NSF grant proposal number 9986293). None of these individual NSF grant proposal internal references or any combination of such references, however, would suggest to a skilled artisan or to a grant reviewer that any transposon, particularly Ac, would likely and necessarily fulfill the role of a molecular tool to alter gene expression.

SUMMARY OF THE INVENTION

The present invention is based on the discovery that the binding of a transposase to, or adjacent to, a gene causes repression of the expression of the gene. This repression occurs whether or not the transposase binds to a coding region or control region (e.g., the promoter) of the gene.

Accordingly, in some embodiments, the present invention is directed to methods of repressing transcription of at least one gene in a cell. The methods comprise introducing a transposase into the cell, wherein the transposase (protein) is capable of binding to the gene at the transposase's cognate DNA binding motif.

In other embodiments, the present invention is directed to methods of producing a population of cells that vary in their expression of a target gene. The methods comprise (a) transfecting the cells with a vector, the vector comprising a first polynucleotide sequence encoding the target gene operably linked to a promoter such that the target gene is expressed in the cells, wherein the vector has at least one binding motif for a transposable element within or adjacent to the target gene; and (b) transfecting some of the cells with a second polynucleotide encoding the transposable element operably linked to a second promoter such that the transposable element is expressed in the cells. In these methods, the target gene in the cells transfected with the second polynucleotide will exhibit reduced expression when compared to the target gene in the cells that were not transfected with the second polynucleotide. The cells can be further regenerated into whole organisms (e.g., a plant or an animal).

Additionally, the invention is directed to methods for repressing expression of a target gene in an organism. The methods comprise introducing transposases into the organism such that at least two transposases are capable of binding to the target gene, or adjacent to the target gene.

BRIEF DESCRIPTION OF THE DRAWINGS

FIG. 1. Part (A.) Diagram of the general gusA expression vector and the three CaMV promoter constructs used to transfect BY-2 protoplasts. The gusA expression vector is 4.9 kb (minus promoter) and contains the gene for Ampicillin resistance (designated AMP), plus the 1.8 kb gusA coding region in the orientation indicated. The promoter constructs are designated: −90-GUS, T1R−90-GUS, and CaMV 0.7-GUS; they are drawn schematically to show their relative sizes. T-1R−90-GUS is identical to the −90-GUS sequence except that it is is slightly larger than −90-GUS (by the addition of an Ac hexamer: AAACGG), and CaMV 0.7-GUS is 0.7 kb in size, approximately 600 bp bigger than the other two promoter constructs, yet it also includes the −90 to +8 CaMV promoter region common to the other two constructs. Part (B.) Diagram of the maize Ac effector construct, designated pLau6-Ac. This pLau6 is 3.5 kb (before Ac insert added) and contains the AMP gene. pLau6 contains the 511 bp cassava vein mosaic virus promoter 2 ($P_2$) (Verdaguer et al., 1996), in the orientation shown by the arrow, and the nopaline synthase (Nos) terminator sequence. Between promoter and terminator sequences is an insertion from the maize Activator (Ac) element. The insert is a 3.28 kb internal Ac BanII fragment containing introns, which was blunted and ligated into the EcoRI and BglII restriction sites in the vector, after they were made blunt. The 3.28 kb fragment contains nucleotides 1070 to 4352 of the 4810 bp Ac wx-m9 allele [accession number K01964], on the other strand from that given in the accession sequence, and encodes the Ac transposase.

FIG. 2. Mean GUS activity (RFU/sec) plotted for three effector treatments and differing CaMV promoter constructs, as used in two experiments: C and D. The three effector treatments are: Ac effector (mean values shown as the far left horizontal ticks within each of the four panels; see FIG. 1B for Ac effector description); No effector (mean values shown as the middle horizontal ticks within each of the four panels); and pUC18 mock effector (mean values shown as the far right horizontal ticks within each of the four panels). The CaMV promoter constructs shown on the x-axis (also called gusA vectors, elsewhere) are those described in FIG. 1A: CaMV 0.7-GUS (experiments C and D), T-1R−90-GUS (experiment C), and −90-GUS (experiment C); their use is explained in Table 2. Mean GUS activity values are shown, plus and minus two standard errors of the mean (the 95% confidence interval). It should be noted that if the means were plotted plus and minus only 1 standard error bar, the endpoints of these 1 standard error bars would correspond exactly to the two data values used to obtain each of the respective mean values shown.

FIG. 3. Sequence of the 0.7 kb GaMV 35S native promoter region (SEQ ID NO:9) with triplet DNA motifs (5' ACG 3' and 5' TCG 3') for Ac transposase-DNA binding shown. There are 34 putative Ac transposase-DNA binding triplet motifs shown on both strands. These ACG and TCG motifs are indicated by grey shading. There are also four instances of tetramer Ac binding motifs ACGG and TCGG on either strand, shown by \ symbols below the sequence. In 12 cases where two triplet Ac transposase binding sites overlap each other on either strand, this is shown by underlining. For example, ACGA means that the motif 5' ACG 3' exists on one strand, and the motif 5' TCG 3' overlaps this but in inverse orientation on the other strand; similarly, ACGT means that 5' ACG 3' and 5' ACG 3' overlap; and, TCGT means that 5' TCG 3' and 5' ACG 3' overlap. In total, of 34 Ac transposase binding triplet motifs, 24 (71%) show this overlapping phenomenon on either strand. This is contrasted with six such instances of overlapping Ac triplet motifs found at each end of the maize Ac element (Becker and Kunze, 1997). Becker and Kunze (1997) showed the Ac transposase binds cooperatively to ACG and TCG motifs. However, gel shift and other assays have not been performed to test the 0.7 kb CaMV native promoter shown here, for its transposase binding properties. The symbol "+8" indicates the last base of the 35S promoter sequence shown, 8 bases 3' of the transcription start; the −90 site is shown by a triangle pointing to the "A" base above it. The "−90-GUS" and "T-1R−90-GUS" promoter constructs (whose CaMV sequence portion is also shown here) each contain 5 Ac triplet transposase binding motifs. The "T-1R−90-GUS" reporter construct further contains 1 Ac hexamer binding site (FIG. 1A; hexamer not shown here).

FIG. 4. Outline of ELISA protocol. The flow chart outlines the initial binding of yeast recombinant proteins to the ELISA plate, the addition of primary and secondary antibodies, washes, and the final detection of a yellow-colored product produced by the cleavage of PNPP by alkaline phosphatase. This visible product is then quantitated on a spectrophotometer at 405 nm, to determine the amount of a specific protein (e.g., Ac TPase) which was bound to the nickel-coated ELISA plate.

DETAILED DESCRIPTION OF THE INVENTION

Unless otherwise indicated, the practice of the present invention employs conventional techniques of cell culture, molecular biology, microbiology, and recombinant DNA manipulation which are within the skill of the art. Such techniques are explained fully in the literature. See, e.g., DNA CLONING, Volumes I and II (D. N. Glover, ed., 1985); OLIGONUCLEOTIDE SYNTHESIS (M. J. Gait ed., 1984); NUCLEIC ACID HYBRIDIZATION (B. D. Hames and S. J. Higgins, eds., 1984); B. Perbal, A PRACTICAL GUIDE TO MOLECULAR CLONING (1984); the series, METHODS IN ENZYMOLOGY (Academic Press, Inc.); VECTORS: A SURVEY OF MOLECULAR CLONING VECTORS AND THEIR USES (R. L. Rodriguez and D. T. Denhardt, eds., 1987, Butterworths); CLONING, A LABORATORY MANUAL, second ed., Cold Spring Harbor Laboratory Press; and Ausubel et al. (1995), SHORT PROTOCOLS IN MOLECULAR BIOLOGY, John Wiley and Sons. Additional references pertinent to the above methods as used in plants include (Bhattacharyya-Pakrasi et al., 1993; Heinlein et al., 1998; Osbourn et al., 1989; Reichel and Beachy, 2000), and references therein.

The present invention is based on the surprising discovery that transposable elements (also known as transposons) can function to repress expression of non-transposable element genes. This discovery can be used to provide methods for repressing expression or a gene or genes within a cell. The repression phenomenon and mechanism of this invention are not associated with the previously described ways that transposable elements are known to affect the transcription of genes, i.e., by causing insertional mutations within the coding region or the promoter of the gene.

According to the present invention, repression of a particular gene in a cell by a transposable element occurs when at least one transposable element transposase binding site DNA motif is present in or adjacent to the gene and a transposon transposase is present in the cell such that the transposase binds to the gene at the binding site. The transposase is preferably present due to its expression from a gene, preferably a recombinant gene, present in the cell.

Repression of particular genes thus occurs when more than one transposase binding site DNA motif is operably linked to a gene, and a transposase is present to bind to the motif.

As used herein, the term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. More specifically, this term can also be used to refer to the chemical fusion of two or more fragments of DNA in a proper orientation such that the fusion preserves or creates a proper reading frame, or makes possible the proper regulation of expression of the DNA sequences when such sequences are transformed into an organism. Also as used herein, a "gene" is defined as a nucleic acid sequence that contains information needed for expressing a polypeptide or protein; more specifically, here it also refers to a nucleic acid fragment that expresses mRNA, functional RNA, or a specific polypeptide or protein, also including any regulatory sequences that are found in the 5' region, such as the promoter, promoter elements, enhancers, cis DNA binding motifs that could influence the expression of the gene, and "transposase DNA binding motifs". "Transposase DNA binding motifs" are defined herein as short DNA sequences (e.g., 3–35 bases in length) to which a transposase enzyme can bind, and they are usually located, in more than 1 copy, within the 5' and/or 3' regions of that transposase's cognate transposable element, as well as within other, non-TE host genes. As an example of such motifs, the Ac element's "Ac transposase DNA binding motifs" are further described both directly below, and in Example 1.

Thus, in some embodiments, the present invention is directed towards methods of altering and particularly repressing the expression of at least one targeted gene within a cell or organism. The methods comprise introducing a transposable element effector molecule, which encodes a transposase protein, into the cell or organism such that a transposable element inserts into or adjacent to the gene. The targeted gene(s) can be either native to the organism/cell, introduced foreign genes, or a mixture of native and foreign genes. The methods of the present invention can be carried out using any transposase-encoding, transposable element. Examples include members of families and superfamilies consisting of: Slide, Tpn1, Tgm1, Tam1, Tam3, Pac1, Hobo, members of the Tnr1/Stowaway family, members of the En/Spm family, members of the Tourist family, members of the broad Tc1/mariner superfamily, members of the Minos family, members of the Tn5 family and other Tn-relatives, members of the Mutator family (from maize), members of the miniature inverted-repeat transposable element (MITE) class (highly reiterated TEs in plants, insects and humans), members of the Basho family, members of the P-element family, members of the Sleeping Beauty family, members of the Pogo family, members of the Tiggers family, members of the broad class of bacterial IS elements, members of the broad hAT-transposable element superfamily, members of the Hermes family, members of the Mos1 family, and members of the piggyBac family. In preferred embodiments, the transposable element is an Activator (Ac) transposable element.

The terms "Activator element", "Ac", "Dissociation", "Ds". "Ac/Ds family members", "Ac superfamily", "hAT superfamily", "deletion derivatives of Ac" "Ac wx-m7", "Ac wx-m8", "Ac wx-m9", "mutated Ac family members", "truncated Ac elements", and "mutant Ac elements" are all included herein within the present invention; and, these terms are described and defined within the several References cited herein (e.g., Kunze et al., 1997; Rommens et al., 1993; Kempken and Kuck, 2000).

The methods of the present invention are not narrowly limited to any particular cell or organism. In some preferred embodiments, the cells in these methods are plant cells, for example cells of a monocot plant such as *Zea mays*, or other monocots such as rice, wheat, oats, rye or barley, or dicot plants, including members of the Solanaceae family such as a pepper, a *Lycopersicon species*, a potato, or a *Nicotiana* species, for example *N. tabacum*, or a legume family member for example soybean, or a member of the family Brassicaceae, for example from *Arabidopsis thaliana*, or a morning glory, or a cotton plant. The plant cell may also be part of a cell culture that can be regenerated into a whole plant.

The cell may also be a bacterial cell, for instance *E. coli*. The cell may also be a cancer cell, a cell containing a retrovirus, a cell with abnormal growth properties, or a cell showing signs and properties of aging. Still further embodiments include repressing expression of targeted genes within diverse organisms including insects such as *Drosophila species*, eukaryotic microbes such as fungi (e.g., yeast, *Dictostelium*), nematodes (e.g, *Caenorabditis elegans*) and mammals (e.g., rodents, humans).

The targeted gene can be any gene to which repression of expression is desired. For plant cells and organisms, examples include genes involved in stomate opening (to affect drought tolerance), and defense-related processes such as anti-herbivory, anti-fungal, anti-viral, anti-bacterial, and anti-insecticidal genes. Preferred anti-insecticidal genes include any of the *Bacillus thurengensis* endotoxin genes, including those that are anti-lepidopteran, anti-dipteran, anti-coleopteran, and anti-hymenopteran. In a particular, preferred embodiment within plants, the targeted gene is a foreign, bacterial uidA gene from *E. coli*, encoding the enzyme β-glucuronidase (GUS).

In some embodiments the gene targeted for repression is a proto-oncogene, whose uncontrolled over-expression at the wrong time in development or within the wrong cell type, can lead to cancer. The controlled down-regulation of such oncogenes could lead to the mitigation of such cancer.

In other embodiments, the targeted gene is a key gene in a biochemical pathway, serving as a master switch gene able to regulate several other genes within the same pathway by virtue of its position in the pathway hierarchy. In particular embodiments specific to plants, that key master switch gene is involved in such biochemical and cellular processes as photosynthesis, plant flowering, and plant defense mechanisms. In other embodiments useful in both plants and non-plants, the key switch gene is involved in processes such as glycolysis, metabolism, transcription, translation, central intermediary metabolism, cellular transport, protein binding, protein cascades, organismal development, embryogenesis, wounding, wound healing, responses to the environment, cancer, and disease. In further embodiments specific to those organisms with an immune system, the key or master switch gene is involved in immune responses such as tissue rejection, antibody production, and effector production.

In further embodiments, the gene(s) targeted for repression contain a specific chemical control switch that is a chemically-induced promoter. In these embodiments, the targeted gene(s) can only be repressed in the presence of both an Ac effector molecule plus a chemical that binds to the chemically-induced promoter. In another embodiment, the Ac effector molecule itself contains the chemically-induced promoter, such that the Ac effector molecule cannot itself be expressed (i.e., cannot produce the Ac transposase) except in response to exposure to the chemical binding to the chemically-induced promoter. In preferred embodiments of this invention, the transcriptional repression of the targeted gene or genes is either very strong, strong, or moderate in its magnitude compared to normal (wild type, non-repressed) targeted gene expression levels. The repression can be of either a targeted gene within a cell, or of several genes within a whole organism.

In certain embodiments, the targeted gene is part of a recombinant polynucleotide in the cell. Preferably, the targeted gene is inserted stably into a chromosome in the cell. Preferably, the targeted gene contains at least one Ac transposase DNA binding motif adjacent (5') to the targeted gene, that motif consisting of: a specific DNA hexamer, a specific DNA trimer, a specific DNA tetramer, or a mixture of specific hexamer, trimer and tetramer Ac transposase DNA binding motifs. More preferably, the targeted gene further comprises at least about 35 copies of such hexamer/trimer/tetramer Ac transposase DNA binding motifs, even more preferably, at least about 50 copies of such hexamer/trimer/tetramer Ac transposase DNA binding motifs. In the most preferred embodiments, the targeted gene comprises at least about 100 copies of such hexamer/trimer/tetramer Ac transposase DNA binding motifs. The targeted gene may also be transfected into the cell as plasmid DNA (on a plasmid DNA construct). Multiple genes containing such adjacent Ac transposase DNA binding motifs may also be targeted for their repression simultaneously. The targeted gene(s) and the Ac effector molecule are introduced into the organism on the same polynucleotide, or, alternatively, the targeted gene(s) and the Ac effector molecule are introduced into the cell on different polynucleotides.

The Ac effector molecule encoding the transposase may be introduced into the cell as one copy of the effector, or as multiple copies. The multiple Ac effector molecules preferably incorporate into different genomic locations within the cell. The Ac effector molecule may also be only transiently (not stably) introduced and expressed within cells. In a further embodiment, the Ac effector molecule is any related member of the "Ac superfamily" of transposable elements, any member of the hAT superfamily of transposable elements, or, even any transposable element introduced into a cell or organism.

Concerning the cells and methods of plant transformation used in this invention, the plant cells to be transformed may be protoplast cells, callus cells, leaf cells, root cells, or any other type of plant cells.

Further embodiments include the introduction of transposable element (TE) effector molecules that are sequences native to the organism, sequences foreign to the organism, or a combination of native and foreign sequences. Such a TE effector molecule can be placed under the control of any suitable promoter such as an animal promoter, plant promoter, viral promoter, bacterial promoter or a fungal promoter. In a preferred embodiment, the TE effector molecule is under the control of the Cassava vein mosaic virus (CsVMV) viral promoter $P_2$. In order to introduce sufficient numbers of TE binding motifs, it may be necessary to remove, delete, inactivate, or recombine out native copies of the targeted gene, prior to introduction of the respective foreign transgene copies. Alternatively, organisms and cells may be chosen for transformation of a particular foreign effector gene, because they contain no native copies or homologues of that exact foreign effector gene sequence.

The present invention is also directed to methods of producing a population of organisms that vary in their respective levels of expression of a desired, targeted gene or genes. The method comprises inserting differing amounts of transposase DNA binding sites into different members of the population, then introducing the transposon (effector molecule) into the population. Preferably, the transposon is an Ac effector element. While this method would work with essentially any organism, the preferred organism is a plant, such as the several plant species previously described. This method can be accomplished in any of a number of ways, however, a preferred method of practicing this method for plants includes engineering a vector comprising the desired gene(s) plus at least one Ac transposase DNA binding motif adjacent (5') to each of these targeted gene(s). This is followed by transfecting plant cells with the above vector, then selecting for a transfected cell (within each plant) that has integrated the DNA vector into its chromosome(s) and which is also expressing the targeted gene(s). Following this double selection, the cells from individual plants are cultured to produce multiple cell copies; these cells are divided into more than one group of cells; one cell group from each plant is transfected with the Ac effector molecule, another group is transfected with a control molecule, and one group remains untransfected; the cells from each group and from each plant are regenerated into whole plants and examined for repression of the target gene(s) specifically in the presence of the Ac effector molecule.

In additional embodiments, the above method of producing a "range of target gene expression levels" can also be adapted in any non-plant species, including vertebrate and nonvertebrate multicellular and single cellular organisms such as mice, other rodents, *C. elegans, Drosophila, E. coli* cats, primates, humans, enteric bacteria, bacteriophage, and viruses, including for example tobacco mosaic virus and HIV.

The invention can be utilized as a method of accomplishing several practical goals. Nonlimiting specific examples of these embodied goals include: (1) determining the functions of genes within an organism; (2) repressing translation within an organism; (3) modifying (increasing, decreasing, or altering) transcription within an organism; (4) repressing transcription of a gene encoding antibiotic resistance; (5) repressing a targeted gene's expression when that gene is involved in human disease; (6) repressing targeted genes within human gametes; (7) repressing targeted genes involved in cellular functions such as DNA methylation/demethylation, protein phosphorylation/dephosphorylation, histone deacetylation, signal transduction, and transmembrane functions; (8) repression achieved by interaction of the transposase with other proteins; (9) repression achieved by general toxicity of the over-expressed transposase to the organism; (10) repression wherein the transposase is directed to the cell cytoplasm; (11) repression wherein the transposase is directed to a particular cellular organelle, including: nucleus, mitochondrion, chloroplast, leukoplast, starch granule, ameloplast, endoplasmic reticulum, ribosome, cell membrane, vacuole, golgi body, nucleolus, nuclear membrane, and cell wall; (12) repression within an in vitro cell system; (13) repression of transcription of genes during the cell cycle, wherein the genes are from $G_1$, S, $G_2$, or M phases; (14) repression of transcription within a transplanted organ, shoot, or body part including grafted plant parts and transplanted human and other animal organs; and (15) repression of, or any useful alteration of gene expression of, at least one targeted gene in a cell; (16) any of the aforementioned above uses, where instead of the word "repression", the words "alteration of gene expression" are substituted.

Various aspects of the description of the invention provided above are more fully elaborated below.

As an example of the repression phenomenon (see "Example", in this section), in the case of the Activator (As) transposable element, the repression phenomenon occurs in the presence of Ac transposase binding site DNA motifs, in a dosage dependent manner. Ac transposase binding site DNA motifs are DNA hexamers, tetramers and trimers with specific DNA sequences; the Ac transposase can bind cooperatively to such motifs, which are also found within the 5' and 3' regions of the native maize Ac transposable element, as well as within numerous genes (MacRae et al., 1999). These motifs include the hexamer sequence 5'AAACGG3', the tetramer sequences 5'ACGG3' and 5'TCGG3', the triplet sequences 5ACG3' and 5'TCG3', as well as such pairs of triplets that overlap each other on either DNA strand (i.e., two overlapping triplets—ACG and/or TCG—sharing their middle 2 GC and CG base pairs on either DNA strand): 5'ACGT3', 5'ACGA3', 5'TCGT3', and 5'TCGA3'. The gene that is targeted for repression may also include any mixture of the above hexamers, tetramers and triplets, if they are spaced any short distance apart, between 1 base pair apart and 40 base pairs apart, on the same DNA strand, or on opposite DNA strands. Any transposable element's transposase, together with collections of that specific element's cognate transposase DNA binding motifs will affect expression of any target gene, when such transposase binding motifs are contained (linked in cis) or are adjacent to the target gene, for example within that gene's promoter region.

Up to 1,000 copies of the selected transposase DNA binding motifs may be present within or adjacent to the targeted gene; such motifs may be present within that gene's promoter region, and/or within an exon region, and/or within an intron region, and/or within a 5' leader region, and/or within a 3' trailer region, and/or within a non-coding region. Moreover, in certain embodiments, the transposase binding motifs may be made up of RNA instead of DNA, such that the transposable element's transposase binds to the motifs as existing on an RNA molecule, or as existing on RNA fragments.

The invention further provides for a "non-jumping mode" to exist for the effector TE whose transposase is to be employed; this unique, "non-jumping mode" is produced by inclusion of only that TE's DNA coding region, and not its terminal DNA inverted repeats and other terminal sequences which aid in transposition (Becker and Kunze, 1997). See also Example 1 below for details of how this "non-jumping mode" was attained for the Ac element.

Scortecci et al. (1999) have found an inhibitory effect of the maize Ac 5' G-C rich UTL (untranslated leader region), on Ac promoter-driven and 35S promoter-driven reporter gene expression. However, their findings differ significantly from the present invention, in that they did not show that other plant (host) genes or host gene promoters could be inhibited, nor did they establish or suggest that the Ac transposase protein was explicitly involved in the inhibition effect observed. Furthermore, they did not micro-dissect the 5' UTL region to determine exactly which sequences within the region were responsible for the inhibition; finally, they proposed a post-transcriptional mechanism of action for the inhibition of reporter gene expression, and suggest that stable secondary structure formation in the mRNA may be the cause of their effect.

The invention described herein has quite broad applications, as one skilled in the art will perceive that it could be directed towards all of the following general actions: repressing, enhancing or altering gene expression within a cell or organism, by using a transposable element (TE) effector molecule whose transposase can bind to its specific, cognate short DNA repeat motifs and thus produce the desired effect on gene expression. It is also understood by one skilled in the art that multiple, different TE effector molecules and/or multiple copies of such effector molecules can be introduced into the recipient organism or cell simultaneously, as required for the particular regulatory effect desired.

All transposases studied thus far recognize short DNA sequences in the terminal regions of their respective transposable elements and would be expected to also recognize the same short DNA sequences when those sequences exist within non-TE genes, in vivo or in vitro. Thus, although the evidence for repression by TEs comes from studies with Ac (see "Example"), the skilled artisan would expect the repression phenomena and mechanisms to include any other TE systems which also have such subterminal repeat sequences within their TE termini, and which encode a transposase enzyme. It is understood that this aspect of the invention could be applied so as to regulate the expression of targeted host organism genes and/or of TEs themselves, in vivo or in vitro. As understood by the skilled artisan, this invention could thus be allowed to include the Ac element as the effector molecule, or, any member of the "Ac superfamily" of elements, any member of the hAT superfamily of elements, and indeed any TEs as effector molecules such that the TEs can produce a transposase which binds to short cognate DNA sequences within genes and then functions to alter those genes' expression. Certain of these TEs, as cited below, can be expected by the skilled artisan to produce an increased level of targeted gene expression, or to produce a decreased level of targeted gene expression, above or below that produced strictly by the maize Ac transposable element alone, due to the respective differing amino acid sequences and potentially differing amino acid functional motifs as present within the different TEs.

Examples of TEs that are thus within the scope of this include: Ac, Spm/En, Tc1, Tc3, Pogo, Slide, Tpn1, Tgm1, Tam1, Tam3, a P element, Pac1, and Hobo, as well as members of the Tnr1/Stowaway family, members of the En/Spm family, members of the Tourist family, members of the broad Tc1/mariner superfamily, members of the Minos family, members of the Tn5 family and other Tn-relatives, members of the Mutator family (from maize), members of the miniature inverted-repeat transposable element (MITE) class (i.e., highly reiterated transposable elements in plants, insects, and humans), members of the Basho family, members of the P-element family, members of the Sleeping Beauty family, members of the Pogo family, members of the Tiggers family, members of the broad class of bacterial IS elements, members of the broad hAT-transposable element superfamily, members of the Hermes family, members of the Mos1 family, and members of the piggyBac family. See, e.g., Williams and Baker, 2000; Han et al., 2000; Zhang et al., 2000b; Shimizu et al., 2000; Klinakis et al., 2000a, b; Mukhopadhyaya et al., 2000; Davies et al., 2000; Schlappi et al., 1996; Le et al., 2000; Dahl et al., 2000; Turlan and Chandler, 2000; Phogat et al., 2000; Kholodii et al., 2000; Delattre et al., 2000; Yamasaki et al., 2000; Yant et al., 2000; Lawley et al., 2000; Feschotte and Mouches, 2000; Li et al., 1998; Wang et al., 2000b; Martusewitsch et al., 2000; Nagai et al., 2000; Smania et al., 1999; Rao et al., 2000; xiao and Peterson, 2000; Catteruccia et al., 2000; Jasinskiene et al., 2000; Essers et al., 2000; Peronnet et al., 2000; Takumi et al., 1999; Tosi and Beverley, 2000; Handler and Harrell, 1999; Raizada and Walbot, 2000; Tamura et al., 2000; Solis et al., 1999; Pinkerton et al., 1999; Spellerberg et al., 2000; Reznikoff et al., 1999; Fitzmaurice et al., 1999; Tu, 2000; Johns et al., 1985; Kunze et al., 1997; Alatortsev et al., 2000; and Benito and Walbot, 1997.

When a transposable element (TE) is used as an effector molecule to drive the gene repression phenomenon, the expression of that TE effector molecule (i.e., the production of that effector's RNA and protein) must be under the control of a "promoter". The skilled artisan will understand that several appropriate promoters can be used as required to drive expression (i.e., transposase production) from the transposasble element effector molecule that is selected. Such promoters include animal promoters, plant promoters, bacterial promoters, viral promoters, fungal promoters, chemically-induced promoters, as well as other types of promoters. A specific plant promoter of interest, driving strong effector molecule expression, is the Cassava vein mosaic virus promoter $P_2$, as described e.g., in the Example 1 below.

The terms "promoter" and "promoter region" as used herein refer to a sequence of DNA, usually upstream (5') to the coding sequence of a structural gene, which controls the expression of the coding region by providing the recognition for RNA polymerase and/or other factors required for transcription to initiate at the correct site. "Promoter" sequences are necessary, but not always sufficient to drive the expression of the gene. The "promoter" specifically includes a minimal promoter which is a short DNA sequence comprised of a TATA-box and other sequences that serve to specify the site of transcription initiation, to which regulatory elements are added for control of gene expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, the term "enhancer" as specifically used herein, is a DNA sequence which can affect "promoter" activity and may be an innate element of the "promoter" or a heterologous element inserted to enhance or to decrease or to alter the level or tissue-specificity of a "promoter". It is capable of operating in both orientations (normal or flipped), and is capable of functioning even when moved either upstream (5') or downstream (3') from the "promoter". Both enhancers and other upstream "promoter" elements bind sequence-specific DNA-binding proteins that mediate their effects. A "promoter fragment" as defined herein constitutes a fraction of the DNA sequence of the promoter region.

The present invention is not narrowly limited to the use of any particular promoters; it is envisioned that any promoter, now known or later discovered, could be useful for the present invention. Nonlimiting examples of promoters useful for driving the effector molecule's expression include bacterial promoters, plant promoters, fungal promoters, viral promoters, and animal promoters.

Bacterial promoters are promoters from bacterial sources. Particularly useful bacterial promoters for practicing the present invention with plants are, for example, *Agrobacterium*-derived promoters. Such promoters include those derived from *Agrobacterium* T-DNA opine synthase genes, and include the nopaline synthase (nos) promoter (Rogers, 1991), the octopine synthase (ocs) promoter (Leisner and Gelvin, 1988) and the mannopine synthase (mas) promoter. Many other bacterial promoters are known, and could be utilized in the practice of the present invention.

Plant promoters are promoters derived from plant sources. For the present invention, useful plant promoters that are effective in providing constitutive expression include hsp80, Heat Shock Protein 80 from cauliflower (Brunke and Wilson, 1993), and the tomato ubiquitin promoter (Picton et al., 1993). These promoters can be used to direct constitutive expression of heterologous nucleic acid sequences in transformed plant tissues. For the present invention, inducible and/or tissue-specific plant promoters are also of use, and these include the E4 and E8 promoters from tomato, which provide fruit-specific expression (Cordes et al., 1989; Good et al., 1994), as well as corresponding promoters from other plants which have substantially the same biological activity. The tomato E4 promoter requires ethylene for its activation, thus falling into the class of "CIPs" ("chemically-induced promoters"), while the tomato E8 promoter is controlled by ethylene as well as by separate developmental signals (Deikman et al., 1998). As defined herein, "chemically-induced promoters" are promoters which can alter (increase or decrease) the rate of expression of a gene to which they are operably linked, but only in response to the application of a specific inducing agent such as a particular chemical which "induces" that gene's promoter (see further discussion below). Another fruit-specific promoter of use to this invention is the tomato 2AII gene promoter. Further useful promoters include the constitutive maize ubiquitin promoter (Noury et al., 2000), those promoters used in circadian clock studies in *Arabidopsis* (Thain et al., 2000), the phenylalanine ammonia lyase (PAL), chalcone synthase (CHS), and other early phenylpropanoid promoters (Whitbred and Schuler, 2000), the psbA2 light-regulated promoter (Eriksson et al., 2000), the promoters of MEA (FIS1), FIS2, and FIE (FIS3) (i.e., promoters within genes that repress seed development in the absense of pollination; Luo et al., 2000), the promoter of the maize GapC4 gene (Geffers et al., 2000), the McMipA PIP aqauporin promoter (Yamada and Bohnert, 2000), potato invertase promoters (Hedley et al., 2000), the ABA-inducible HVA1 promoter from barley (Hagenbeek et al., 2000), the yeast fbp1 promoter (Neely and Hoffman, 2000), *Arabidopsis Em gene promoters (e.g., AtEm*1 and AtEm6 promoters; Vicient et al., 2000), and the pathogenesis related PRB-1b promoter from tobacco (Grichko et al., 2000). In addition, the ability to significantly increase the amount of a desired mRNA molecule in plants (e.g., the Ac TE's mRNA; see Example) has been shown to be affected by use of different, heterologous promoters, plus the addition of other necessary factors (e.g., use of 35S promoter and addition of the factor; Long et al., 1993; Becker et al., 1992).

The plant salicylic acid (SA)-inducible promoter, PR-1a, (a "chemically-induced promoter" or CIP) has recently been fused with the Ac transposase to yield an inducible transposable element effector termed INAc, designed for purposes of gene tagging via transposition in higher plants (Charng et al., 2000). Such an "Ac-SA inducible promoter" fusion could easily be modified to be rendered in a non-jumping form, and yet still be capable of producing the SA-inducible Ac transposase enzyme for use as an effector molecule within the present invention (see Example 1).

Numerous additional examples of plant promoters useful to this invention may also be found in the compilation by Okamuro et al. (1989).

Viral promoters are promoters derived from viral sources. Particularly useful viruses and viral promoters for the present invention are the Cassava vein mosaic virus promoters, including the viral promoter $P_2$ (Verdaguer et al., 1996; e.g., see the "Example"); the caulimovirus family of viruses (a group of double-stranded DNA viruses), including the Cauliflower Mosaic Virus (CaMV) 35S promoter (Balazs et al., 1982; Guilley et al., 1982; Odell et al., 1985; Odell et al., 1987; Odell et al., 1988; Tommerup et al., 1990; Jefferson et al., 1987; Jefferson, 1987; e.g., see the "Example"), and the CaMV 19S promoter (Fraley et al., 1994); plus the Figwort Mosaic Virus (FMV) (Rogers, 1995) promoter.

Animal viral promoters and other, related, expression-altering sequences are defined as sequences primarily derived from those viruses which infect animal hosts; they can, however, in select cases, be derived from non-viral sequences which are found present in animal hosts. Examples of such sequences especially useful for the present invention, include for example: the simian virus 5 antigenomic promoter (Keller et al., 2001), the herpes simplex virus type 1 promoter (Arthur et al., 2001), other herpes simplex promoters (Lachmann and Efstathiou, 1999), the Sindbis virus subgenomic mRNA promoter (Wielgosz et al., 2001), adenovirus promoters and their associated RNAs as well as other, related RNA-polymerase III-driven expression cassettes (Medina and Joshi, 1999), and, retrovirus-like element promoters (Selvakumaran et al., 2001).

Animal promoters are promoters derived from animal sources. Particularly useful animal promoters for the present invention are described below. In general, typical animal promoters are different from typical plant promoters, in that animal promoters show a GC-rich "TATA to start" sequence (generally 64% or greater GC content) that leads to a major groove compression. The expression "TATA to start" as used here means the DNA sequence between the primary TATA motif and the start of transcription. A "core animal promoter" comprises a TATA motif and a GC-rich "TATA to start" region, which when together placed 5' of a structural gene will promote constitutive expression that is non-tissue specific in transgenic plant cells. Moreover, for use in the present invention, it has been found that a GC-rich animal-type synthetic promoter also works very well in plants. Specific examples of animal promoters that are useful in the present invention include: constitutive mammalian promoters such as the actin promoter, tissue-specific promoters from such genes as the liver fatty acid binding (FAB) protein gene (specific for colon epithelial cells), the insulin gene (specific for pancreatic cells), the transphyretin, .alpha.1-antitrypsin, plasminogen activator inhibitor type 1 (PAI-1), apolipoprotein AI and LDL receptor genes (specific for liver cells), the myelin basic protein (MBP) gene (specific for oligodendrocytes), the glial fibrillary acidic protein (GFAP) gene (specific for glial cells), OPSIN (specific for targeting to the eye), and the neural-specific enolase (NSE) promoter (specific to nerve cells). Other animal promoter examples useful for the present invention include: the synthetic metallothionein I mouse promoter, the human c-erbB-2 promoter (expressed in breast tissues), the *Drosophila* metallothionein promoter, the *Drosophila* inducible Hsp-70 promoter, the *Drosophila* actin 5C promoter, and the *Drosophila* COPIA LTR promoter.

Fungal promoters are promoters derived from fungal sources. Particularly useful fungal promoters for the present invention include the yeast promoters, which can be either inducible or constitutive. A constitutive fungal promoter is understood as being a promoter whose expression is constant under standard culturing conditions. An inducible fungal promoter is understood as being a promoter whose expression is induced under defined environmental conditions or specific stimulii only. Examples of yeast promoters include those from the following genes: isocytochrome C1 (CYC1), alcohol dehydrogenase (ADH1), transcription elongation factor (TEF), yeast glyceraldehyde phosphodehydrogenase (GAPDH), and phosphoglycerate kinase (PGK). Native yeast promoters include wild-type α-factor as well as other yeast promoters. Useful yeast promoters also include those for the glycolytic enzyme genes such as phosphoglucoisomerase, phosphofructokinase, phosphotrioseisomerase, phosphoglucomutase, enolase, pyruvate kinase (PyK), glyceraldehyde-3-phosphate dehydrogenase (GAP or GAPDH), and alcohol dehydrogenase (ADH).

The present invention is also not limited to any particular organism or cell type, and may be utilized with prokaryotes, eukaryotes or archaea. Specifically, it can be applied to plant cells, to plant cells that can be regenerated into whole plants, to monocot plants, dicot plants, to a variety of animal cells, including normal cells of any type and cancer cells, to bacterial cells, to cells containing a retrovirus, to cells having abnormal growth properties, to cells showing signs of aging, plus to other, broader classes of heterologous cells and their heterologous host organisms, as described below. Plants and plant cells to which the invention can be applied include the following nonlimiting examples, as understood by the skilled artisan: maize, rice, wheat, oats, rye, barley, a *Nicotiana* species such as *Nicotiana tabacum*, a pepper, a *Lycopersicon* species, a potato, a turnip, a *Petunia*, a snap dragon, *Arabidopsis thaliana*, cotton, soybean, potato, sunflower, cassava, morning glory, a berry, a member of the legume family, and a member of the Brassicaceae family.

The Ac and Ds elements from maize have been successfully introduced into such diverse heterologous plants as rice, *Arabidopsis thaliana*, barley, *Petunia*, carrot, tomato, potato, and tobacco (Scortecci et al., 1999). Moreover, Ac and Ds elements have been shown to transpose in yeast, which normally lacks such class II, "cut and paste" transposons (Weil and Kunze, 2000). Additionally, the MURA protein from the MuDR transposable element of the Mutator family can also be expressed in yeast). Because TEs such as Ac and MuDR from plants have been introduced successfully into yeast cells, the skilled artisan would understand that these and other related plant transposons would also likely function in other heterologous eukaryotes from other kingdoms such as in nematodes (e.g., *C. elegans*), *Drosophila, Dictostelium*, and mammalian cells, including in human cells and in human cell lines. Such embodiments, as well as plant TE introduction into bacterial cells, are thus within the scope of the present invention. Furthermore, the skilled artisan will understand that the present invention includes and pertains not only to higher plant TEs, but to all such eukaryotic and also to prokaryotic TEs that can bind to specific DNA motifs and that encode a transposase or that encode that portion of a transposase which can both bind to DNA and also affect gene transcription. In addition, the skilled artisan will understand that any such TE encoding a whole or a partial transposase can be introduced into any heterologous organismal system. For instance, an animal TE (or part thereof) could be introduced into a plant, a fungal TE into an animal, a bacterial TE into a plant, a plant TE into a fungus or animal, and so forth.

TE Binding Motifs Within Targeted Genes

All TE transposases studied thus far recognize short DNA sequences in the terminal regions of their respective transposable elements. Selected TE examples whose cognate DNA binding motifs have been described or partially described, include: Pogo, Ac, Slide, Tpn1, Tgm1, Tam1 and En/Spm (Kunze et al., 1997). Given the range of diverse eukaryotic organisms from which the above and other example TEs are derived, the skilled artisan will expect that many additional TEs that also have transposases which can bind to specific DNA motifs, likely exist in other organisms. The present invention is not limited to the use of any particular transposons, but could be useful with any transposon now known or later discovered.

In some aspects, the present invention is directed to methods for repressing the transcription of at least one targeted gene within a cell. The methods comprise introducing a transposable element effector molecule into the cell. The repression is then produced via the transposase binding to DNA motifs usually found within the promoter region of the targeted gene, and down-regulating that targeted gene's expression.

As used herein, the term "targeted gene" or "target gene" is any nucleic acid (DNA or RNA) whose expression is altered by the methods of the present invention. The targeted gene could be present on a replicon (i.e., usually a plasmid vector) and/or in some embodiments it could be incorporated into the chromosome; it is usually a DNA polynucleotide which also encodes a protein molecule. The targeted gene can also be, for example, an RNA polynucleotide whose expression is affected by the methods of the present invention. More than one targeted gene can exist and/or can be introduced into an organism. In some embodiments of the invention, the targeted gene comprises copies of selected transposase DNA binding motifs within its 5' promoter region. When present on a replicon, the targeted gene is not usually essential for replicon replication. Additionally, targeted genes may comprise native genes inserted into a native organism, native genes inserted into a non-native organism, and/or foreign genes, each of these terms (native, foreign) as defined below. Furthermore, all targeted genes will be under the control of suitable regulatory sequences (e.g., enhancers, promoters). The regulatory sequences (i.e., enhancers and/or promoters) in the targeted gene may come from any source, including those sources described above (e.g., animal, bacterial, fungal, plant, or viral). Targeted genes may include DNA coding sequences or RNAs that are either heterologous or homologous to the genes/genome of a particular plant or organism to be transformed. In the "Example" given below, for instance, the targeted gene is the uidA bacterial (GUS) reporter gene (a DNA).

Target Genes: Types of Genes and Promoters to Control Them

The target genes envisioned for use in the present invention are not narrowly limited to any particular types of gene. Included, for example, are genes that influence the cellular, enzymatic, biochemical, or metabolic processes of the target organism being transformed, and reporter genes. In one preferred embodiment, for instance, the targeted gene is the bacterial uidA (GUS) reporter gene (see "Example" and included references). Additional reporter genes are also included within the scope of the present invention, such as for example, the Green Fluorescent Protein gene (e.g., Chalfie, 1995), other fluorescent protein genes related to or unrelated to the GFP gene (e.g., the Stratagene product "Vitality humanized Renilla GFP (hrGFP)", a low-toxicity GFP from a different organism than the EGFP protein, available at www.stratagene.com), the lacZ bacterial reporter gene, the CAT-chloramphenicol transferase reporter gene (e.g., Miller, 1972), and the luciferase gene (e.g., Sambrook et al., 1989). Also included within the scope of the present invention are targeted genes that affect the ability of another organism to harm the target, host organism being transformed, targeted genes that are key switch genes in a biochemical pathway, both targeted and effector genes containing a chemically-induced promoter (CIP), and targeted genes involved in water conservation in plants.

Nonlimiting examples of target genes in this invention that influence the cellular, enzymatic, biochemical, or metabolic processes of the target organism being transformed include genes involved in any of the following processes: pigmentation, amino acid biosynthesis, central intermediary metabolism, cellular processes, repeated DNAs, transport and binding, responsiveness to the environment, storage, translation, transcription, photosynthesis, and energy metabolism. See, e.g., MacRae et al. (1999), as well as in Bult et al. (1996), Fleischmann et al. (1995), Fraser et al. (1995), and Mathews and VanHolde (1996), as well as in references therein. Other nonlimiting examples of possible target genes that could be useful in the practice of the present invention are genes involved in any of the following additional processes: the cell cycle, cellular transport, protein binding, protein cascades, glycolysis, genes encoding or regulating transcription factors, diseases (as defined above), cancer, immune responses, organismal development, plant flowering, embryogenesis, wounding, wound healing, DNA methylation, antibiotic resistance, gametogenesis, DNA replication, aging, crop yields or productivity, fertility, longevity, period genes controlling internal organismal clocks, defense mechanisms, those genes specific to early developmental stages and genes expressed under organismal stresses.

As described herein, the invention also applies to targeted genes that are key switch genes within a biochemical pathway. The term "key switch gene within a biochemical pathway" refers to genes whose products are produced at the start of, or at a branch point of, a particular biochemical pathway; or, to genes whose expression controls the expression of other genes; or, to genes that when expressed to a certain degree result in the expression of other genes that lie downstream of them in a biochemical pathway. Key switch genes may also be those genes having any of the above described functions in cellular, enzymatic or biochemical processes. Nonlimiting examples of key switch genes include genes controlling the initiation of photosynthesis or controlling a portion of photosynthesis, genes regulating glycolysis, genes regulating oxidative phosphorylation, genes regulating stress responses, genes regulating protein cascades, et cetera (e.g., Mathews and VanHolde, 1996; also see references and diagrams therein).

In certain aspects of the the present invention, it is desirable to control the time or extent of expression of a phenotypic trait in an organism, within cells, or within specific tissues or organs. In a specific example pertaining to plants within the present invention, it may be desirable to control the time or extent of expression of a phenotypic trait in plants, plant cells, plant organs, or plant tissue(s).

In preferred embodiments of the invention, the expression of a phenotypic trait can be controlled, for example by operably linking a gene controlling the trait to an inducible promoter.

In one aspect of these embodiments, the gene whose expression is to be altered is a "targeted gene". The targeted gene may also be a key switch gene in a biochemical pathway. The targeted gene or key switch gene can be, for example, operably linked to an inducible promoter and TE transposase DNA binding motifs. A preferred example of an inducible promoter is a chemically-induced promoter (CIP), defined as a promoter or promoter region that contains at least one DNA sequence or DNA motif that can bind to a chemical ligand, wherein the binding of the chemical ligand affects the transcription of the targeted gene (usually enhancing transcription), thus resulting (usually) in increased polypeptide production from that targeted gene. An example of such a CIP is the plant salicylic acid (SA)-inducible promoter, PR-1a (Charng et al., 2000); other examples of CIPs are the tomato E4 promoter mentioned above, induced by ethylene, and the ABA-responsive promoters, discussed further below. In the particular instance of the PR-1a promoter, for example, the chemical ("C") used is salicylic acid (SA), as described in Charng et al. (2000). As defined more generally herein, however, a chemical "C" is any ligand compound that can attach to the CIP region of the targeted or the intended gene (e.g., this can also be a CIP within the effector, TE gene) and thus promote or alter that gene's expression. Other chemicals that can also attach to and regulate their cognate CIP regions within promoters are also described and referenced herein, and some of these chemicals are known plant hormones or hormone analogs, as the skilled artisan will understand to be useful in the present invention. One skilled in molecular biology will also understand that the targeted gene may contain both of: transposase DNA binding motifs (i.e., these motifs present in order to bind the TE's transposase, for example to bind to the Ac element's transposase—see "Example"), and a CIP region to bind to a chemical ligand.

The specific level of expression or the tissue specificity or the timing of expression of the targeted gene may be further controlled by a joint, synergistic interaction of both the transposase binding plus the induction of the inducible promoter, for example through the use of the specific chemical "C" binding to the targeted gene. In related embodiments, the specific desired expression of the targeted gene can only be achieved in the presence of the transposase, plus in the presence of the conditions that induce the inducible promoter, for example in the presence of the chemical "C" that binds to the CIP. The specific desired expression of the targeted gene in the present invention may, for example, be an expression induced under any condition that causes induction by an inducible promoter, for example in a specific tissue, at a specific level, at a specific time in organismal development or at a specific time during the cell cycle, at a level lower than wild type (herein described as repression), at a level higher than wild type (herein broadly defined as enhancement of expression), at a level lower than that produced by a strong enhancer (also herein defined as repression), at a level higher than that produced by a very strong enhancer (herein also defined as enhancement of expression), at a level that varies over time (a time course of expression), at a level that varies in a predictable manner over time, at a predictable ever-constant level, or, at a level that varies stochastically over time or varies stochastically over a spatial gradient. The terms "repression" of expression and "enhancement of expression" are used and defined herein as relative terms, that is, they can be used in comparison with any other level of gene expression that provides a meaningful comparative level for the analysis of gene expression.

In additional embodiments, gene regulation can be achieved through the direct regulation of the genetic element (TE) which encodes the transposase enzyme. In these embodiments, expression of the transposable element is regulated using an inducible promoter, for example a chemical control switch. In this way, the production of the transposase protein and/or the TE's RNA is controlled by the inducible promoter, for example by a chemically-induced promoter or a chemical control switch. See, e.g., Charng et al., 2000. Other TE effector molecules could also be engineered in a similar manner as in Charng et al. (2000), to also contain any number of examples of different, inducible promoters and to be rendered "non-jumping", as will be understood by the skilled artisan.

In still other embodiments, the regulation is directed at an effector element encoding the transposase (as in the chemically-controlled example system described directly above), but with two separate, interacting receptor polypeptides as well as DNA binding domains (motifs) within the effector TE element. This TE effector molecule and specifically its encoded product(s)—TE RNA and/or TE protein—can then go on to bind the transposase DNA binding motifs as located within the targeted gene's DNA, and thus regulate that targeted gene.

The present invention is also directed to methods for controlling gene expression in an organism, for example a plant. This method comprises transforming the organism with a first receptor expression cassette which encodes a first receptor polypeptide comprising a first ligand binding domain and a first DNA binding domain. The organism is also transformed with a second receptor expression cassette which encodes a second receptor polypeptide comprising a second ligand binding domain and a second DNA binding domain. In preferred embodiments, the first and second receptor polypeptides are members of the class II steroid and thyroid hormone superfamily of nuclear receptors and the first and second receptor polypeptides function together as a heterodimer. The organism is also transformed with a transposase-encoding TE expression cassette comprising a 5' regulatory region operably linked to a nucleotide sequence encoding a target polypeptide (i.e., the TE's transposase), where the 5' regulatory region comprises one or more response elements complementary to the first or second DNA binding domains of the first and second receptor polypeptides, respectively. Finally, the organism is also transformed with a targeted gene that contains transposase DNA binding motifs, preferably located within the 5' promoter region of the targeted gene.

The steroid and thyroid hormone superfamily of nuclear receptors is found in mammals and insects and is composed of over 100 known proteins. These receptors fall into at least two functionally distinct categories known as Class I and Class II (Beato, 1989; Parker, 1990). Of the two classes, only the Class II receptors function in the nucleus as heterodimers to affect expression of selected genes in the presence of hormone (i.e., in the present invention, serving to affect expression of the transposase-encoding gene). The best studied examples of Class II receptor proteins are Retinoic Acid Receptor (RAR), Vitamin D Receptor (VDR), Thyroid Hormone Receptor (T.sub.3 R) and Retinoic X Receptor (RXR). The receptors bind to the 5' regulatory region of the selected gene (e.g., a transposase-encoding construct) and, upon binding of a chemical ligand to the receptor, the transcriptional activation (transactivation) domain of the receptor affects that selected gene's expression by interacting with other transcription initiating factors.

In addition to the Class II receptor proteins found in mammals as described above, receptors of similar structure and activity have been indentified in the insect *Drosophila* (Koelle et al., 1991; Christianson and Kafatos, 1993; Henrich et al., 1990). The Ecdysone Receptor (EcR) binds the steroid hormone 20-hydroxyecdysone and, when heterodimerized with the product of the Ultraspiracle gene (USP), will transactivate gene expression. In this example the chemical "C", is the steroid hormone 20-hydroxyecdysone. The USP gene is most homologous to RXR, and RXR is capable of forming heterodimers with EcR (Thomas et al., 1993). Additional chemical ligands besides 20-hydroxyecdysone, such as other hormone agonists or antagonists, will also bind to these receptors and cause transactivation of an effector gene (e.g., herein, the transposase-encoding gene).

One member of the steroid and thyroid superfamily of nuclear receptors, the Class I Glucocorticoid Receptor (GR) which utilizes chaperonins and does not function by heterodimerization with other receptors, has also been shown to transactivate an intended gene in heterologous organisms, e.g., plant cells (Schena et al., 1991). In that work, fragment containing the ligand binding domain from GR was fused to the anthocyanin regulatory protein known as 'R' and shown to stimulate production of anthocyanin in transgenic *Arabidopsis thaliana* in response to the application of the appropriate chemical ligand (Lloyd et al., 1994). It was also reported by Lloyd et al. (1994) that full-length GR did not activate gene expression in stably transformed *Arabidopsis thaliana* whereas it did in transient assays in tobacco protoplasts. Furthermore, fusions of R with a fragment from the Estrogen Receptor (ER), another Class I receptor which utilizes chaperoning, also stimulated production of anthocyanin in the presence of the appropriate chemical ligand but showed substantial background expression. Any of these, or other, inducible systems are envisioned as within the context of the present invention.

The distinguishing feature of the Class II receptor proteins, transactivation of a selected gene by heterodimerized receptors in the presence of an appropriate chemical ligand, offer previously unrecognized opportunities for chemical control of gene expression in plants, within the present invention. The use of heterodimers allows a broader range of gene control strategies, and chemicals are already known for agricultural use which can trigger receptor-mediated transactivation of selected gene expression of this class. Furthermore, gene control strategies for plants which utilize nuclear receptors that do not occur naturally in plants have the attractive feature of inducing only the genetically engineered selected gene (e.g., herein, the transposase gene). Further modifications to this system could also be made in order to provide minimum basal transposase activity which increases rapidly to high levels in the presence of a triggering chemical. As has been demonstrated, receptor polypeptides based on the class II model, and the genes that encode them, have been developed which function in plant cells to control expression of a selected target polypeptide wherein the receptor polypeptides activate the 5' regulatory region of a selected gene's expression cassette in the presence of a chemical ligand. Such a method of controlling gene expression in plants via controlling the expression of a transposase-encoding construct is useful for controlling various traits of agronomic importance, such as plant fertility, time to flowering, crop yields, oil and protein production, and vitamin A production, each in the context of the present invention.

Where the organism used in the methods of the invention is a plant, the invention can be used in plant defense strategies. Several types of targeted genes can be used in defending the host, transformed organism against attack by another organism. The expression and specifically the levels of expression of many of such host defense-related genes can affect the ability of another, attacking organism, to harm the target organism that is being transformed; such host gene expression can also influence the ability of the attacking organism to develop resistance to the host organism's native or foreign defense-related genes. Included in this group of host defense genes are anti-herbivory genes, anti-fungal genes, anti-bacterial genes, anti-viral genes, and anti-insecticidal genes. Pesticidal proteins and *Bacillus thurengensis* (Bt)-related genes are also included within the general area of native or foreign host genes and their encoded proteins which can affect the ability of an attacking organism to harm the host, target organism being transformed. All of these terms are defined in the paragraphs that follow.

"Anti-herbivory" genes are herein defined to be targeted genes within an organism or within a collection of cells that can be used in defense against herbivores. Usually the organism is a plant or the cells are derived from a plant. "Herbivores" are defined as organisms that feed on plants or parts of plants. For purposes of the present invention "herbivores" do not include fungi. Herbivores can include grazing animals, insects, arthropods, larvae, birds, mammals, reptiles, amphibians, as well as other non-fungal species. Anti-herbivory genes include those that produce or lead to the production of chemical compounds or proteins that are noxious or poisonous to herbivores when eaten, compounds that deter herbivores from eating, compounds that smell or taste bad, compounds that produce warning coloration, compounds that make herbivores sick, compounds that drive herbivores away, compounds that are toxic to herbivores' young, compounds that lead to a decrease in herbivore survival or reproduction, as well numerous other compounds, chemicals, or proteins.

The term "anti-fungal" genes as used herein refers to targeted genes within an organism or within a collection of cells that can be used in defense against fungi. Usually the organism is a plant or the cells are derived from a plant, but they can also be non-plant in origin. Anti-fungal targeted genes can produce any number of compounds, chemicals and/or proteins to defend against fungi.

The term "anti-bacterial" as used herein refers to targeted genes within an organism or within a collection of cells that can be used in defense against bacteria. Usually the organism is a plant or animal or the cells are derived from plant or animal sources, but the organism or cells can also be fungal, or could also be from other sources.

The term "anti-viral" as used herein refers to targeted genes within an organism or within a collection of cells that can be used in defense against viruses. The organism or collection of cells can have the following origins: plant, animal, bacterium, fungus, or other organism.

The term "anti-insecticidal" as used herein refers to targeted genes within an organism or within a collection of cells that can be used in defense against insects. Usually the organism is a plant or animal or the cells are derived from plant or animal sources. Any and all members of the class Insecta are included within the methods of the present invention.

The term "pesticidal protein" as used within the present invention means a native or a foreign protein as existing within the host organism that either kills the attacking organism (a pest), or that triggers cell death responses within those pest(s) attacking the host organism. In nonlimiting examples, certain pesticidal proteins can act as nerve poisons within the attacking organism, and some pesticidal proteins can mimic naturally-occurring animal hormones. Pests are broadly defined herein as arthropods, insects, nematodes, rodents, weeds, fungi, bacteria, viruses, or other living things which are harmful to plants, animals and/or foodstuffs. Arthropod pests include insects or arachnids such as Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, and Acari. In a particularly preferred embodiment, the insect is a Coleoptera or Lepidoptera. In more preferred embodiments, the insect is selected from the group consisting of black cutworm (*Agrotis ipsilon*), fall armyworm (*Spodoptera frugiperda*), beet armyworm (*S. exigua*), yellow striped armyworm (*S. ornithogalli*), southwestern corn borer (*Diatraea grandiosella*), sugarcane borer (*D. saccharalis*), corn earworm (*Helicoverpa zea*), mediterranean corn borer (*Sesamia nonagroides*), cabbage looper (*Trichoplusia ni*), velvetbean caterpillar (*Anticarsia gemmatalis*), diamondback moth (*Plutella xylostella*), and tobacco budworm (*Heliothzis virescens*). The terms "anti-dipteran", "anti-lepidopteran", "anti-coleopteran", and "anti-hymenopteran" as used herein, refer to host defense-related genes or to similar host proteins that are directed against that particular group of organisms named (e.g., Diptera, Lepidoptera, Coleoptera, Hymenoptera, etc.)

The term "*Bacillus thurengensis*-related" or "Bt-related", as used herein, refers to a particular type of targeted gene originally derived from the bacterium *Bacillus thurengensis*, a gram-positive spore forming microorganism, namely a .delta.-endotoxin (crystal protein) gene. Varieties of Bt are known that produce more than 25 different but related .delta.-endotoxins, toxins whose activity can be very high, thus requiring only small amounts to be effective. Bt strains produce .delta.-endotoxins during sporulation. The majority of delta.-endotoxins made by Bt are toxic to larvae of certain insects in the orders Lepidoptera, Diptera, and Coleoptera, but they have no known harmful effects on humans, other mammals, birds, fish, or on insects within other Orders. Some of these .delta.-endotoxins have useful insecticidal activities against different insect pests. The specificity of the Bt endotoxins is dependent, at least in part, on both the activation of the toxin in the insect gut (Haider et al., 1986) and its ability to bind to specific receptors present on the insect's midgut/hindgut epithelial cells (Hofmann et al., 1988). Chimeric Bt toxin genes (containing a mixture of Bt-genes and other, non-Bt genes) are also included within the scope of the present invention.

The term "stomate opening-related" genes as used herein, refers to those targeted genes involved in, or which can be used to modify, plant transpiration, specifically genes controlling the opening and closing of stomates present on the underside of the leaf. The loss of water in plants may be so undesirable as to limit key metabolic processes associated with plant growth and development. Such water loss in plants, in the form of transpiration, occurs through the stomates and is controlled by the size of the stomatal opening. Stomatal conductance is a measure of the width of stomates on the underside of the leaf. The greater the size of the stomatal opening, the greater is the stomatal conductance, and so transpiration (water loss) is greater. In order to limit transpiration rates, the present invention seeks to control those targeted genes involved in the leaf stomatal opening process. By genetic repression of the stomate pore opening mechanism through methods of the present invention, this is one way for the plant to conserve its water in times of drought or water shortage.

In some embodiments, the invention can be used in controlling water relations in plants. It is sometimes the case that a finite amount of water is available following winter rain and it is advantageous to restrain plant growth so that water resources are not exhausted before the valuable portion of the crop has developed. For instance, wheat sown after winter rain must set grain before the soil water is exhausted. Vegetative plant growth and especially transpiration of water must be restrained. Reduced expression or activity of the cell cycle gene $p34^{cdc2}$ or of other appropriate cell cycle genes could achieve reduced plant growth without the toxic side effects produced by chemical agents which simply reduce transpiration. Reduced expression or activity of $p34^{cdc2}$ or of other appropriate cell cycle genes may be accomplished in any number of ways, particularly via the methods of the present invention.

In addition, a large number of plant genes that are expressed in response to the environment may be useful within the context of the present invention, either useful as targeted genes and/or as key switch genes in a biochemical pathway, and/or as genes containing a chemically-induced promoter (CIP), these terms as defined above. Specifically, genes involved in plant responses to heat stress, water stress, and ABA treatments have now been well-characterized (U.S. Pat. Nos. 5,071,962; 4,797,359; Baker et al., 1988; Harada et al., 1989; Hong et al., 1988; Hughes and Galau, 1991; Mundy et al., 1990; Raynal et al., 1989; Vilardell et al., 1990). For simplicity of nomenclature, the group of water stress proteins is referred to as WSPs. These proteins were originally identified as LEAs, RABs, and dehydrins. LEAs (late embryogenesis abundant proteins) are, as their name implies, expressed at high levels during the latter stages of seed development and programmed seed dry-down (Dure et al., 1989). Dehydrins and RABs (responsive to ABA) are similar to LEAs in several ways: hydrophilicity (>55% hydrophilic residues), responsiveness to ABA treatments, boiling solubility, a general absence of cysteine and tryptophan residues, and the presence of repeating motifs. Most of these proteins range in size from 10 kDa to 40 kDa. The methods of the present invention may be applied to any of the water stress, heat stress, cell cycle, ABA responsive, or other genes described above so as to conserve plant water resources and/or to inhibit unnecessary plant growth during times of drought or stress, either by means of controlling stomate opening and/or by other, appropriate means. Further key proteins of use in the present invention are those recently found to be involved in plant freezing responses and drought tolerance, i.e., the CBF and DRB proteins (Amber, 2000).

All of the gene promoters previously described are also useful for these embodiments.

The methods of the present invention are useful whether the effector molecule and/or the targeted gene are either native to the organism being transformed (a "native gene" or native "polynucleotide"), or are foreign to the organism being transformed (a "foreign gene" or "recombinant polynucleotide"), or are a mixture of native and foreign genes.

As used herein, the term "polynucleotide" refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded ribonucleic acids (RNA) and deoxyribonucleic acids (DNA), and may include polymers having backbone modifications such as methylphosphonate linkages. A "recombinant polynucleotide" as defined herein intends a polynucleotide of genomic DNA, cDNA, or RNA, semisynthetic or synthetic in origin, which, by virtue of its origin or manipulation (for example, by endonucleases): (1) is not associated with all of or with a portion of a polynucleotide with which it is normally associated in nature, (2) is linked to a polynucleotide other than that to which it is linked in nature, and/or (3) does not occur in nature. The term "native gene" as used herein refers to a gene as found in nature. The term "foreign gene" herein refers to any gene that contains (1) regulatory and coding sequences that are not found together in nature, or (2) sequences encoding parts of proteins or polypeptides that are not naturally adjoined in nature, and/or (3) parts of promoters that are not adjoined in nature. Accordingly, a "foreign gene" as used herein may comprise regulatory sequences and coding sequences that are derived from different sources, or, it may comprise regulatory sequences and coding sequences derived from the same source, but arranged in a manner different from that which is found in nature.

The methods of the present invention are also useful whether the effector molecule and/or the targeted gene are stably or only transiently expressed within the organism or cells. As used herein, the terms "transiently expressed" and "transient expression" refer to cells or organisms into which foreign DNA has been introduced (by such methods as electroporation/transfection, transformation, Agrobacterium-mediated transformation, or biolistic bombardment), but those cells or organisms do not maintain the DNA over long time periods (e.g., the introduced DNA usually does not incorporate into the cell's chromosomes). Also as used herein, the terms "stably transformed", "stably expressed", and "stable expression" refer to cells or organisms in which the introduced DNA does maintain itself over a long time period, or, is retained within the cell or organism (e.g., the introduced DNA usually does incorporate into the cell's chromosomes, and it can incorporate into multiple chromosomal locations, in several copies).

Applications

It is envisioned that the present invention will have several practical uses. Nonlimiting examples of these uses are: (1) a method of repressing transcription of genes in vitro; (2) a method of repressing transcription of genes within transplanted (or grafted) plant or animal organs or body parts; (3) a method of producing a general repression of transcription of many genes (not just of a single targeted gene); (4) a method of generating a facile conditional gene expression system; (5) a method for defining and describing global (whole genome) mRNA gene expression profiles at organ, cellular, and subcellular levels under various environmental conditions using transposable elements; (6) a method for analyzing and documenting the effects of transposable elements on whole-genome gene expression patterns via the use of DNA chips or microarrays; (7) a method for identifying the transposable element-related cis regulatory sequences of all genes; and (8) a method for identifying the regulatory circuits controlled by each single transposable element, when it is acting as a transcription factor or transcriptional regulator (9) achieving different degrees of transcriptional repression (strong, moderate, or mild); (10) inducing the repression of genes involved in "anti-X" functions, where X is a biological process or function and X can be replaced by the words: herbivory, fungal, viral, bacterial, insecticidal, Bacillus thurengensis endotoxin gene-related, acarian, and stomate opening-related; (11) producing a population of animals or plants that vary in their expression of a desired gene; (12) producing a general toxicity or the shutting down of many genes at once, within a plant or an animal, or within a plant cell or an animal cell; (13) inducing the transcriptional repression of one targeted gene, by introducing a transposase molecule into the cell; (14) inducing a non-specific repression of many genes within a cell by introducing a transposase molecule into a cell; (15) producing a repression of mRNA translation within a cell, either of a single gene's mRNA, or, of several genes' mRNAs; (16) producing either a calculable increase or a calculable decrease in gene transcription by means of the present invention; (17) producing a repression of the transcription of genes involved in antibiotic resistance; (18) producing a repression of the transcription of genes within human gametes; (19) achieving a repression of gene expression in those genes involved in DNA methylation; (20) achieving a repression of gene expression of those genes expressed in the cell cytoplasm, by directing the transposase to, and/or expressing the transposase in, the cytoplasm; (21) achieving a repression of gene expression of those genes normally expressed in a particular cellular organelle, by directing the transposase to, and/or expressing the transposase in, that specific organelle; and (22) producing a repression of gene expression at specific times or during specific stages of the cell cycle by means of the present invention.

The first eight examples of practical uses of the present invention are each now explained in greater detail. By these explanations, the skilled artisan could easily envision how the remaining examples could be achieved.

In the first example, a method for repressing the transcription of genes in vitro, a kit is contemplated. The kit would comprise at least two containers. The first container would contain an Ac transposase-encoding polynucleotide molecule (or another, appropriate transposase-encoding polynucleotide molecule, besides Ac), such that it provided a source of the transposase enzyme capable of producing gene repression. The second container would contain a target gene whose expression is to be modified, operably linked in cis to short Ac or to other appropriate transposase binding site DNA motifs. To utilize the kit, the two components are transfected into cells. The target ene can be expressed by induction of the transposase gene. A related transposase kit, would be used a method for inducing specific, planned deletions within genomes and genes, similar to the TREGED strategy for inducing deletions in plant genomes, but with increased location and deletion sequence specificity.

The second example is a method of repressing transcription of genes within transplanted (or grafted) plant or animal organs or body parts. In these embodiments, the tissue is transfected with a transposase gene that will suppress a target gene or genes in the transplanted tissue. It is envisioned that a grafted tissue rejection response could be more easily avoided if appropriate genes were turned off or repressed within either the transplanted organ/body part, or, within the main portion of the plant or animal. It is known that tissue rejection is less likely to occur if the two tissue types are either completely compatible, or, if the foreign proteins (antigens) produced by the transplanted/grafted organ are minimized. By repressing genes either selectively or in total (global gene repression), the severity of a rejection response may be lessened, or, such a response might be avoided. The proteins necessary for proper functioning of the grafted tissue or organ would then be supplied appropriately in trans by the main part of the plant or animal.

A third embodiment, a method of producing a general repression of transcription of many genes (not just of a targeted gene). Here, it is envisioned that many gene promoter regions would contain sufficient numbers of transposase DNA binding motifs (for example, Ac hexamers, tetramers, and triplets) to effect the gene repression of multiple genes, since the inventor has found that there are transposase binding motifs within many promoters. To fully carry out this method, the transposase would also need to be produced and made available in sufficient quantities to bind to all of, or to many of, those DNA binding motifs. A DNA-demethylating agent would in most cases also need to be applied in the proper quantity and manner to the organism whose overall transcription was to be repressed, or, that a stress might have to be applied to the organism (e.g., heat stress, cold stress, mechanical stress—touch—, or hormone-induced stress) in order to demethylate a subset of its transposase binding motifs. This would then allow the transposase to bind to the DNA motifs or to a subset of such motifs (now unmethylated); but, this demethylation occurring would not be so extreme or widespread as to de-repress (i.e., to activate) all of the very suites of genes which one was trying to repress. Thus, a fine tuning would need to be achieved, between some demethylation of gene promoters and their transposase binding motifs, and the production of sufficient quantities of the transposase to permit its binding to those specific transposase motifs within gene promoter regions. Such fine tuning would be expected to achieve the desired level of general gene repression for the desired period of time. It is known that transposons such as maize Spm undergo such reversible and transient demethylation of subsets of DNA motifs within the Spm promoter region; thus, such a proposal involving the transient demethylation of non-transposon (gene) promoter regions would also be expected to work.

A fourth embodiment, a method of generating a facile conditional gene expression system, is important for gene control. As previously discussed, the transposase and the targeted gene(s) could each be placed under the control of such an on/off gene switching mechanism. Such a switching mechanism (i.e., a facile conditional gene expression system) would employ an inducible promoter such as a hormonal switch, a chemical switch, a switch requiring the interaction of two separate proteins, or other switches as previously discussed.

A fifth embodiment is a method for defining and describing global (whole genome) mRNA gene expression profiles at organ, cellular, and subcellular levels under various environmental conditions using transposable elements (TEs). This method preferably comprises the following steps: (1) Obtain a library of cDNAs whose biochemical functions are known. The cDNAs are preferably immobilized, for example on microarrays. The cDNA preparations should represent genetic expression of a condition under study, e.g., a particular tissues under particular environmental conditions. This is not limited to any particular tissue or any organism. (2) Create a transgenic stable line of the organism, either a cell culture, tissue culture or the entire organism) containing only 1 copy of the transposase gene under the control of a strong promoter switch, such that the transposase gene could be turned on and off in a controlled manner. Such a stable line could be generated de novo, or, obtained from a known source. (3) Extract two or more separate mRNA populations (samples) from the stable line, at least one sample taken before transposase induction and at least one sample taken after transposase induction. (4) Reverse transcribe the above samples of mRNA into two or more cDNA populations, (i.e., if more than two mRNA samples were taken at step 3 above), one reverse transcribed cDNA population per each mRNA population sampled; label each cDNA population with different markers, for example fluorescent tags. (5) Probe/hybridize the cDNAs from step (1) above simultaneously with the two differently tagged populations of cDNAs, i.e., from the "+transposase" expressed sample and from the "−transposase" expressed sample. (6) Observe any increases or decreases in certain genes' expression patterns, e.g. on the microarray plate(s), in response to induction versus lack of induction of the Ac transposase, as measured by hybridization of the differing cDNA populations to the immobilized microarray(s). Taking such a time course initially—i.e., done at step 3, above— will also allow one to determine which genes are directly regulated by Ac (e.g., are activated or repressed early on), and, which genes are regulated only indirectly (e.g., are activated or repressed later in time), in response to Ac transposase production. By hybridizing the "+Ac" cDNAs taken from different time points (step 3) to the immobilized microarray(s), temporal differences in gene expression can be identified. This method allows the identification of genes that are most strongly affected by the transposon insertions.

Another embodiment is a method for analyzing and documenting the effects of TEs on whole-genome gene expression patterns via the use of DNA chips or microarrays. This method is similar to the method described immediately above, except it employs everal transposases to determine differences between them in their effect on gene expression.

Another modification of the methods described immediately above is a method for identifying the TE-related cis regulatory sequences of all genes. In order to know which promoter DNA sequences to target for a transposase's binding to, and for their use in gene regulation kits, it is important to investigate the full range of short DNA sequences to which a given transposase can bind. To do this, a preferred method comprises the following steps. (1) total genomic DNA from a given organism is mechanically or enzymatically cleaved into small pieces (about 25 bases or smaller-sized fragments); (2) such DNA fragments or pieces are then be allowed to bind to the transposase of interest in a DNA-protein binding assay; (3) once such binding had occurred, those bound DNA-protein complexes are isolated (purified); (4) next, those bound DNA fragments are dissociated; (5) those DNAs are then sequenced; (6) next, the DNA sequences from several such bound "DNA-protein" fractions are compared to one another, to determine which DNA sequences are in common across different fractions; (7) those DNAs in common to the different bound fractions are then cleaved into even smaller fragments; (8) repeat steps 2–7 above, each time removing (cleaving off) those portions (internal or external sections) of the bound DNA fragments that did not contain any sequences in common with any of the other bound fractions, until the least common denominator of "short DNA sequences bound by the transposase" is determined. This method is important for the development of several "transposase-bound DNA target" systems of interaction for the specific regulation of gene expression within several organisms, using many different transposases.

A further embodiment of the invention is a method for identifying the regulatory circuits (i.e., the biochemical pathways) controlled by each single TE when it or its encoded transposase protein is acting as a transcriptional regulatory factor. Such regulatory circuits could be identified by the use of the method described above for defining and describing global mRNA gene expression profiles. Once those genes that are turned on and off in response to a transposase's overexpression are identified, then one can piece together what biochemical pathways those affected genes belong to. Thus, if for example several genes involved in glycolysis or involved in energy metabolism were affected by Ac transposase overexpression (as detected via analyses of microarray expression patterns), one could then use that type of information to discover which such major biochemical pathways were primarily affected by transposase-based gene regulation, and, which pathways are affected by which transposases. One could further determine if some of those biochemical pathways are profitably altered to produce more protein, more starch, more oil content, enhanced disease-resistance, higher crop yields in stress environments, the enhanced ability to grow in drier or in light-limited environments, or, if they could be altered so as to affect any other desirable plant or animal trait(s) of economic importance, through means of the present invention.

The present invention could also be used to discover new gene functions (of genes whose functions are as yet unknown) within these several organismal systems. For example, heterologous introductions of a transposase into animals would also lead to numerous "knock-in" gene models, where those several genes disrupted by the introduction of the transposase, (i.e., those genes caused to have increased or decreased expression due to an "knock-in"), could then be examined for their function(s), and to see if they had any related biochemical or mutant phenotypic functions that appear de novo after introduction. In this way, transposase introduction would be like a perturbation of the stable genetic system, and one could examine what effect was produced by such a perturbation or introduction of Ac into specific genes of unknown function. The functions of those gene sequences in humans whose protein products are unknown, for example, could be inferred directly from such "knock-in" studies, or also indirectly, from similar functions determined in other model animal systems. A generally similar approach can be used to determine the effect of any genome component X on any genome component Y; an example of the general use of this type of experimental procedure is given in Marx (2000) as used by Plasterk to determine the effect of RNAi on transposons.

An additional preferred embodiment of the present invention is methods for treating an organism with a disease. The method comprises altering the expression of genes involved in the disease. In the context of the present invention, the term "disease" is broadly defined as being a state of unhealthiness or reduced health of any organism or organ or group of cells therein, usually ultimately characterized by a defined set of symptoms of abnormality. Disease implies a deviation from normality of an organism or of an organ or of a group of cells from an organism. It can result in a morbid or mortal condition of the body or some part of the body or some organ of the body. It is also sometimes referred to as illness, sickness, or ailment, and it can be of a genetic origin. Disease can also be defined broadly as a malfunctioning of the body or any part of the body resulting from any number of influences, including genetic errors, toxins, infections, nutritional deficiencies, and environmental factors.

In any of the above-described methods where plants are involved, preferred embodiments include Ac stable transformation within plants and plant cells, as well as transient expression. Both stable transformation and transient expression (transformation) methods and systems have been developed for many key plants of agronomic, commercial, and/or scientific value. See, e.g., cotton (Perlak et al., 1990), soybean—including the somatic embryogenesis and cotyledonary node transformation methods—(Finer and Finer, 2000; Terce-Laforgue et al., 1999; Falco et al., 1995; Li et al., 1997; Stewart et al., 1996; Potikha et al., 1999), maize— corn—(Lyznik et al., 1989; Fromm et al., 1986), rice (Goto et al., 1999; Cornejo et al., 1993; Shimamoto et al., 1993; Yin et al., 1998; Izawa et al., 1997), alfalfa (Schoenbeck et al., 2000; Wandelt et al., 1992; Gowri et al., 1991), wheat (Altpeter et al., 1996; Blechl and Anderson, 1996), cereals (Barcelo et al., 1994), *Lotus corniculatus* (Terce-Laforgue et al., 1999; Vincent et al., 1997), legumes (Chowrira et al., 1995; Trieu et al., 2000), tomato (Carroll et al., 1995), petunia (Elomaa et al., 1995), potato (Borkowska et al., 1998), canola (Falco et al., 1995), tobacco (Yamamoto et al., 1995; Ealing et al., 1994; Wandelt et al., 1992; Bustos et al., 1991; Sautter et al., 1991; Van Houdt et al., 2000; Wang et al., 2000c), *Arabidopsis* (Potikha et al., 1999; Quaedvlieg et al., 1998; Stromvik et al., 1999), white clover (Ealing et al., 1994), barley (Cho et al., 1999), pear (Lebedev and Dolgov, 2000), as well as for selected plant pathogens (Chaure et al., 2000; van West et al., 1999), and for plant cells and plant organelles (Terzaghi and Cashmore, 1997; Heifetz, 2000; Shiina et al., 2000). Additional methods of transformation (transfection) for plants as well as for mammalian cells can be found in Keown et al., 1990 and in Chung et al., 1999.

In preferred embodiments, such stable and transient transformation discussed above involves the introduction of a TE plasmid construct (e.g., for instance the Ac wx-m9 or wx-m7 plasmid constructs described in Example 1) into the plant genome of choice; for stable transformation, such introduction is then followed by a double cross-over genetic event to introduce the genetic element stably into the plant's own chromosomes. A selectable marker for plants such as hygromycin or neomycin resistance is preferably provided to select for transformants.

A further preferred aspect provides an optimized number of the appropriate short, transposase DNA binding motifs, as used within the reporter or the targeted gene construct so as to produce the greatest possible gene repression effect (i.e., FIG. 1A and accompanying text). However, an even greater number of such transposase binding motifs, up to and including approximately 1,000 such short DNA motifs, and also including hexamers and tetramers as well as triplet motifs (or longer DNA sequence motifs, as needed for different TEs and their respective transposases), would be one of the preferred embodiments. The exact, optimal spacing of such transposase binding motifs (e.g., for instance, with five to twelve bases existing between the binding motifs, as discussed in Becker and Kunze (1997), and as discussed in the "Example") to produce the maximum repression effect for each transposase used, is also a preferred embodiment.

In some embodiments, it is desirable to not have any "transposase self-repression" phenomena occurring; in other words, within the promoter which is used to drive the transposase's expression from within the effector construct (see, e.g., Example 1), there could exist specific cognate transposase binding motifs. If a different promoter, lacking such cognate transposase binding motifs were used, such "transposase self-repression" phenomena could be avoided and thus more transposase could be produced. In other words, we are attempting to avoid the transposase being produced and then participating in a feedback loop, where it then binds to its own promoter region and represses its own continued production. For monocots, a suitable alternate promoter could be the ubiquitin promoter. A preferred embodiment would thus be to simply remove or to replace any known or presumed transposase binding motifs (hexamers, triplets, tetramers or other such motifs) from within the effector construct's own promoter region.

Also concerning obtaining the maximum possible repression effect vis a vis DNA methylation, the preferred embodiment (described in the Methods section, in the "Example") is to passage all plasmid constructs through an appropriate cell line that would assure that the plasmids are not methylated prior to their transformation into plants, plant cells, animals, animal cells, fungi, fungal cells, or other living organisms. Commonly used for this purpose are JM110 $E.$ $coli$ bacterial cells (dam$^-$, dcm$^-$). This step will avoid potential complications (i.e., lack of transposase-to-DNA binding and/or lack of transposase message production) due to effector or reporter DNA methylation. Such problems could be encountered by either DNA methylation of the transposase binding motifs within reporter constructs, or, by DNA methylation of the transposase's DNA coding region within the effector construct. The complications can be avoided by JM 110 construct cell passaging. Other cell lines for this purpose are also known in the art.

The Ac repression phenomenon observed (see "Example") may extend to other members of the hAT gene family or "Ac superfamily", as discussed in the "Example" and also as described in (Alatortsev et al., 2000) (i.e., reporter gene repression by P elements). These "Ac superfamily" members include the $Drosophila$ P elements, $Drosophila$ Hobo elements, the Antirrhinum (snapdragon) Tam3 elements, as well as other transposable elements also referenced and diagrammed by their multiple alignments, in figures within Kunze et al. (1997). Preferred embodiment also include the introduction of these other "Ac superfamily" transposable element members into appropriate heterologous plant or animal systems, via transformation techniques. Certain of these alternate "Ac superfamily" members may provide an increased level of target gene repression, above that observed strictly for the maize Ac element itself, due to their differing amino acid sequences and amino acid functional motifs.

Preferred embodiments also include introduction of the reporter and effector constructs into plants and animals on separate plasmid vectors ("reporter" and "effector" plasmids separately) as described within the attached example, as well as on the same plasmid vector. This will be done because increased effects on gene expression (e.g., increased repression) can sometimes constructs were obtained by the following methods: (1) PCR amplification to generate inserts, followed by (2) directional cloning of the inserts into HindIII and NcoI sites contained within a ~4.9 kb p35S-65G vector (Yanhai Yin, personal communication; FIG. 1A). The p35S-65G vector contains the complete coding sequence for the gusA gene, located directly 3' to an NcoI site (FIG. 1A).

The third expression vector construct (reporter), called "CaMV 0.7-GUS", also contains a HindIII/NcoI insertion, of a ~0.7 kb CaMV 35S native promoter region, within the p35S-65G vector described above (FIGS. 1A, 3). This "CaMV 0.7-GUS" construct contains 34 Ac element-related triplet sequences within the native CaMV 35S promoter region (either 5' ACG 3' or 5' TCG 3'), as well as tetramers known to be able to bind the Ac transposase (FIG. 3; Benfey et al., 1990a, b).

To amplify the insert contained within the "T1R-90-GUS" construct, the following primers were used: 5' GATAGGAAGCTTAAACGGATCTCCACTGACG-TAAGGGATG 3' (SEQ ID NO:1)(a 40-mer) and 5' GATTTCACGGGTTGGGGTTTCTA 3' (SEQ ID NO:2)(a 23-mer from within the 5' region of the gusA gene). To amplify the insert contained within the "-90-GUS" construct, the following primers were used: 5' GATAG-GAAGCTT ATCTCCACTGACGTAAGGGATG 3' (SEQ ID NO:3)(a 34-mer) and 5' GATTTCACGGGTT GGGGTTTCTA 3' (SEQ ID NO:2) (the same 23-mer as above). Underlined sequences within the primers above are HindIII recognition sites, and the sequence in bold within the "T1R-90-GUS" primer is the hexamer that can bind strongly to the Ac transposase. PCR conditions were: 94° C., 1 min., 1 cycle; followed by [94° C., 30 sec., 60° C., 30 sec., 72° C., 2 min.] 1 cycle, 4° C. hold. Template DNA (240 ng) used in PCR reactions was the "CaMV 0.7-GUS" construct described above. Amplification reactions used 2 mM $MgCl_2$, 0.4 mM dNTPs, 1X PCR buffer, 60 pmoles of each DNA primer, and 0.2 units of Taq polymerase. be achieved when the rates of simultaneous co-transfection from two different plasmids do not have to be taken into effect.

Transformation methods include the preferred embodiment via electroporation, as well as the most efficient and stable methods of plant transformation that are appropriate for each system to be used.

Preferred embodiments of the invention are described in the following examples. Other embodiments, as well as extensions of the present embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. The following examples are offered by way of illustration, not as a limitation in any sense.

EXAMPLE 1

Demonstration of an Ac TPase-induced Gene Repression Effect in a Plant Cell System Materials and Methods Generation of the gusA Reporter, Ac Effector, and pUC18 Effector Constructs Used i. Reporter Constructs The two gusA expression vector constructs (reporters) are called "T1R-90-GUS" and "-90-GUS". They contain the CaMV 35S -90 native promoter region (Benfey et al., 1990a,b) a promoter which includes 5 copies on either strand of the minimal triplet sequences present within Ac element terminii and known to be involved in binding of the maize Ac element transposase (triplets: 5' ACG 3' or 5' TCG 3'; FIG. 3; Becker and Kunze, 1997). In addition, the "T1R–90-GUS" construct contains 1 repeat copy (T1R) of the Ac hexamer (5' AAACGG 3') (which binds strongly to the Ac transposase; FIG. 1A). These two Following amplification, products of the predicted sizes were excised and purified from 2.3% agarose using the "Mermaid" DNA purification kit (Bio101/Quantum Biotechnologies). Purified products were double-digested with HindIII and NcoI, run on 2.3% agarose gels, and digested fragments were again gel purified using the "Mermaid" kit. HindIII-NcoI insert fragments were ligated into the HindIII-NcoI double-digested, phosphatase-treated p35S-65G vector, using a 3:1 excess insert molar ratio.

Correct insertions within the "–90-GUS" and the "T1R–90-GUS" constructs were verified by HindIII-NcoI digestion and dideoxy-automated ABI sequencing of insert regions. The "CaMV 0.7-GUS" insertion size was verified by HindIII-NcoI digestion followed by agarose gel electrophoresis; its orientation had been previously verified (S. Dai, personal communication).

All 3 reporter constructs were passaged through JM110 (dam⁻, dcm⁻) $E.\ coli$ cells prior to preparation of plasmid DNA for use in transfections. This was done to avoid potential problems, such as inefficient Ac transposase binding, that might be caused by DNA methylation properties of reporter sequences. Reporter construct insert sequence verification (via ABI sequencing) was performed after constructs had been passaged through JM110 cells. Plasmid DNA extraction and purification was performed using the Qiagen MaxiPrep Kit.

ii. Ac Effector Construct and pUC18 "Mock Effector" Construct

To generate the Ac effector construct called pLau6-Ac (FIG. 1B), the 3.2 kb coding region from the maize Ac wx-m9 allele was inserted into the pLau6-GUS plant expression vector containing a CsVMV promoter (Verdaguer et al., 1996) and a Nos terminator sequence.

To verify that the maize Ac wx-m9 coding region (Pohlman et al., 1984) is identical in sequence to that of the Ac wx-m7 allele obtained by Behrens et al. (1984) and Muller-Neumann et al. (1984) and used in transgenic rice experiments by Izawa et al. (1997), the ~200 bp exon II region of Ac wx-m9 was resequenced. The sequences of all intron/exon splice junctions within the Ac wx-m9 allele were also verified.

To obtain the wx-m9 maize Ac 3.2 kb coding region in the correct orientation within the pLau6-GUS plant expression vector, these steps were taken: (1) the complete maize wx-m9 Ac element was subcloned as a 4.8 kb PstI insert from within a pyAc construct (J. Messing, personal communication) into a pUC118 vector; (2) the pUC118 Ac-containing PstI clone was digested with BanII and XmnI, releasing a 3.2 kb BanII fragment containing the entire Ac coding region; (3) this fragment was treated with the Klenow fragment of DNA Polymerase I at 25° C. at a concentration of 1 unit Klenow enzyme/μg DNA (New England Biolabs), to remove 3' BanII overhangs; (4) the plant expression vector pLau6-GUS, which contains the cassava vein mosaic virus (CsVMV) promoter and the Nos terminator (Verdaguer et al., 1996; pLau6-GUS construct by Laurent Gillot, 1996), was digested with EcoRI and BglII. The EcoRI-BglII digested 3.5 kb "vector-only" fragment was gel-purified and treated with the Klenow fragment of DNA Polymerase I, as above; (5) both Klenow-treated fragments (i.e., pLau6-GUS vector and Ac 3.2 kb insert) were precipitated. The pLau6-GUS vector fragment was further treated with CIAP (Gibco-BRL) to inhibit self-ligation and was then re-precipitated; (6) the two blunted fragments, insert and vector, were ligated in a 3:1 excess insert molar ratio, using the Fast-Link DNA ligation kit (Epicentre Technologies); (7) after heat inactivation of the ligase, ligation products were transformed into competent DH5α cells; (8) bacterial colonies were grown on Ampicillin plates and Ampicillin-resistant clones were subsequently grown in liquid culture. Plasmid clones were checked for correct Ac insert size and orientation with respect to the CsVMV promoter via double-digestion with EcoNI and PvuI, as well as by double-digestion with EcoNI and BamHI; (9) a clone of correct size and orientation, called pLau6-Ac (FIG. 1B), was passaged through JM110 $E.\ coli$ cells (dam⁻, dcm⁻). This was done to avoid potential complications due to effector clone DNA methylation; finally (10) JM110-passaged DNA was re-checked for Ac insert size and orientation. Large scale DNA preparations of the pLau6-Ac effector clone were conducted via the MaxiPrep kit (Qiagen).

The pUC18 plasmid DNA used as a "mock effector" clone was obtained from New England Biolabs. It was also passaged through JM110 $E.\ coli$ cells, as above.

BY-2 Cell Maintenance Protoplast Preparation and Protoplast Transfection Procedures BY-2 tobacco cells used to generate protoplasts were maintained in continuous liquid stock culture, shaking in the dark. Cells were shaken at ~175 rpms at 26° C. Cells were maintained in a maintenance medium and were subcultured via a 1:20 cell dilution every 7 days, as described in Bhattacharyya-Pakrasi et al. (1993), Heinlein et al. (1998), Osbourn et al. (1989), and Reichel and Beachy (2000).

To prepare protoplasts for use in subsequent transfections, a 1:10 dilution of the BY-2 stock culture above, was made 3 days prior to protoplast preparation. As described in Bhattacharyya-Pakrasi et al. (1993), Heinlein et al. (1998), Osbourn et al. (1989), and Reichel and Beachy (2000), cells were washed with 0.4 M mannitol, digested with protoplast enzyme solution, re-washed with 0.4 M mannitol, and counted using a hemocytometer. A total of $0.5 \times 10^6$ protoplast cells were used per transfection.

Each transfection treatment consisted of adding a "transfection DNA cocktail" to protoplasts via electroporation. The cocktail contained a constant reporter DNA amount (7 μg) and an appropriate amount of effector DNA (the pLau6-Ac or pUC18 effector), to make a 5:1 effector: reporter molar ratio in all treatments. Herring sperm DNA was added to all cocktails (including "no effector" treatments), so that total DNA amount per cocktail in all treatments was 85 μg (FIG. 2; Table 2). BioRad 0.4 cm Gene Pulser cuvettes and the BioRad Gene Pulser II electroporation unit were used for transfections. Transfection and protoplast culturing procedures are further described in Bhattacharyya-Pakrasi et al. (1993), Heinlein et al. (1998), Osbourn et al. (1989), and Reichel and Beachy (2000).

Measurement of Protein Concentration and GUS Activity From Transfected Cells

After transfection, these steps were taken: (1) BY-2 cells were collected 24 hrs. post-transfection; ~200 μl of cells were stained with fluorescein diacetate (0.5 μg/ml in protoplast culture medium, from a stock of 5 mg/ml in acetone) and observed with an Olympus CK40 microscope (25×) to confirm protoplast condition and lack of other cellular contamination in each treatment; (2) the rest of the cells were spun down, resuspended in 150 μl GUS Extraction Buffer (GEB) (Jefferson, 1987), and stored at −70° C.; (3)

cells were thawed at 37° C., then flash-frozen in liquid nitrogen; step 3 was repeated 3×; (4) cellular debris was pelleted by spinning at high speed; the liquid fraction was transferred to new tubes; (5) Bradford reagent (BioRad) was diluted 1:4 with water; 5 µl of each sample from step 4 was added to 195 µl diluted Bradford reagent in a clear microtiter plate; BSA standards were used; each well contained 200 µl total volume; (6) Absorbance (595 µm) was measured with a Spectra Max Plus spectrophotometer (Molecular Devices) and SOFTmax PRO 2.6.1 program; (7) total protein concentrations (µg/µl) were obtained; equal protein amounts per sample were added to wells of a black microtiter plate; (8) GUS Assay Buffer (GAB) (Jefferson, 1987) (at 37° C.) was added to each sample to make 250 µl; GUS Extraction Buffer (250 µl) was used in the "blanks"; (9) the Spectra Max Gemini (Molecular Devices) and SOFTmax PRO 2.6.1 program were used in fluorescence and kinetic modes, to measure GUS activity (RFU/sec) at 37° C., with excitation at 365 nm/emission at 455 nm, the 2 wavelengths for detecting GUS activity (Jefferson, 1987; S. Dai and I. Ordiz, personal comm.) Sufficient experimental detail is given, such that these experiments could be repeated and confirmed.

Results

Experimental Design

To test whether the maize Ac transposase can regulate gene expression in transient assays, I conducted a sequential series of 4 experiments (A–D), in which the Ac transposase gene region (i.e., the Ac effector molecule; FIG. 1B) was introduced into tobacco BY-2 protoplasts together with one of three different promoter constructs (FIG. 1A) via electroporation (transfection). The three different promoter constructs each contain the gusA (GUS) reporter gene, but they have differing promoter regions. The promoter constructs are designated: −90-GUS; T1R–90-GUS; and CaMV 0.7-GUS (FIG. 1A). The −90-GUS construct contains the native CaMV 35S −90 to +8 truncated promoter region; the T1R–90-GUS construct contains one copy of the Ac transposase binding site (hexamer) repeat AAACGG plus the native CaMV 35S −90 to +8 promoter region; the CaMV 0.7-GUS construct contains the longer, native CaMV 35S 0.7 kb promoter sequence, which also includes the −90 to +8 CaMV 35S promoter region (FIG. 3).

GUS enzyme activity levels (RFU/sec or, i.e., Vmax) were monitored with and without Ac effector molecule presence (Tables 1, 2; FIG. 2). As a control, pUC18 "mock effector" vector DNA alone was introduced together with each of the three promoter constructs described above (FIG. 2; Table 2). A total of 32 separate transfection reactions were conducted in the research reported here (Tables 1, 2; FIG. 2), across 4 separate experiments (A–D).

TABLE 1

Results from two experiments A and B using two different CaMV promoter constructs and two effector treatments (pLau6-Ac effector vs. No effector).

| CaMV promoter construct[a] | Replicates Using Two Effector Treatments | | | | Means | |
|---|---|---|---|---|---|---|
| | pLau6-Ac[b] replicate Ac-1[c] | pLau6-Ac replicate Ac-2 | No effector replicate Ne-1 | No effector replicate Ne-2 | Mean of Ac replicate values | Mean of No effector replicate values |
| −90-GUS | 0.009[d] | 0.015 | 0.053 | 0.044 | 0.012[e] | 0.049 |
| 0.7-GUS | 0.063 | 0.087 | 0.133 | 0.146 | 0.075 | 0.140 |

[a]CaMV promoter constructs are shown in FIG. 1A; the two transfection experiments, using -90-GUS and CaMV 0.7-GUS constructs, were conducted on different dates, with different batches of protoplasts. Also see c below.
[b]The pLau6-Ac effector construct used in these transfections is shown in FIG. 1B.
[c]Replicates numbered 1 and 2, as shown for both the pLau6-Ac and the No effector treatments (2 replicates each, called Ac-1 and Ac-2, and Ne-1 and Ne-2, for a total of 4 entries within a row), are 4 transfections conducted on the same day, using the same batch of protoplasts. All replicates within a single row (rows 1 and 2) used the same amount of total protein per sample measurement.
[d]Numerical values shown in the table are GUS activities (RFU per second) as measured via fluorescence at 365 nm excitation and 455 nm emission.
[e]The four mean values shown are the means of pairs of replicate measurements (four pairs), for each combination of CaMV promoter construct and effector treatment, respectively.

TABLE 2

GUS activities (RFU per second) as measured for different combinations of CaMV promoter constructs and effector constructs.

| CaMV promoter construct[a] | Mean ± S.D.[e] of Ac[b] values | Mean ± S.D. of pUC18[c] values | Mean ± S.D. of No effector values | t-value[f] and p-value[g] (Ac minus No effec.) | t-value and p-value (Ac minus pUC18) | t-value and p-value (pUC18 minus No effec.) |
|---|---|---|---|---|---|---|
| CaMV 0.7-GUS[d] | 0.053 ± 0.012 | 0.083 ± 0.026 | 0.123 ± 0.021 | t = 4.093; p = 0.027 | t = 1.482; p = 0.138 | t = 1.693; p = 0.116 |
| CaMV 0.7-GUS | 0.012 ± 0.003 | 0.040 ± 0.009 | 0.039 ± 0.006 | t = 5.692; p = 0.015 | t = 4.174; p = 0.026 | N.A.[h] |

TABLE 2-continued

GUS activities (RFU per second) as measured for different combinations of CaMV promoter constructs and effector constructs.

| CaMV promoter construct[a] | Mean ± S.D.[e] of Ac[b] values | Mean ± S.D. of pUC18[c] values | Mean ± S.D. of No effector values | t-value[f] and p-value[g] (Ac minus No effec.) | t-value and p-value (Ac minus pUC18) | t-value and p-value (pUC18 minus No effec.) |
|---|---|---|---|---|---|---|
| T-1R-90-GUS | 0.019 ± 0.001 | 0.041 ± 0.006 | 0.031 ± 0.016 | t = 1.059; p = 0.200 | t = 5.115; p = 0.018 | N.A. |
| -90-GUS | 0.024 ± 0.004 | 0.019 ± 0.013 | 0.037 ± 0.014 | t = 1.263; p = 0.167 | N.A. | t = 1.332; p = 0.157 |

[a]CaMV promoter constructs are in FIG. 1A. Experiments C and D (row 1 and 2 entries, respectively) are comparable transfections using the same CaMV 0.7-GUS promoter construct, but conducted on different dates with different protoplast batches. Entries in rows 1, 3 and 4 (all experiment C) were transfections conducted on the same date, with the same batch of protoplasts. Significant digit number (3) is the same as in the computer readout.
[b]The term Ac refers to introduction of the pLau6-Ac effector construct from FIG. 1B.
[c]This refers to the pUC18 plasmid, used as a mock effector control.
[d]All samples shown used equal amounts of total DNA per transfection and a 5:1 molar ratio of effector:reporter DNA; all treatments within each row had the same amount of total protein added per sample, prior to sample GUS activity measurement.
[e]These refer to standard deviations of two replicates; mean values are calculated from the same, two replicates.
[f]The t-value calculated is referred to as a one-tailed test with 2 degrees of freedom.
[g]The p-values (probability values) and their rejection regions are discussed in the Results section.
[h]The N.A.s mean the one-tailed t-test could not be conducted on these pairs of entries, because the expected direction of the test (e.g., pUC18 lower than no effector) did not occur; also see FIG. 2 for graphical representation of these "reversals".

All numbers shown within Tables 1 and 2 and FIG. 2 are in units of Vmax (i.e., RFU/sec), which is the rate or slope for the overall linear reaction in which the fluorescent endproduct, MU, is being produced; this rate is a direct reflection of the β-glucuronidase (GUS) enzyme available to drive the reaction, or, the "GUS activity" (Jefferson, 1987; Jim Garrido, Molecular Devices Corp., personal communication). As compared to a static measurement approach, the advantage of the kinetic measurement approach (at 365 nm excitation and 455 nm emission) used herein is that it produces a greatly enhanced significance of the slope of the linear reaction, which is generated from many points and not just from one endpoint measurement (Jefferson, 1987). All experimental measurements herein used at least 41 time points to calculate Vmax (i.e., RFU/sec). This kinetic GUS activity measurement procedure allowed reliable measurement of the slope of the MU-production reaction, and had high sensitivity, as in the Jefferson static measurement protocol (Jefferson, 1987). In addition, the kinetic approach also allowed greatly enhanced significance of the slope of the reaction due to the large number of time points collected (Jim Garrido, Molecular Devices Corp., and Isabel Ordiz, Danforth Plant Science Center, personal communications).

The hypothesis is that the Ac transposase can bind to specific transposase binding site motifs contained within a non-transposable element promoter region and that the transposase can then function as a regulator of transcription. As an initial test of this hypothesis, each of the 3 promoter constructs used (FIG. 1A) contained different numbers of putative Ac transposase binding sites, either hexamers, triplets and/or tetramers. The greatest number of such Ac binding sites (34 triplet ACG and TCG Ac binding motifs, and also tetramer ACGG and TCGG Ac binding motifs) is contained within the 0.7 kb CaMV-GUS promoter construct, in a unique, overlapping arrangement (FIGS. 1A, 3). The -90-GUS and T1R-90-GUS constructs each contain 5 copies of ACG and TCG triplet Ac transposase binding motifs (FIG. 3), and the T1R-90-GUS construct also contains 1 additional hexamer Ac transposase binding motif (FIG. 1).

Statistical methods (t-tests; graphical use of standard errors) are used in the analysis of GUS activity; this type of analysis is accepted in the current literature (P. Thompson, B. Howells, Washington Univ. Division of Biostatistics, personal communication, July 2000).

The research presented herein describes the results of four separate and sequential experiments (A, B, C, and D) conducted on 4 separate dates, each experiment utilizing a separate batch of BY-2 tobacco protoplasts, and each experiment containing internal within-experiment replication, 2 replicates per treatment. Results of experiment A are reported in Table 1, row 1; results of experiment B are reported in Table 1, row 2; all the results of experiment C are reported in Table 2, rows 1, 3 and 4, as well as graphically in FIG. 2, panels 1, 3 and 4; results of experiment D are reported in Table 2, row 2 and graphically in FIG. 2, panel 2.

GUS Activity From -90-GUS and CaMV 0.7-GUS is Repressed by Ac in Transient Assays To test if GUS activity is affected by the presence of Ac, I separately introduced two CaMV promoter constructs into BY-2 protoplasts, with and without the Ac effector construct (Table 1). The CaMV promoter constructs used were "-90-GUS" and "CaMV 0.7-GUS" (FIG. 1A) and the Ac effector construct was pLau6-Ac (FIG. 1B). These two experiments, A and B, were conducted to determine if the Ac transposase can affect GUS reporter gene activity when the GUS reporter gene is fused with a non-transposable element promoter that nevertheless contains Ac element transposase DNA binding sites.

Mean values of GUS activity in the presence of the Ac effector were lower than mean values of GUS activity in the presence of no effector (a repression effect), for each of the two CaMV promoter constructs tested (Table 1). These experiments, A and B, used equal amounts (μg) of total protein across all treatments within an experiment (see Table 1 and footnote). However, a greater amount of total DNA (i.e., the total amount of effector, reporter and carrier DNA together) was used in the Ac effector transfection reactions than in the no effector transfection reactions (4.75 times more DNA).

Measurement of GUS Activity Using Equal Total DNA Amounts, and 3 Effector Treatments: Ac, No Effector and pUC18

The excess amount of overall DNA used within the Ac transfection reactions shown in Table 1 may have affected the results (i.e., produced a lower GUS activity within the Ac treatments). To counter this possibility, equal amounts of total DNA (effector+reporter+carrier DNA) were used in all transfection reactions within all experiments (C and D) described subsequent to Table 1 (i.e., in FIG. 2, and in Table 2). A puC18 mock effector DNA control was also included in these later experiments (C and D), to test what effect the introduction of any plasmid DNA would have on GUS activity.

In FIG. 2, mean GUS activity (RFU/sec) is plotted for three effector treatments: Ac effector (FIG. 1B), no effector, and pUC18 mock effector, and also for differing CaMV 35S promoter constructs (3 reporters; FIG. 1A). Data shown in FIG. 2 argues against the GUS repression effect observed in Table 1 being solely due to an "excess-of-DNA-effect". Specifically, when a pUC18 "mock effector" (DNA alone; no protein made) control is added to protoplasts, this does not produce a distinct or significant GUS activation nor a significant GUS repression effect, as compared with no effector DNA present (see FIG. 2: mean values for pUC18 treatment are lower in 2 cases and higher in 2 cases than the respective mean values for no effector treatment and the respective pUC18 standard error bars overlap those of no effector; also see Table 2). It should be noted I have not explicitly tested what effect using differing molar ratios of effector:reporter:carrier DNA would have on GUS activity, if any.

Most importantly, for all 4 CaMV promoter constructs tested (shown on the x-axis of FIG. 2; experiments C and D), the mean value of GUS activity when the Ac effector construct is present is lower in all cases than the mean value of GUS activity when no effector construct is present; this is consistent with a repression of GUS activity in the presence of the Ac effector construct. Moreover, the 95% confidence interval shown (i.e., ±2 standard errors; FIG. 2) for the Ac effector treatment mean does not overlap with the 95% confidence interval shown for the no effector treatment mean, when "CaMV 0.7-GUS" is used as the promoter construct, in either experiments C or D (FIG. 2; see two left most panels). These 95% confidence interval graphical results are also comparable to the t-test results shown for the pairwise comparison of the Ac effector vs. no effector means (Table 2; see first two rows: "CaMV 0.7-GUS", Experiments C and D). The 95% confidence intervals for Ac effector vs. no effector treatment means do overlap, however, when the T-1R–90-GUS or –90-GUS CaMV promoter constructs (reporters) are used (FIG. 2, experiment C; see two right most panels). In all cases, the 95% confidence interval length for the Ac mean is smaller than the corresponding 95% confidence interval for either of the no effector or pUC18 mock effector means (within a given panel: FIG. 2).

Within FIG. 2 other comparisons can also be made, namely that the pUC18 and no effector 95% confidence intervals overlap in all 4 cases (i.e., in all 4 panels of FIG. 2). However, in comparing the Ac effector vs. pUC18 mock effector means (FIG. 2), there are two cases in which the Ac effector 95% confidence interval does not overlap with that of pUC18, namely for the "CaMV 0.7-GUS" (experiment D) promoter construct, and for the "T-1R–90-GUS" promoter construct (experiment C) (i.e., shown in the middle two panels in FIG. 2). In both of these cases, the Ac effector GUS activity mean value is lower than the pUC18 mock effector mean value.

Table 2 presents statistical analysis of the data shown in FIG. 2. In Table 2, statistical differences between pairs of treatment mean values are analyzed using the t-test and a null hypothesis that (sample mean 1)=(sample mean 2) plus an alternative hypothesis specifically that (sample mean 1)<(sample mean 2) (preliminary data [Table 1] suggest a repressor phenomenon a priori). An overall rejection region of 0.10 was chosen. To this rejection region the conservative Bonferroni correction for multiple comparisons was applied, which in this case results in a rejection region of (0.10÷3) =0.033 for each of 3 pairwise comparisons (Kleinbaum et al., 1988). Thus, only those entries in Table 2 may be called significant if they have p-values<0.033. Using this criterion we see that in column 8 of Table 2, GUS activity measured within the Ac effector treatment is significantly less than that measured within the no effector treatment, for the "CaMV 0.7-GUS" promoter construct, in two separate experiments: C and D (Table 2).

The only other two significant p-values in Table 2 (i.e., column 9) indicate that: GUS activity measured in the Ac effector treatment is significantly less than that measured in the pUC18 mock effector treatment, for the CaMV 0.7-GUS promoter construct (experiment D), and for the T-1R–90-GUS promoter construct (experiment C). No other p-values in Table 2 are significant by the above criteria. "N. A." values indicate the one-tailed t-test could not be performed because the effector treatment that was expected to be the lower of the two, was not lower in that case (see Table 2). The t-test significant results of Table 2 correspond with the 95% confidence interval results from FIG. 2. Differences in the absolute magnitude of GUS activity (Tables 1, 2; and among the 4 panels shown in FIG. 2) are likely due to differences in overall transfection reaction efficiency among experiments.

Discussion

Rationale, Findings, and Value of the Present Approach

The general rationale for this study is to test whether the maize Ac transposase can regulate gene expression in transient assays. To test this hypothesis, the Ac transposase gene region (i.e., an Ac effector construct) was introduced into tobacco BY-2 protoplasts along with each of three different promoter constructs via electroporation. I used promoter constructs whose overall DNA sequences are not derived from the Ac transposable element, yet each of which contains differing numbers of Ac transposase DNA binding motifs (i.e., specific short sequences found within the Ac element's terminii: hexamers, tetramers and/or triplets). Three such "CaMV 35S-GUS" promoter constructs (reporters) were tested, to determine if Ac transposase presence can affect GUS reporter gene activity when the reporter gene is fused with a non-transposable element (i.e., a native CaMV 35S) promoter region that nevertheless contains short Ac transposase binding sites.

A further rationale for specifically studying the several triplet ACG and TCG Ac transposase binding site motifs is that their organization within one of the promoter constructs used herein (i.e., the "CaMV 0.7-GUS" promoter construct) fits the general description of "CpG islands" in plants (FIG. 3). The contribution of CpG islands to gene regulation to my knowledge has not been linked with TE transposases to date; it is thus of interest to investigate the role of such CpG islands together with transposases, in affecting gene regulation in plants. Such CpG islands are, however, known to be subject to DNA methylation in plants (Messeguer et al., 1991) and therefore such sites have the potential to be involved in gene regulation. Although FIG. 3 shows such sites as clustered within a plant viral promoter (CaMV 35S), such clustered CpG island sites would also be expected to be found in plant (i.e., non-viral) gene promoters at a frequency of 1 ACG or TCG motif per 64 bases on either strand. This expected distribution (1 such triplet every 64 bases) will also be positively influenced by the overall degree of plant genome methylation, since peaks in the CpG profile (observed/expected CpG ratio) within 5' gene promoter regions are larger in methylated species than in non-methylated species (Shimizu et al., 1997). Thus, it would be expected that such ACG and TCG putative Ac transposase binding site motifs and CpG islands will have higher frequency of occurrence (>1/64 bases) within several plant genomic locations, especially within 5' plant promoters from highly methylated species. Furthermore, since many plant gene promoters are 700 bp or more in length (i.e., the size of the longest CaMV 35S plant viral promoter region studied herein; FIG. 3), and since most plant genomes are heavily methylated, it is expected that many plant promoters will have at least as many transposase binding sites—i.e., 34 such short sites—per promoter region, as are found in the native 0.7 kb CaMV promoter construct used here (see FIG. 3). Moreover, it is predicted that plant (non-viral) gene promoters could also be similarly regulated by the Ac transposase binding to such CpG islands and to Ac transposase binding sites, as found within plant gene promoters.

To summarize the findings, a significant reduction in the magnitude of GUS enzyme activity (~2.8 fold; Table 2) was observed in the presence of the Ac effector molecule, below that observed for no effector molecule present. This Ac-associated GUS enzyme activity reduction was observed for the promoter construct with the largest CaMV promoter region, "CaMV 0.7-GUS". That ~700 bp CaMV 35S native promoter region has 34 putative Ac triplet transposase binding sites (ACG or TCG), four of which are also flanked by a G residue on their 3' end (Ac tetramers) (FIG. 3). Moreover, 71% of these 34 triplet sites are overlapping one another on either DNA strand (FIG. 3). The other two promoter constructs used only contained five triplet Ac transposase binding motifs (i.e., for −90-GUS), or six Ac transposase binding motifs (i.e., for T-1R−90-GUS), namely 1 hexamer plus the same 5 triplets as in −90-GUS (FIGS. 1, 3). These later two promoter constructs, containing fewer Ac motifs, showed no significant GUS activity repression in the presence of the Ac effector molecule when equal total amounts of transfected DNA were used in all treatments (FIG. 2). This suggests a possible Ac transposase binding site dosage effect may be occurring, where a certain minimal number of Ac transposase DNA binding sites must be present to cause the GUS repression effect.

The significant differences in GUS activity found between the Ac effector treatment and the no effector treatment, for the CaMV 0.7-GUS promoter construct, are small in magnitude (FIG. 2, panels 1 and 2). However, such small differences in magnitude of gene expression (2–4 fold) can nevertheless affect important biological processes. This is demonstrated for example in biological processes such as stilbene synthase gene expression, influenced by differing promoters (2–5 fold change in GUS activity detected; Brehm et al., 1999), and in the efficiency and stability of gene expression, influenced by the presence of introns within a gene coding region (3 fold change in GUS activity detected; Lebedev and Dolgov, 2000). As a further example of a key biological process that could be affected by differences of this magnitude, a gene producing 4 times less of an enzyme product over time can cause a net result of significantly fewer reactions catalyzed by that enzyme within a cell. Finally, differences of this magnitude can be very important in biology in general; 2–4 times more or less of something may sound like a small amount, but if one organism were 2–4 times bigger than all the other organisms in a population, it would have a significant evolutionary advantage, and conversely, if it were 2–4 times smaller, it would have an evolutionary disadvantage. The same evolutionary principles can also be invoked for such small differences in gene expression, as existing within a population of genes.

Further discussion of the data is warranted. The standard errors shown graphically in FIG. 2 may appear to be large. Keep in mind, however, that 2 standard errors are shown there (i.e., the mean plus 2 standard errors and minus 2 standard errors, which is the 95% statistical confidence interval). These results and their presentation have been carefully reviewed by a statistician (Bill Howells, Division of Biostatistics, Washington University) and the conclusions reached herein are statistically sound. In fact, the presentation herein pays considerably more attention to statistical accuracy and to quantitative statistical detail than do other studies; some other studies may give no standard errors for GUS activity (e.g., Juszczuk et al., 2000), or, give only 1 standard error graphically (several studies), or, they may denote relative quantitative GUS activity merely by "yes" or "no" observations or by the numbers of plus and minus signs to reflect the intensity of GUS activity quantitatively (Manevski et al., 2000; Hua et al., 1999).

To discuss the reproducibility of the results, the CaMV 0.7-GUS promoter construct (the largest one used herein) showed a consistent repression effect (i.e., a lowered GUS activity) in the presence of the Ac effector molecule in three separate experiments: in experiment B (Table 1), experiment C (Table 2; and FIG. 2, panel 1), and experiment D (Table 2; and FIG. 2, panel 2). The smallest promoter construct tested herein (−90-GUS) also showed a consistent repression effect (i.e., a lowered GUS activity) in the presence of the Ac effector molecule, in two experiments: in experiment A (Table 1) which has been discussed in Results, and in experiment C (Table 2; FIG. 2, panel 4), although differences between the Ac and no effector treatments in experiment C were not statistically significant (FIG. 2, panel 4).

To address the numbers of measurements and replications herein, at least 41 separate data points were measured over a time course in order to generate each individual data entry (RFU/sec) given in Tables 1 and 2 and in FIG. 2. Moreover, two separate replications of each of these multi-data time point (i.e., 41 time point) entries were made, for each treatment within a single protoplast batch; and, experiments A, B, C, and D each used 1 separate protoplast batch. This number of replicates is comparable to the number given in current literature (e.g., Ludewig and Sonnewald, 2000). The number of exact replications herein using separate protoplast batches was N=2 (i.e., for the CaMV 0.7-GUS construct, in experiments C and D), and the number of total experimental replicates using separate protoplast batches was N=3 (i.e., for the CaMV 0.7-GUS construct, in experiments B, C, and D).

The units in which GUS activity is expressed herein (i.e., RFU/sec or "Vmax"), although not completely traditional, are appropriate—GUS activity can be expressed in multiple ways in the literature (e.g., Baum et al., 1999). Furthermore, the units used herein—RFU/sec (Vmax)—measure the slope for the overall linear reaction in which the fluorescent endproduct, MU, is being produced. This rate, measured kinetically over time at 365 nm excitation and 455 nm emission, is a direct reflection of the β-glucuronidase enzyme available to drive the reaction, or the "GUS activity" (Jefferson, 1987; Jim Garrido, Molecular Devices Corp., personal communication).

The order of presentation and the content of each of the four experiments (A, B, C, and D) has been discussed within the 2 Results subsections entitled: "GUS activity from −90-GUS and CaMV 0.7-GUS is repressed by Ac in transient assays" and "Measurement of GUS activity using equal total DNA amounts, and 3 effector treatments: Ac, no effector and pUC18". The rationale for including both sets of data (i.e., the initial experiments A and B, conducted without a plasmid-only effector control, as well as the sequentially later experiments C and D, conducted with such a plasmid-only effector control) is discussed below. Moreover, as the data shown herein report a novel finding and not a repetition or confirmation of an existing finding—i.e., the Ac transposase has not previously been shown to be able to act on non-transposon promoters, nor has it been implicated in having a secondary function aside from that in transposition, namely a novel function as a transcription factor or as a transcriptional modifier of non-TE genes—I feel that the series of 4 sequential experiments presented herein as a whole will be of general interest and will lead to additional work in this area. The presentation of all 4 experiments further allows the reader to understand the initial steps taken (experiments A and B) and the unexpected findings (a repression effect) which then led the author to design and gather data for the most conclusive experiments existing to date (i.e., experiments C and D).

To my knowledge these data constitute the first demonstration of a GUS repression effect (i.e., a lowered GUS activity) in the presence of the Ac transposase coding region, and using a non-transposable element (CaMV 35S) promoter to drive GUS expression. An analogous transposition protein within the maize Suppressor-mutator (Spm) transposable element system, TnpA, can function as a transcriptional repressor of the unmethylated Spm promoter (Fedoroff, 1999; Schlappi et al., 1994). However, this Spm effect is repression of a transposable element (TE) promoter, whereas the Ac effect shown here is a putative repression of a non-transposable element (CaMV 35S) promoter containing TE transposase binding sites. Thus, the current findings indicate that more wide-ranging Ac transposase-induced repression effect can occur.

This example thus describes the interesting observation of a novel phenomenon (repression of GUS activity in the presence of Ac).

The results herein is opposed to the results of Fridlender et al. (1996), who did not find repression under similar circumstances. Possible reasons why Fridlender et al. found no significant reduction in CaMV promoter activity by the Ac TPase, and such reduction in activity was found herein, are: (a) Fridlender et al. used a much shorter, truncated −67 CaMV 35S promoter which has only 1 full and 1 partial triplet Ac TPase binding motif (i.e., 5' TCG 3' and part of 5' ACG 3'), and which has no triplet motifs overlapping with one another, as compared with the longer, 700 bp CaMV 35S promoter used herein, which has 34 such triplet motifs, 24 of which overlap with one another (FIG. 3); (b) in the "35S: GUS" construct they used, the GUS reporter is under the control of the −67 CaMV 35S promoter, fused to the tobacco mosaic virus (TMV) 5' leader sequence called omega, a sequence known to enhance the expression of foreign gene transcripts both in vitro and in vivo; and (c) there may be differences in the level of TPase expression produced in the two papers, and/or, differences between the two protoplast cell systems utilized.

Specificity and Causes of Lowered GUS Activity in the Presence of Ac: is it Due to Ac DNA RNA or Protein?

Significantly lower GUS enzyme activity was produced in the presence of the Ac effector (transposase-encoding) construct, below that level produced when no effector construct is present. This suggests that a down regulation or transcriptional repression of the gusA gene may be occurring in the presence of the Ac transposase. The lowered GUS enzyme activity observed is most likely specifically associated with overexpression of the Ac transposase, as overexpression of other (non-Ac transposase) proteins within BY-2 cells does not always produce a repression of the CaMV 35S promoter-driven gsA reporter gene (I. Ordiz, personal communication).

Results from both comparative GUS activity measurements and from post-transfection cell viability counts (discussed below) further suggest that the lowered GUS activity shown here is not an effect produced solely by the presence of the effector DNA plasmid (i.e., it is not a "DNA only" effect, and instead the Ac protein and/or the Ac RNA is likely to be involved in producing the lowered GUS activity).

Comparative GUS activity measurements permitted the following two conclusions about the topic of lowered GUS activity being due to a "DNA plasmid only" effect: (1) statistically, there is no detectable difference in the amount of GUS activity produced from the pUC18"DNA only" mock effector treatment versus from a no effector treatment (i.e., the null hypothesis was accepted in all pUC18 vs. no effector comparisons shown in FIG. 2 and in Table 2); and (2) statistically, there is a detectable difference in the amount of GUS activity produced from the Ac effector treatment versus from the pUG18 mock effector treatment—indeed, the Ac effector treatment is significantly lower than the pUC18 mock effector treatment, in terms of their mean GUS activities in 2 cases (Table 2; FIG. 2).

These two above results collectively indicate that the lowered GUS activity observed is most likely not due to the Ac effector DNA causing the effect, because a DNA vector alone—pUC18—(i.e., one with no proteins made that are presumed to bind to the CaMV 35S promoter) produced no significant repression effect.

Furthermore, even if there were a slight gusA repression effect produced in response to the Ac DNA sequences being mildly "toxic" to the BY-2 cells, then it can still be argued that the overall (total amount) of GUS activity repression produced by Ac is not due to an "Ac DNA construct-induced" repression effect only. This can be argued because GUS enzyme levels induced in the presence of the Ac (transposase-encoding) construct were significantly lower than those induced in the presence of the pUC18 (DNA only) construct, in 2 cases, suggesting that additional factors beyond simply the presence of a DNA molecule were causing the GUS repression. Such additional causative factors could be the Ac protein and/or the Ac RNA.

Cell viability observations further strengthen conclusions about the lowered GUS activity not being due to a "DNA only" effect: 24 hour post-transfection cell viability counts showed the Ac effector plasmid alone (without reporter or carrier DNA added), when transfected into BY-2 cells in a quantity of 120 µg DNA, yielded an overall cell viability of 42.8% (MacRae and Brown, pers. obs.; data not shown). In addition, there were no large differences observed among 24 hr. post-transfection cell viabilities as measured for any of the 3 different effector treatments, nor for any of the reporter constructs used. Cell viability observations together with GUS data, argue strongly against the possibility of an "Ac super-toxic" DNA sequence killing BY-2 cells and thus producing lowered GUS activity in the presence of the Ac effector. Ac RNA and protein molecules remain as most probable candidates for causing the lowered GUS activity.

EXAMPLE 2

Cloning and Expression of the Maize Ac TPase in *Saccharomyces cerevisiae*

Two 30 bp PCR primers were designed so as to amplify the 3.1 kb maize Ac TPase coding region out of a vector construct called pLau6-Ac (see Example 1 for a description of this maize genomic clone construct). These primers have the sequence primer 1: 5' GGAACCCG-GATCCCACT-TCGGCTAGCCGGC 3' (SEQ ID NO:4). primer 2: 5' GGAACCCG-GATCCACCAAGGCTCATCTGTC 3' (SEQ ID NO:5). A 7-bp buffer seq. is italicized and a BamHI site is underlined. The BamH1 cutting site is shown by a dash.

Each of the two PCR primers above contains a 7-base restriction enzyme buffer sequence (many restriction enzymes cleave better, if their cutting site is flanked by greater than 1 DNA base), and also a BamHI restriction enzyme recognition site.

Using the above primers, the Ac TPase was amplified from pLau6-Ac by standard methods. The amplified TPase gene was then digested with BamH1. A yeast plasmid vector, pYES2/NT-A (Invitrogen) was also digested with BamH1, then treated with calf alkaline phosphatase (New England Biolabs). The vector and insert were then ligated together, and used to transform *E. coli* by standard methods. Plasmids isolated from the transformed *E. coli* were tested for the correct insertion and orientation by restriction enzyme digestion and gel electrophoresis.

Plasmids with the proper insertion were used to transform *S. cerevisiae* INV Sc1 cells using a standard LiAc protocol, with selection on SC DO-uracil plates containing 2% glucose. The presence of the pYES2/NT-A-Ac plasmid in the tranformed yeast was certified by PCR, using the previously described primers.

The pYES/TPase yeast cells were induced with a galactose induction medium to express the TPase.

To assay for production of the N-terminal 6X His-tagged recombinant protein that is produced from all correctly expressed pYES2/NT yeast vectors, nickel-coated 96-well ELISA plates (Sigma), specially designed to detect such recombinant HIS proteins, were used.

FIG. 4 provides an ELISA protocol, using each of 3 primary antibodies (reactive to the 6× His tag, Ac TPase N terminus, and Ac-TPase C terminus). All three ELISAs established that the yeast cells produced TPase.

To prepare recombinant protein for the ELISAs, frozen yeast cells, harvested 6 hrs. post-GAL promoter induction, were lysed using the Zymo Research protocol, as follows. To the yeast cells, 25 ml of Y-lysis buffer and 1 ml of Zymolase enzyme were added. Cells were incubated at 37° C. for 60 min. To remove Y-lysis buffer, cells were centrifuged at 500× g for 5 min. After removal of the supernatant, pellets were resuspended in 40 ml of Extraction Buffer (0.1 M Tris-HCl, pH 7.6).

TABLE 3

ELISA readings (405 nm) using an anti-6X HIS 1° antibody.

| Post-PNPP Time Point | Extraction Buffer Controls (3) | | | Ac Clone 23 | Ac Clone 31 |
|---|---|---|---|---|---|
| 30 min | 0.010 | −0.004 | −0.004 | 0.058 | 0.123 |
| 1.5 hr | 0.018 | −0.004 | −0.004 | 0.121 | 0.268 |
| 18 hr | 0.178 | −0.017 | 0.129 | 0.892 | 1.672 |

It is concluded that both Ac yeast clones #23 and #31 are expressed after 6 hrs. GAL promoter induction with galactose, as determined via use of an anti-6× HIS 1° antibody, which bound to the 6×-HIS tag on the N-terminus of the recombinant Ac TPase protein made in yeast.

To further confirm Ac TPase expression in yeast cells, the same GAL promoter induction and 96-well Elisa methods as above were performed, however this time two separate 1° antibodies specific to 2 overlapping Ac TPase protein regions were used: (a) an "anti-Ac TPase N-terminal region 1° antibody (to amino acid residues 103–465)", called 'anti 10 ATG'; and (b) an "anti-Ac TPase C-terminal region 1° antibody (to amino acid residues 189–807)", called 'anti Asu'. Both of these anti-Ac TPase antibodies (to 2, overlapping Ac protein regions), were obtained from Dr. Reinhard Kunze (Univ. of München, Munich, Germany). GAL promoter induction points were 14 hrs. and 20 hrs. (i.e., these were the two times when cells were harvested, post GAL promoter induction).

The second set of ELISA plate readings (405 nm) were as follows. The only differences from the previous results presented were (a) two different, anti-Ac TPase 1° antibodies were used; (b) yeast cells were harvested 14 hrs. and 20 hrs. post GAL promoter induction; and (c) post-PNPP Absorbance reading 405 nm time points were: 30 min., 1.5 hrs., and 6.5 hrs.

TABLE 4

ELISA readings (405 nm) using two anti-Ac TPase 1° antibodies.

| Post-PNPP time points | Extraction buffer controls (3) | Ac Clone 23 | | Ac Clone 31 | |
|---|---|---|---|---|---|
| | | 14 hr | 20 hr | 14 hr | 20 hr |
| 30 min | −0.026, 0.019, 0.020 | 0.156* | 0.134* | 0.078 ‡ | 0.221 ‡ |
| 1.5 hr | −0.003, 0.032, 0.027 | 0.384* | 0.485* | 0.239 ‡ | 0.854 ‡ |
| 6.5 hr | 0.126, 0.135, 0.094 | 1.023* | 1.410* | 0.733 ‡ | 2.080 ‡ |

The * samples were incubated with the 'anti 10 ATG' Ac-TPase 1° antibody (to residues 103–465), whereas the ‡ samples were incubated with the 'anti Asu' Ac-TPase 1° antibody (to residues 189–807). It is concluded that both Ac yeast clones #23 and #31 are expressed, after 14 and 20 hrs. GAL-promoter induction with galactose. Clone #23 expression was detected by a 1° antibody against Ac TPase residues 103–465, and clone #31 expression was detected by a 1° antibody against Ac TPase residues 189–807.

From the foregoing, it will be understood that, although specific embodiments of this invention have been described herein for purposes of illustration, various modifications and improvements may be made without departing from the spirit and scope of the invention. Accordingly, the invention is not limited by the above Preferred Embodiment section nor by any other section, except by the overall scope and spirit of the invention as indicated by the appended list of claims which follow below. It is further contemplated that the appended claims listed will cover any such modifications, improvements, or embodiments.

In view of the above materials, it will be seen that the several advantages of the invention are achieved and other advantages attained.

As various changes could be made in the above methods and compositions without departing from the scope of the invention, it is intended that all matter contained in the above description and also shown in the accompanying figures, tables, appendices, and drawings shall be interpreted as illustrative and not in a limiting sense.

APPENDIX

The 4810 bp complete sequence of the Activator (Ac) transposable element from the maize wx-m9 allele encoding the Ac trnsposase; from accession number k01964 within GenBank. It should be noted that, as also described in the "Example" FIG. 1B legend herein, the relevant sequences used within the pLau6-Ac vector herein are a 3.28 kb intrnal BanII restrictio fragment (containing introns) and encoding the transposase, and also containing only nucleotides 1070–4352 from the full 4810 bp Ac wx-m9 allele shown below; these nucleotides 1070–4352 are located on the other (complementary) DNA srand from that given in the K01964 accesion DNA sequence shown below. Please also see 'Methods' section of the "Example" above, for the full confirmation of the Ac "effector" DNA sequence used herein.

Several additional existing maize Activator (Ac) alleles, as well as the related Dissociation (Ds) alleles, may also have properties useful to, and consistent with, the present invention. Such additional Ac and Ds maize alleles can be found within GenBank at PubMed'web site (http://www.ncbi.nlm.nih.gov/PubMed/), under search NUCLEOTIDE or keyword, then display GENBANK entry. Examples include Accessions K01964, X05424, and X05425.

Accession K01964 (SEQ ID NO:6) Maize transposable element Activator (Ac9) from the waxy locus BASECOUNT 1390 a 1063c 1063g 1294t ORIGIN 5 bp upstream of PstI site.

```
   1  ctgcaggcgg aggtcgggct cccggtggac cggaacatcc cgctggtggc
      gttcatcggc
  61  aggctggaag agcagaaggg ccccgacgtc atggcggccg ccatcccgca
      gctcatggag
 121  atagggatga aaacggtcgg taacggtcgg taaaatacct ctaccgtttt cattttcata
 181  tttaacttgc gggacggaaa cgaaaacggg atataccggt aacgaaaacg
      aacgggataa
 241  atacggtaat cgaaaaccga tacgatccgg tcgggttaaa gtcgaaatcg gacgggaacc
 301  ggtattttg ttcggtaaaa tcacacatga aaacatatat tcaaaactta aaaacaaata
 361  taaaaaattg taaacacaag tcttaattaa acatagataa aatccatata aatctggagc
 421  acacatagtt taatgtagca cataagtgat aagtcttggg ctcttggcta acataagaag
 481  ccatataagt ctactagcac acatgacaca atataaagtt taaaacacat attcataatc
 541  acttgctcac atctggatca cttagcatgc ataaactatt acaaccaagg ctcatcgtc
 601  aacaaacata agacacattg ctcatggaga ggagccactt gctacatctt cattattctt
 661  agaaaattct attgcgtctt catcctgtta atacacaaaa ataagtcagt tttggataaa
 721  taaatacata tagaagaaca tgaattgata tgcagggagt ataaataaat acatatagga
 781  gaacatgaat ctgtgaacta acacggctgg gagctaggca gctagcagct agcgcctaac
 841  agctgggagc ctaacgcta gcagctagca gccaatcaaa acaaggcgac
      aaggcgcatg
 901  cagtgagatc aaaaatctgt taatgccagc catgcaggga gtataacacg gctgggcagc
 961  aaggcgcatg catcaaaaca aggcgacaga caacagccca tgcatcaaaa
      cagtagtgaa
1021  taatagcaaa ttaatagccc atgcacgaag taaataataa tctttaaata cctcatccat
1081  atgattctca tgatttgttg cagcagcaat aacagagtct agcacctcga gatcaccaat
1141  cattgttgga aaatatgtag caccttgaat gacacaaata tgcatcaata taagtaaaat
1201  aattgttgaa taactataaa ttggaacttc attataacat atatgcattc accttttcta
1261  gatgctgcta cccaatcttt tgtgcatatc aaagcttcaa caatctccga accaagacga
1321  ttgcggtaag gatcaacaac acgaccacca gcactgaacg cagactcaga
      agcaacagtt
1381  gacacttgta ttgctagcac atcccttgca atttgggtga gaataggata ttctgcaacc
1441  cttcccctcc accatgataa aatatcaaac tgaccactat gcttcaaaag gggttcagac
1501  atatatttat ccaattcatt tgactctact tgatcataat ccttcaactc atgcaaatag
1561  ttttgaaatt catcatcttc attttccatc aaggtatcat ccatactatc attagtagtt
1621  gtctttgtct ttggagctga aggactacaa ctagaataga attgataaa ttttctaatg
1681  accctaacaa agtcatctac atgaactttg tatgaatcac catgaaattt tttcatatag
1741  aactcaatca atatttttctt gtacctaggg tcaaggaagc atgctacagc tagtgcaata
1801  ttagacactt tccaatattt ctcaaactt tcactcattg caacggccat tctcctaatg
1861  acaaatttt catgaacaca ccattggtca atcaaatcct ttatctcaca gaaacctttg
1921  taaaataaat ttgcagtgga atattgagta ccagatagga gttcagtgag atcaaaaaac
1981  ttcttcaaac acttaaaaag agttaatgcc atcttccact cctcggcttt aggacaaatt
2041  gcatcgtacc tacaataatt gacatttgat taattgagaa tttataatga tgacatgtac
2101  aacaattgag acaaacatac ctgcgaggat cacttgtttt aagccttatt agtgcaggct
2161  tataatataa ggcatccctc aacatcaaat aggttgaatt ccatctagtt gagacatcat
2221  atgagatccc tttagattta tccaagtcac attcactagc acacttcatt agttcttccc
2281  actgcaaagg agaagatttt acagcaagaa caatcgcttt gattttctca attgttcctg
2341  caattacagc caagccatcc tttgcaacca agttcagtat gtgacaagca cacctcacat
2401  gaaagaaagc accatcacaa actagatttg aatcagtgtc ctgcaaatcc tcaattatat
2461  cgtgcacagc tacttcattt gcactagcat tatccaaaga caaggcaaac aattttttct
2521  caatgttcca cttaaccatg attgcagtga aggtttgtga taacctttgg ccagtgtggc
2581  gcccttcaac atgaaaaaag ccaacaattc ttttttggag acaccaatca tcatcaatcc
2641  aatggatggt gacacacatg tatgacttat tttgacaaga tgtccacata tccatagttg
2701  tactgaagcg agactgaaca tcttttagtt ttccataaa ctttttcttt tcttccaat
2761  acaaatccat gatatatttt ctagcagtga cacgggactt tattggaaag tgagggcgca
2821  gagacttaac aaactcaaca aagtactcat gttctacaat attgaaagga tattcatgca
2881  tgattattgc caaatgaagc ttctttaggc taaccacttc atcgtactta taaggctcaa
2941  tgagatttat gtctttgcca tgatccttt cactttttag acacaactga cctttaacta
3001  aactatgtga tgttctcaag tgatttcgaa atccgcttgt tccatgatga ccctcagccc
3061  tatacttagc cttgcaatta ggaaagttgc aatgtcccca tacctgaacg tatttctttc
3121  catcgaccctc cacttcaatt tccttcttgg tgaaatgctg ccatacatcc gatgtgcact
3181  tctttgccct cttctgtggt gcttcttctt cgggttcagg ttgtggctgt ggttgtggtt
3241  ctggttgtgg ttgtggttgt ggttgtggtt catgaacaat agccatatca tcttgactcg
3301  gatctgtagc tgtaccattt gcattactac tgcttacact ctgaataaaa tgcctctcgg
3361  cctcagctgt tgatgatgat ggtgatgtgc ggccacatcc atgcccacgc gcacgtgcac
3421  gtacattctg aatccgacta gaaggctcta gcttttcttt tcaaccctgt tataaacaga
3481  ttttcgtat tattctacag tcaatatgat gcttcccaat ctacaaccaa ttagtaatgc
3541  taatgctatt gctactgttt ttctaatata taccttgagc atatgcagag aatacggaat
3601  ttgttttgcg agtagaaggc gctcttgtgg tagacatcaa cttggccaat cttatggctg
3661  agcctgaggg aggattattt ccaaccggag gcgtcatctg aggaatggag tcgtagccgg
3721  ctagccgaag tggagagcag agccctggac agcaggtgtt cagcaatcag cttggtgctg
3781  tactgctgtg acttgtgagc acctggacgg ctggacagca atcagcaggt gttgcagagc
3841  ccctggacag cacacaaatg acacaacagc ttggtgcaat ggtgctgacg tgctgtactg
3901  ctaagtgctg tgagcctgtg agcagccgtg gagacaggga gaccgcggat
      ggccggatgg
3961  gcgagcgccg agcagtggag gtctggagga ccgctgaccg cagatggcgg
      atgcggatg
4021  ggcggaccgc ggatgggcga gcagtggagt ggaggtctgc gcggatgggc
      ggaccgcggc
4081  gcggatgggc gagtcgcgag cagtggagtg gagggcggac cgtggatggc
      ggcgtctgcg
4141  tccggcgtgc cgcgtcacgg ccgtcaccgc gtgtggtgcc tggtgcagcc
      cagcggccgg
4201  ccggctggga gacagggaga gtcggagaga gcaggcgaga gcgagacgcg
      cgtcggcgtc
4261  ggcgtgcggc tggccggcgtc cggactccgg cgtgggcgcg tggccgcgtg
      tgaatgtgtg
4321  atgctgttac tcgtgtggtg cctgccgcct gggagagagg cagagcagcg ttcgctaggt
4381  atttcttaca tgggctgggc ctcagtggtt atggatggga gttggagctg gccatattgc
4441  agtcatcccg aattagaaaa tacggtaacg aaacgggatc atcccgatta aaaacgggat
4501  cccggtgaaa cggtcgggaa actagctcta ccgtttccgt ttccgtttac cgttttgtat
4561  atcccgtttc cgttccgttt tcgtttttta cctcgggttc gaaatcgatc gggataaaac
4621  taacaaaatc ggttatacga taacggtcgg tacgggattt tcccatccta ctttcatccc
4681  tgcatggaga tggtggagaa cgtgcagatc gttctgctgg tacgtgtgcg ccgcccgcca
4741  cccggctact acatgcgtgt atcgttctac tggaacatac gtgtgagcaa cgcgatggat
4801  aatgctgcag
```

A second relevant maize Ac transposon DNA sequence (ORFa)(SEQ ID NO:8), and the accompanying encoded 807 amino acid sequence (SEQ ID NO:7) constituting the Ac transposase protein, is given below.

Maize transposable element Activator (Ac) major transcript—Accession X05424 X05425

```
MTPPVGNNPPSGSAIRLAKLMSTTRAPSTRKTNSVFSAYAQGLKRKAEASSSRIQN
VRARARGHGCGRTSPSSSTAEAERHFIQSVSSSNANGTATDPSQDDMAIVHEPQP
QPQPQPEPQPQPQPEPEEEAPQKRAKKCTSDVWQHFTKKEIEVEVDGKKYVQVW
GHCNFPNCKAKYRAEGHHGTSGFRNHLRTSHSLVKGQLCLKSEKDHGKDINLIEP
YKYDEVVSLKKLHLAIIMHEYPFNIVEHEYFVEFVKSLRPHFPIKSRVTARKYIMDLYL
EEKEKLYGKLKDVQSRFSTTMDMWTSCQNKSYMCVTIHWIDDDWCLQKRIVGFF
HVEGRHTGQRLSQTFTAIMVKWNIEKKLFALSLDNASANEVAVHDIIEDLQDTDSN
LVCDGAFFHVRCACHILNLVAKDGLAVIAGTIEKIKAIVLAVKSSPLQWEELMKCAS
ECDLDKSKGISYDVSTRWNSTYLMLRDALYYKPALIRLKTSDPRRYDAICPKAEEWK
MALTLFKCLKKFFDLTELLSGTQYSTANLFYKGFCEIKDLIDQWCVHEKFVIRRMAV
AMSEKFEKYWKVSNIALAVACFLDPRYKKILIEFYMKKFHGDSYKVHVDDFVRVIRK
LYQFYSSCSPSAPKTKTTTNDSMDDTLMENEDDEFQNYLHELKDYDQVESNELDK
YMSEPLLKHSGQFDILSWWRGRVAEYPILTQIARDVLAIQVSTVASESAFSAGGRVV
DPYRNRLGSEIVEALICTKDWVAASRKGATYFPTMIGDLEVLDSVIAAATNHENHM
DEDEDAIEFSKNNEDVASGSSP
    1 cagggatgaa agtaggatgg gaaaatcccg taccgaccgt tatcgtataa ccgattttgt
   61 tagttttatc ccgatcgatt tcgaacccga ggtaaaaaac gaaaacggaa cggaaacggg
  121 atatacaaaa cggtaaacgg aaacggaaac ggtagagcta gtttcccgac cgtttcaccg
  181 ggatcccgtt tttaatcggg atgatcccgt ttcgttaccg tattttctaa ttcgggatga
  241 ctgcaatatg gccagctcca actccatcc ataaccactg aggcccagcc catgtaagaa
  301 atacctagcg aacgctgctc tgcctctctc ccaggcggcc aggcaccaca cgagtaacag
  361 catcacacat tcacacgccg ccacgcgccc acgccggagt ccggacgccg ccagccgcac
  421 gccgacgccg gcgacgcgtc tcgctctcgc ctgctctctc cgactctccc tgtctcccag
  481 ccggccggcc gctgggctgc accaggcacc acacgcggtg acggccgtga cgcggcacgc
  541 cggacgcaga cgccgccatc cacggtccgc cctccactcc actgctcgcg actcgcccat
  601 ccgcgccgcg gtccgcccat ccgcccagac ctccactcca ctgctcgccc atccgcggtc
  661 cgcccatccg ccatccgcca tctgcggtca gcggtcctcc agacctccac tgctcggcgc
  721 tcgcccatcc ggccatccgc ggtctccctg tctccacggc tgctcacagg ctcacagcac
  781 ttagcagtac agcacgtcag caccattgca ccaagctgtt gtgtcatttg tgtctgtcc
  841 aggggctctg caacacctgc tgattgctgt ccagccgtcc aggtgctcac aagtcacagc
  901 agtacagcac caagctgatt gctgaacacc tgctgtccag ggctctgctc tccacttcgg
  961 ctagccggct acgactccat tcctcagatg acgcctccgg ttggaaataa tcctccctca
 1021 ggctcagcca taagattggc caagttgatg tctaccacaa gagcgccttc tactcgcaaa
 1081 acaaattccg tattctctgc atatgctcaa ggtatatatt agaaaaacag tagcaatagc
 1141 attagcatta ctaattggtt gtagattggg aagcatcata ttgactgtag aataatacga
 1201 aaaatctgtt tataacaggg ttgaaaagaa aagctgaagc ctcttctagt cggattcaga
 1261 atgtacgtgc acgtgcgcgt gggcatggat gtggccgcac atcaccatca tcatcaacag
 1321 ctgaggccga gaggcatttt attcagagtg taagcagtag taatgcaaat ggtacagcta
 1381 cagatccgag tcaagatgat atggctattg ttcatgaacc acaaccacaa ccacaaccac
 1441 aaccagaacc acaaccacag ccacaacctg aacccgaaga agaagcacca cagaagaggg
 1501 caaagaagtg cacatcggat gtatggcagc atttcaccaa gaaggaaatt gaagtggagg
 1561 tcgatggaaa gaaatacgtt caggtatggg gacattgcaa ctttcctaat tgcaaggcta
 1621 agtatagggc tgagggtcat catggaacaa gcggatttcg aaatcacttg agaacatcac
 1681 atagtttagt taaaggtcag ttgtgtctaa aaagtgaaaa ggatcatggc aaagacataa
 1741 atctcattga gccttataag tacgatgaag tggttagcct aaagaagctt catttggcaa
 1801 taatcatgca tgaatatcct ttcaatattg tagaacatga gtactttgtt gagtttgtta
 1861 agtctctgcg ccctcacttt ccaataaagt cccgtgtcac tgctagaaaa tatatcatgg
 1921 atttgtattt ggaagaaaaa gaaaagttgt atggaaaact aaaagatgtt cagtctcgct
 1981 tcagtacaac tatggatatg tggacatctt gtcaaaataa gtcatacatg tgtgtcacca
 2041 tccattggat tgatgatgat tggtgtctcc aaaaaagaat tgttggcttt tttcatgttg
 2101 aagggcgcca cactggccaa aggttatcac aaaccttcac tgcaatcatg gttaagtgga
 2161 acattgagaa aaaattgttt gccttgtctt tggataatgc tagtgcaaat gaagtagctg
 2221 tgcacgatat aattgaggat ttgcaggaca ctgattcaaa tctagtttgt gatggtgctt
 2281 tctttcatgt gaggtgtgct tgtcacatac tgaacttggt tgcaaaggat ggcttggctg
 2341 taattgcagg aacaattgag aaaatcaaag cgattgttct tgctgtaaaa tcttctcctt
 2401 tgcagtggga agaactaatg aagtgtgcta gtgaatgtga cttggataaa tctaaaggga
 2461 tctcatatga tgtctcaact agatggaatt caacctattt gatgttgagg gatgccttat
 2521 attataagcc tgcactaata aggcttaaaa caagtgatcc tcgcaggtat gtttgtctca
 2581 attgttgtac atgtcatcat tataaattct caattaatca aatgtcaatt attgtaggta
 2641 cgatgcaatt tgtcctaaag ccgaggagtg gaagatggca ttaactcttt ttaagtgttt
 2701 gaagaagttt tttgatctca ctgaactcct atctggtact caatattcca ctgcaaattt
 2761 attttacaaa ggtttctgtg agataaagga tttgattgac caatggtgtg ttcatgaaaa
 2821 atttgtcatt aggagaatgg ccgttgcaat gagtgaaaag tttgagaaat attggaaagt
 2881 gtctaatatt gcactagctg tagcatgctt ccttgaccct aggtacaaga aaatattgat
 2941 tgagttctat atgaaaaaat ttcatggtga ttcatacaaa gttcatgtag atgactttgt
 3001 taggggtcatt agaaaattgt atcaattcta ttctagttgt agtccttcag ctccaaagac
 3061 aaagacaact actaatgata gtatggatga taccttgatg gaaaatgaag atgatgaatt
 3121 tcaaaactat ttgcatgagt tgaaggatta tgatcaagta gagtcaaatg aattggataa
 3181 atatatgtct gaaccccttt tgaagcatag tggtcagttt gatattttat catggtggag
 3241 gggaagggtt gcagaatatc ctattctcac ccaaattgca agggatgtgc tagcaataca
```

-continued

```
3301 agtgtcaact gttgcttctg agtctgcgtt cagtgctggt ggtcgtgttg ttgatcctta
3361 ccgcaatcgt cttggttcgg agattgttga agctttgata tgcacaaaag attgggtagc
3421 agcatctaga aaaggtgaat gcatatatgt tataatgaag ttccaattta tagttattca
3481 acaattattt tacttatatt gatgcatatt tgtgtcattc aaggtgctac atatttcca
3541 acaatgattg gtgatctcga ggtgctagac tctgttattg ctgctgcaac aaatcatgag
3601 aatcatatgg atgaggtatt taaagattat tatttactc gtgcatgggc tattaatttg
3661 ctattattca ctactgtttt gatgcatggg ctgtttgctg tcgccttgtt ttgatgcatg
3721 cgccttgctg cccagccgtg ttatactccc tgcatggctg gcattaacag attttgatc
3781 tcactgcatg cgccttgtcg ccttgtttg attggctgct agctgctagc tgttaggctc
3841 ccagctgtta ggcgctagct gctagctgcc tagctcccag ccgtgttagt tcacagattc
3901 atgttctcct atatgtattt atttatactc cctgcatatc aattcatgtt cttctatatg
3961 tatttattta tccaaaactg acttattttt gtgtattaac aggatgaaga cgcaatagaa
4021 ttttctaaga ataatgaaga tgtagcaagt ggctcctctc catgagcaat gtgtcttatg
4081 tttgttgaca gatgagcctt ggttgtaata gtttatgcat gctaagtgat ccagatgtga
4141 gcaagtgatt atgaatatgt gttttaaact ttatattgtg tcatgtgtgc tagtagactt
4201 atatggcttc ttatgttagc caagagccca agacttatca cttatgtgct acattaaact
4261 atgtgtgctc cagatttata tggattttat ctatgtttaa ttaagacttg tgtttacaat
4321 ttttatatt tgtttttaag ttttgaatat atgttttcat gtgtgatttt accgaacaaa
4381 aataccggtt cccgtccgat ttcgacttta acccgaccgg atcgtatcgg ttttcgatta
4441 ccgtatttat cccgttcgtt ttcgttaccg gtatatcccg tttcgtttc cgtcccgcaa
4501 gttaaatatg aaaatgaaaa cggtagaggt attttaccga ccgttaccga ccgttttcat
4561 cccta
```

What is claimed is:

1. A method of repressing expression of a recombinant gene in a plant cell, wherein the expression of the recombinant gene is not controlled by a promoter that is derived from a transposable element, the method comprising:
    a) introducing in vitro a 0.7 kB polynucleotide fragment into or adjacent to the gene, said polynucleotide fragment comprising the native configuration of Ac transposase binding motifs contained in the 0.7 kB HindIII/NcoI fragment of the native CaMV35S promoter;
    b) introducing the gene into the cell; and
    c) introducing into the cell a transposase from an Ac element.

2. The method of claim 1, wherein the transposase is introduced by transfecting the cell with a polynucleotide sequence encoding the transposase.

3. The method of claim 2, wherein the polynucleotide sequence encoding the transposase encodes a transposable element.

4. The method of claim 1, wherein the plant is a monocot.

5. The method of claim 1, wherein the plant is a dicot.

6. The method of claim 1, wherein the plant is a member of the Solanaceae family.

7. The method of claim 1, wherein the plant is a tobacco plant.

8. The method of claim 1, wherein the polynucleotide fragment is introduced into an intron or introns of the recombinant gene.

9. The method of claim 1, wherein the polynucleotide fragment is introduced into an exon or exons of the recombinant gene.

10. The method of claim 1, wherein the polynucleotide fragment is introduced into a 5' leader region of the recombinant gene.

11. The method of claim 1, wherein the polynucleotide fragment is introduced into a 3' trailer region of the recombinant gene.

12. The method of claim 1, wherein the gene is a proto-oncogene.

13. The method of claim 1, wherein the gene is a key gene in a biochemical pathway.

14. The method of claim 1, wherein the gene is operably linked to an inducible promoter.

15. The method of claim 14, wherein the inducible promoter is a chemically-induced promoter.

16. The method of claim 14 wherein the inducible promoter is induced by an environmental stress.

17. The method of claim 1, wherein the polynucleotide fragment comprises the 0.7 kB HindIII/NcoI fragment of the native CaMV35S promoter.

* * * * *